Figure 1G:
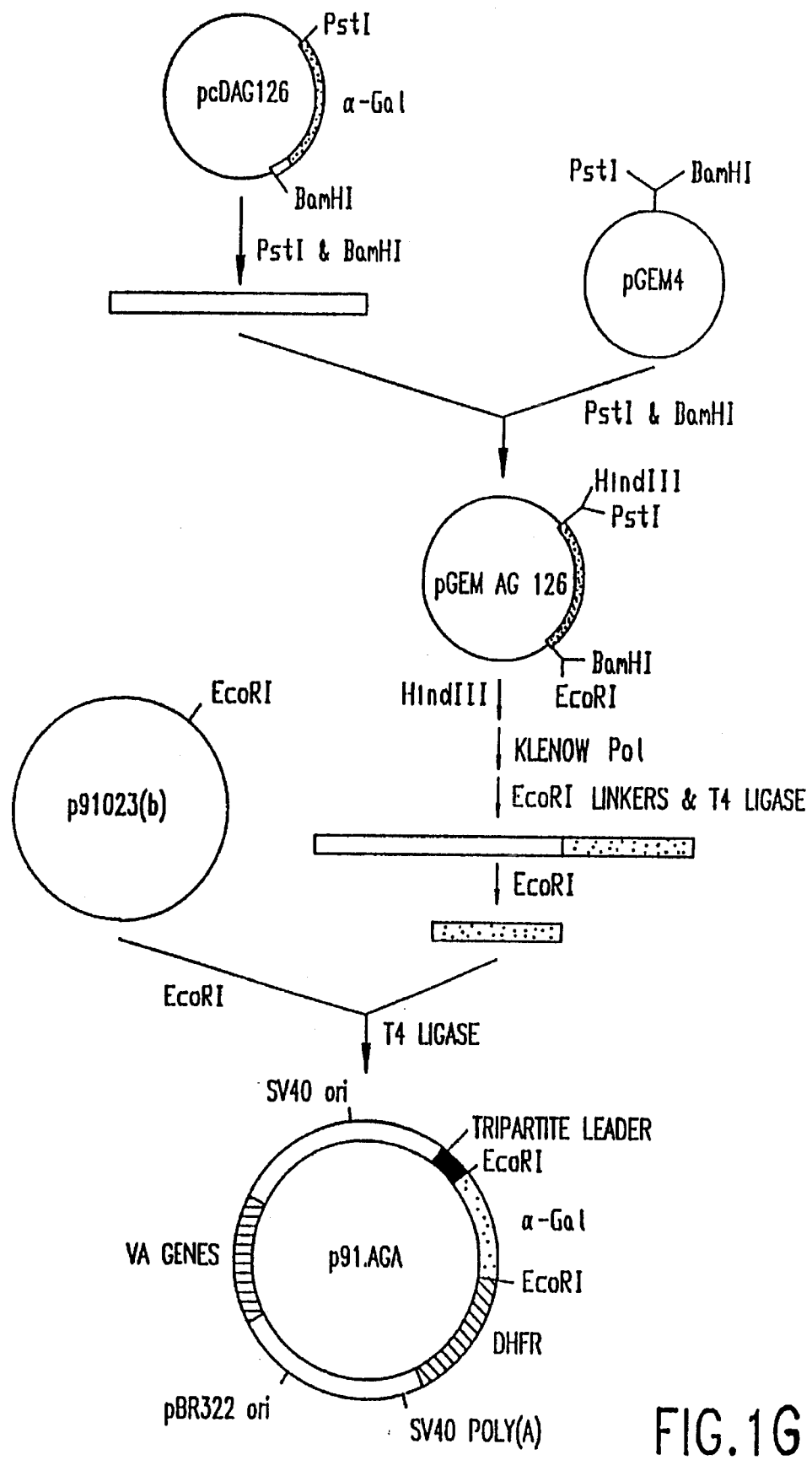

US005580757A

United States Patent [19]
Desnick et al.

[11] Patent Number: 5,580,757
[45] Date of Patent: Dec. 3, 1996

[54] CLONING AND EXPRESSION OF BIOLOGICALLY ACTIVE α-GALACTOSIDASE A AS A FUSION PROTEIN

[75] Inventors: Robert J. Desnick; David F. Bishop; Yiannis A. Ioannou, all of New York, N.Y.

[73] Assignee: The Mount Sinai School of Medicine of the City University of New York, New York, N.Y.

[21] Appl. No.: 261,577

[22] Filed: Jun. 17, 1994

Related U.S. Application Data

[60] Division of Ser. No. 983,451, Nov. 30, 1992, Pat. No. 5,401,650, which is a continuation-in-part of Ser. No. 602,824, Oct. 24, 1990, Pat. No. 5,356,804, and Ser. No. 602,608, Oct. 24, 1990, Pat. No. 5,382,524.

[51] Int. Cl.$^6$ .................... C12P 21/06; C12N 15/62; C12N 9/40
[52] U.S. Cl. .................. 435/69.7; 435/208; 435/320.1; 935/47
[58] Field of Search .................... 435/69.7, 208, 435/320.1; 935/47

[56] References Cited

U.S. PATENT DOCUMENTS

| | | | |
|---|---|---|---|
| 3,966,555 | 6/1976 | Arnaud et al. | 435/208 |
| 3,972,777 | 8/1976 | Yamada et al. | 435/208 |
| 4,450,238 | 5/1984 | Vitobello et al. | 435/255.2 |

FOREIGN PATENT DOCUMENTS

WO90/11353  10/1990  WIPO.

OTHER PUBLICATIONS

Bishop et al., 1985, Am. J. Hum Genetics 37 (4 Suppl) A 144.
Calhoun et al., 1985, Proc. Natl. Acad. Sci, USA 82: 7364–73698.
Bishop et al., 1986, Proc. Natl. Acad. Sci. USA 83: 4859–4863.
Hantzopoulos & Calhoun, 1987, Gene (Amst.) 57: 159–169.
Quinn et al., 1987, Gene (Amst.) 58: 177–188.
Tsuji et al., 1987, Eur. J. Biochem. 165(2): 275–280.
Bishop et al., 1988, Proc. Natl. Acad. Sci. USA 85: 3903–3907.
Bishop et al., 1988, in Lipid Storage Disorders, Eds. Salvayre et al., Plenum Publishing Corp., pp. 809–822.
Kornreich et al., 1989, Nuc. Acids Res. 17(8): 3301–3302.
Ioannou et al., Jun. 1990, in Inborn Errors of Metabolism, Vth International Congress, Abstract OC4.3.
Coppola et al., 1989, Biotechnology and Human Genetic Predisposition to Disease, J. Cell Biochem. Suppl., Abstract K306.
Brady et al., 1973, N. Engl. J. Med. 289(1): 9–14.
Desnick, et al. 1979, Proc. Natl. Acad. Sci. USA 76: 5326–5330.
Desnick et al., 1980, Birth Defects: Original Article Series, XVI(1): 393–413.
Bishop et al., 1981, in Lysosomes and Lysosmal Storage Diseases, Eds. Callahan et al., Raven Press, pp. 381–394.
Hasholt & Sorenson, 1986, Human Genet. 72: 72–76.
Lernansky et al., 1987, J. Biol. Chem. 262(5): 2062–2065.
Desnick et al., 1987, Enzyme 38: 54–64.
Bernstein, et al., 1989, J. Clin. Invest. 83: 1390–1399.
Kornreich, et al. 1990, J. Biol. Chem. 265(16): 9319–9326.
Bishop et al., 1980, Birth Defects: Original Article Series, XVI(1): 17–32.
Bishop & Desnick, 1981, J. Biol. Chem, 256(3): 1307–1316.
Dean, K. J. et al., 1977, Biochem. Biophys. Res. Commun. 77(4): 1411–1417.
Schram, A. W. et al., 1977, Biochimica et Biophysica Acta 482: 138–144.
Sweeley, C. C. et al., 1983, Archives of Biochemistry and Biophysics 223(1): 158–65.
Tsuji, S. et al., 1989, Biochem. Biophys. Res. Commun. 163(3): 1498–1504.
Yamauchi, T. et al., 1990, Biochem. Biophys. Res. Commun. 170(1): 231–237.
Wang, A. M, et al., 1990, J. Biol. Chem. 265(35): 21859–21866.
Wang, A. M. et al., 1988, Am. J. Hum. Genet. 43(3 Suppl.): A99.
Schindler, D. et al., Jun. 29, 1989, New Engl. J. Med. 320(26): 1735–1740.
Desnick, R. J. et al., 1989, in The Metabolic Basis of Inherited Disease, Scriver, C. R., et al., eds. Ch. 70 entitled "Fabry Disease: α–Galactosidase Deficiency; Schindler Disease: α–N–Acetylgalactosaminidase Deficiency":, pp. 1751–1796, McGraw Hill, New York.
Wang, A. M. et al., 1989, Am. J. Hum. Genet. 45(4 Suppl.): A228.
Wang, A. M. et al., 1990, J. Clin. Invest. 86: 1752–1756.
Desnick, R. J. and Wang, A. M., 1990, J. Inher. Metab. Dis. 13: 549–559.

(List continued on next page.)

*Primary Examiner*—Robert A. Wax
*Assistant Examiner*—Keith D. Hendricks
*Attorney, Agent, or Firm*—Pennie & Edmonds

[57] ABSTRACT

The present invention involves the production of large quantities of human α-Gal A by cloning and expressing the α-Gal A coding sequence in eukaryotic host cell expression systems. The eukaryotic expression systems, and in particular the mammalian host cell expression system described herein provide for the appropriate cotranslational and post-translational modifications required for proper processing, e.g., glycosylation, phosphorylation, etc. and sorting of the expression product so that an active enzyme is produced. In addition, the expression of fusion proteins which simplify purification is described.

Using the methods described herein, the recombinant α-Gal A is secreted by the engineered host cells so that it is recovered from the culture medium in good yield. The α-Gal A produced in accordance with the invention may be used, but is not limited to, in the treatment in Fabry Disease; for the hydrolysis of α-galactosyl residues in glycoconjugates; and/or for the conversion of the blood group B antigen on erythrocytes to the blood group O antigen.

15 Claims, 38 Drawing Sheets

OTHER PUBLICATIONS

Beutler, E. and Kuhl, W., 1972, J. Biol. Chem. 247(22): 7195–7200.

Callahan, J. W. et al., 1973, Biochemical Medicine 7: 424–431.

Kusiak, J. W. et al., 1978, J. Biol. Chem. 253(1): 184–190.

Dean, K. J. and Sweeley, C. C., 1979, J. Biol. Chem. 254(20): 10001–10005.

Bishop, D. F. et al., 1980, in Birth Defects: Original Article Series, XVI(1): 17–32 Desnick, R. J. et al., Editors Alan R. Liss, Inc., New York.

Weinstein et al., 1987, J. Biol. Chem. 262: 17735.

```
-60                                                    AGGTTA
    ATCT TAAAAGCCCA GGTTACCCGC GGAAATTTAT GCTGTCCGGT CACCGTGACA    -1

1 ATG CAG CTG AGG AAC CCA GAA CTA CAT CTG GGC TGC GCG CTT GCG
  1 Met Gln Leu Arg Asn Pro Glu Leu His Leu Gly Cys Ala Leu Ala

CTT CGC TTC CTG GCC CTC GTT TCC TGG GAC ATC CCT GGG GCT AGA     90
    Leu Arg Phe Leu Ala Leu Val Ser Trp Asp Ile Pro Gly Ala Arg     30

91 GCA CTG GAC AAT GGA TTG GCA AGG ACG CCT ACC ATG GGC TGG CTG
 31 Ala Leu Asp Asn Gly Leu Ala Arg Thr Pro Thr Met Gly Trp Leu
    N-Ter——————————————————————————————————————————————————

CAC TGG GAG CGC TTC ATG TGC AAC CTT GAC TGC CAG GAA GAG CCA    180
    His Trp Glu Arg Phe Met Cys Asn Leu Asp Cys Gln Glu Glu Pro     60
                                             Ser         Arg

181 GAT TCC TGC ATC AGT GAG AAG CTC TTC ATG GAG ATG GCA GAG CTC
 61 Asp Ser Cys Ile Ser Glu Lys Leu Phe Met Glu Met Ala Glu Leu
              X       X   Ser
    ————————————————————————

ATG GTC TCA GAA GGC TGG AAG GAT GCA GGT TAT GAG TAC CTC TGC    270
    Met Val Ser Glu Gly Trp Lys Asp Ala Gly Tyr Glu Tyr Leu Cys     90

271 ATT GAT GAC TGT TGG ATG GCT CCC CAA AGA GAT TCA GAA GGC AGA
 91 Ile Asp Asp Cys Trp Met Ala Pro Gln Arg Asp Ser Glu Gly Arg

CTT CAG GCA GAC CCT CAG CGC TTT CCT CAT GGG ATT CGC CAG CTA    360
    Leu Gln Ala Asp Pro Gln Arg Phe Pro His Gly Ile Arg Gln Leu    120

361 GCT AAT TAT GTT CAC AGC AAA GGA CTG AAG CTA GGG ATT TAT GCA
121 Ala Asn Tyr Val His Ser Lys Gly Leu Lys Leu Gly Ile Tyr Ala

GAT GTT GGA AAT AAA ACC TGC GCA GGC TTC CCT GGG AGT TTT GGA    450
    Asp Val Gly Asn Lys Thr Cys Ala Gly Phe Pro Gly Ser Phe Gly    150
                     CHO ———————

451 TAC TAC GAC ATT GAT GCC CAG ACC TTT GCT GAC TGG GGA GTA GAT
151 Tyr Tyr Asp Ile Asp Ala Gln Thr Phe Ala Asp Trp Gly Val Asp

CTG CTA AAA TTT GAT GGT TGT TAC TGT GAC AGT TTG GAA AAT TTG    540
    Leu Leu Lys Phe Asp Gly Cys Tyr Cys Asp Ser Leu Glu Asn Leu    180
```

FIG.1A

```
541  GCA GAT GGT TAT AAG CAC ATG TCC TTG GCC CTG AAT AGG ACT GGC
181  Ala Asp Gly Tyr Lys His Met Ser Leu Ala Leu Asn Arg Thr Gly
                                                    CHO -------

AGA AGC ATT GTG TAC TCC TGT GAG TGG CCT CTT TAT ATG TGG CCC  630
     Arg Ser Ile Val Tyr Ser Cys Glu Trp Pro Leu Tyr Met Trp Pro  210

631  TTT CAA AAG CCC AAT TAT ACA GAA ATC CGA CAG TAC TGC AAT CAC
211  Phe Gln Lys Pro Asn Tyr Thr Glu Ile Arg Gln Tyr Cys Asn His
                     CHO -------

TGG CGA AAT TTT GCT GAC ATT GAT GAT TCC TGG AAA AGT ATA AAG  720
     Trp Arg Asn Phe Ala Asp Ile Asp Asp Ser Trp Lys Ser Ile Lys  240
                                 Asn         X
         T-49────────────────────────────────────────
```

```
721  AGT ATC TTG GAC TGG ACA TCT TTT AAC CAG GAG AGA ATT GTT GAT
241  Ser Ile Leu Asp Trp Thr Ser Phe Asn Gln Glu Arg Ile Val Asp

GTT GCT GGA CCA GGG GGT TGG AAT GAC CCA GAT ATG TTA GTG ATT  810
     Val Ala Gly Pro Gly Gly Trp Asn Asp Pro Asp Met Leu Val Ile  270

811  GGC AAC TTT GGC CTC AGC TGG AAT CAG CAA GTA ACT CAG ATG GCC
271  Gly Asn Phe Gly Leu Ser Trp Asn Gln Gln Val Thr Gln Met Ala

CTC TGG GCT ATC ATG GCT GCT CCT TTA TTC ATG TCT AAT GAC CTC  900
     Leu Trp Ala Ile Met Ala Ala Pro Leu Phe Met Ser Asn Asp Leu  300
                                                  CB-1─────────

901  CGA CAC ATC AGC CCT CAA GCC AAA GCT CTC CTT CAG GAT AAG GAC
301  Arg His Ile Ser Pro Gln Ala Lys Ala Leu Leu Gln Asp Lys Asp
                     X                              X
     ──────────────────────────────────────────────────────────
                            T-53B ────────

GTA ATT GCC ATC AAT CAG GAC CCC TTG GGC AAG CAA GGG TAC CAG  990
     Val Ile Ala Ile Asn Gln Asp Pro Leu Gly Lys Gln Gly Tyr Gln  330
     Arg             Glu
     ──────────────────────────────────────────────────────────
```

FIG. 1B

```
 991  CTT AGA CAG GGA GAC AAC TTT GAA GTG TGG GAA CGA CCT CTC TCA
 331  Leu Arg Gln Gly Asp Asn Phe Glu Val Trp Glu Arg Pro Leu Ser
              Leu                         Gly Ser Lys      X
       T-88

GGC TTA GCC TGG GCT GTA GCT ATG ATA AAC CGG CAG GAG ATT GGT  1080
      Gly Leu Ala Trp Ala Val Ala Met Ile Asn Arg Gln Glu Ile Gly   360

1081  GGA CCT CGC TCT TAT ACC ATC GCA GTT GCT TCC CTG GGT AAA GGA
 361  Gly Pro Arg Ser Tyr Thr Ile Ala Val Ala Ser Leu Gly Lys Gly

GTG GCC TGT AAT CCT GCC TGC TTC ATC ACA CAG CTC CTC CCT GTG  1170
      Val Ala Cys Asn Pro Ala Cys Phe Ile Thr Gln Leu Leu Pro Val   390

1171  AAA AGG AAG CTA GGG TTC TAT GAA TGG ACT TCA AGG TTA AGA AGT
 391  Lys Arg Lys Leu Gly Phe Tyr Glu Trp Thr Ser Arg Leu Arg Ser
       T-51
         T-53A

CAC ATA AAT CCC ACA GGC ACT GTT TTG CTT CAG CTA GAA AAT ACA  1260
      His Ile Asn Pro Thr Gly Thr Val Leu Leu Gln Leu Glu Asn Thr   420
                       CHO

1261  ATG CAG ATG TCA TTA AAA GAC TTA CTT TAA AAAAAAAAAA AAAAAAAAA
 421  Met Gln Met Ser Leu Lys Asp Leu Leu Ter                       429

AAAAAAAAAA AAAAAAAAAA AAA                                    1333
```

FIG.1C

FIG. 1D

```
                                                                                                    CONT.
                                                                                                    ON
                                                                                                    FIG.1E
                                                                             1;2
Gal B:   1                                     LDNGL LQTPP MGVLA WERFR CNINC DEDPK NCISE QLFMEMADRMAQ
Gal A:   1                                     ..LDNGL ..ARTPT MGVLH WERFM CNLDC QEEPD SCISE KLFMEMAELMVS
Mel 1:   1                                     SYNGL GLTPQ MGWDN WNTF       A    CD    ..VSEQ LLDTADRISD
                                               ⌒3⌒

Gal B:  18                                     GIYAD MGNFT CMGYP GTTLD KVVQ DAQTF AEWK LDGCF STPE
Gal A:  32                                     GIYAD VGNKT CAGFP G..SF GYYD IDAQT FAD.. VG VDLLK FDGCY CDSL
Mel 1:  19                                     GMYSS AGEYT CAGYP G..   SLGREE EDAQ FFANNR VDYLKY DNCYNKGQ
                                               ⌒2⌒                                 ⌒2⌒
                                                                                            5;6
Gal B: 117                                     DDIQD SVWSV LSILN VFVEH QDILQ PVAGP GHVND PDMLLIGNFGLS
Gal A: 132                                     ADIDD SVKSI LDVTS FNQER IVD.. VAGP G..   WNDPDM..VIGNFGLS
Mel 1: 108                                     DSCPD GYYAG FSIMN ILNKAAPMGQ NAGVG GW**  WNDLDN LEVGVGNLT
                                               ⌒1;2;3⌒                               119

Gal B: 216                                     RIHKIE KSLIE VYMRPLS NKASA LVFFSCRT DMPYR YHSSLGQLN
                                               6;7
Gal A: 230                                     YQLR QGDNFE VVWE**  RPLS GLAWA VAMINRQEIGG PRSYTIAVASLGK
Mel 1: 205                                     IRVS DTDEYGE IWSGPLDNGDQ   ..VVALLNGGSVSRPMNTTLE;;D SLGK
                                               ⌒14⌒                                                 ⌒1⌒
                                                                                                    ⌒1;2⌒
```

FIG. 1E

CONT. ON FIG. 1F

```
DGWRDMGYTYLNIDDCWIGG
.EGVKDAGYEYLCIDDCWMAPQ
.LGLKDMGYKYIILDDCWSSG

314
ER  AQIGYPKMAAALNATGRPI
..  ENLADGYKHMSLALNRTGRSI
FGTPESYRKMSDALNKTGRPI
         1111

LEQRSRAQMALWTVLAAPLLM
..   VTQMALWAIMAAPLFM
WNQQ                    340 PSVI
DDEEK AHFSMVAMVKSPLII

FTGSVIYEAQDVYSGDIIS
GVACNPACFITQLL PVKRKL
KLTSTDDLWANRVTASIGRKT
                  3       111
                              1
```

CONT. FROM FIG. 1D

FIG. 1F

```
1191  GAA TGG ACT TCA AGG TTA AGA AGT CAC ATA AAT CCC ACA GGA ACT
 398  Glu Trp Thr Ser Arg Leu Arg Ser His Ile Asn Pro Thr Gly Thr

1226  GTT TTG CTT CAG CTA GAA AAT ACA ATG CAG ATG TCA TTA AAA GAC
 413  Val Leu Leu Gln Leu Glu Asn Thr Met Gln Met Ser Leu Lys Asp
```

Collagenase cleavage
                           |
```
1271  TTA CTT CCG GCT GGT CCG GCG CAA CAC GAT GAA GCT CAA CAA AAT
 428  Leu Leu Pro Ala Gly Pro Ala Gln His Asp Glu Ala Gln Gln Asn
```

α-Gal A              IgG Binding domain E

```
1316  GCT TTT TAT CAA GTC TTA AAT ATG CCT AAC TTA AAT GCT GAT CAA
 443  Ala Phe Tyr Gln Val Leu Asn Met Pro Asn Leu Asn Ala Asp Gln

1371  CGC AAT GGT TTT ATC CAA AGC CTT AAA GAT GAT CCA AGC CAA AGT
 458  Arg Asn Gly Phe Ile Gln Ser Leu Lys Asp Asp Pro Ser Gln Ser

1416  GCT AAC GTT TTA GGT GAA GCT CAA AAA CTT AAT GAC TCT CAA GCT
 473  Ala Asn Val Leu Gly Glu Ala Gln Lys Leu Asn Asp Ser Gln Ala
```

Bam HI  Eco RI
```
1501  CCA AAA TAA GGATCCCGGAATTCGGCC
 488  Pro Lys Ter
```

FIG. 23

CLONING AND EXPRESSION OF BIOLOGICALLY ACTIVE α-GALACTOSIDASE A AS A FUSION PROTEIN

This is a Divisional of Ser. No. 07/983,451, filed Nov. 30, 1992 now U.S. Pat. No. 5,401,650, which is a Continuation-In-Part of Ser. No. 07/602,824 filed Oct. 24, 1990 now U.S. Pat. No. 5,356,804, and Ser. No. 07/602,608 filed Oct. 24, 1990 now U.S. Pat. No 5,382,524, each of which is incorporated by reference herein in its entirety.

TABLE OF CONTENTS

1. Introduction
2. Background Of The Invention
 2.1. α-GAL A And Fabry Disease
 2.2. The α-Gal A Enzyme
 2.3. Lysosomal Enzymes: Biosynthesis And Targeting
3. Summary Of The Invention
 3.1. Definitions
4. Description Of The Figures
5. Detailed Description Of The Invention
 5.1. The α-GAL A Coding Sequence
 5.2. Production Of Recombinant α-Gal A
  5.2.1.. Construction Of Expression Vectors And Preparation of Transfectants
  5.2.2. Identification Of Transfectants Or Transformants Expressing The α-Gal A Product
  5.2.3. Purification Of The α-GAL A Gene Product
  5.2.4. Characterization Of The Recombinant Enzyme
  5.2.5. Modified Glycoforms Of Recombinant α-Gal A For Enzyme Therapy In Fabry Disease
 5.3. Uses Of The Recombinant α-Gal A
  5.3.1. α-Gal A Enzyme Therapy In Fabry Disease
  5.3.2. In Vitro Uses Of α-Gal A
6. Example: Overexpression And Specific Secretion Of Biologically Active α-Galactosidase A In A Mammalian Cell System
 6.1. Materials And Methods
  6.1.1. Materials
  6.1.2. Construction Of Expression Vector p91-AGA
  6.1.3. Cell Culture, Electrotransfection, And Gene Amplication
  6.1.4. Enzyme And Protein Assays
 6.2. Results
  6.2.1. Expression Of Human α-Gal A In COS-1 Cells
  6.2.2. Transfection And Amplification Of α-Gal A In dhfr$^-$ CHO Cells
  6.2.3. High Level Expression Clones Secrete Human α-Gal A
  6.2.4. Specific Secretion Of Over-Expressed Lysosomal Enzymes
  6.2.5. Effect Of Serum Concentration On Secretion
  6.2.6. Production In Bioreactors
 6.3. Discussion
7. Example: Purification, Characterization And Processing Of Recombinant α-Galactosidase A
 7.1. Materials And Methods
  7.1.1. Materials
  7.1.2. Cell Culture
  7.1.3. Purification Of Recombinant α-Gal A
  7.1.4. Enzyme And Protein Assays
  7.1.5. In Vivo Natural Substrate Assay
  7.1.6. Polyclonal Antibodies
  7.1.7. SDS-Page And Autoradiography
  7.1.8. Isoelectric Point And pH Optimum Determination
  7.1.9. Mannose-6-Phosphate Receptor Affinity Chromatography And QAE Sephadex Chromatography
  7.1.10. Labeling Of Cells With [$^{35}$S]-Methionine, [$^{3}$H]-Mannose And [$^{32}$P]-Phosphorous
  7.1.11. Cell Lysis And Immunoprecipitation
 7.2. Results
  7.2.1. Purification
  7.2.2. Physicokinetic Properties
  7.2.3. Processing And Rate of Secretion Of Recombinant α-Gal A
  7.2.4. Analysis Of Carbohydrate Moieties On Recombinant α-Gal A
  7.2.5. Phosporylation
  7.2.6. Analysis Of Endo H Sensitive Oligosaccharides
  7.2.7. Interaction Of α-Gal A With The Mannose-6-Phosphate Receptor
  7.2.8. Receptor Mediated Uptake Of Recombinant α-Gal A In Fabry Fibroblasts
8. Example: α-Gal A-Protein A Fusion Expressed In Mammalian Cells
 8.1. Materials And Methods
  8.1.1. Materials
  8.1.2. Cell Culture And Transfections
  8.1.3. PCR, DNA Sequencing And Vector Constructions
 8.2. Results
  8.2.1. Construction Of α-Gal A-Protein A (AGA-PA) Fusion
  8.2.2. Expression Of pAGA-PA In COS-1 Cells
  8.2.3. Affinity Purification Of α-Gal A
9. Example: In Vivo Modification Of Recombinant Human α-Gal A Glycosylation By α2,6-Sialyltransferase
 9.1. Materials And Methods
  9.1.1. Construction Of The α2,6-Sialyltransferase Expression Vector, pST26
  9.1.2. SNA-Lectin Fluorescence Microscopy
  9.1.3. Purification Of Radiolabelled Human α-GAL A With And Without α2,6-Sialic Acid Residues
  9.1.4. In Vivo Half-Life And Tissue Distribution Of Recombinant α-GAL A
 9.2. Results
  9.2.1. Introduction Of PST26 Into DG5.3-1000Mx CHO Cells And Demonstration Of α2,6-Sialyltransferase Activity In G418-Selected Clones
  9.2.2. Characterization Of Recombinant Human Secreted α2,6-Sialylated α-GAL A
  9.2.3. Plasma Half-Life And Tissue Distribution Of α2,6-Sialylated Human α-GAL A In Mice
10. Example: Overexpression Of Human Lysosomal Proteins Results In Their Intracellular Aggregation, Crystallization In Lysosomes, And Selective Secretion
 10.1. Materials And Methods
  10.1.1. Construction Of Plasmids For Lysosomal Enzyme Overproduction
  10.1.2. Cell Culture, Electrotransfection, And Gene Amplification
  10.1.3. Ultrastructural And Immunolabeling Studies
  10.1.4. SDS-Page And Autoradiography
  10.1.5. In Vitro Studies Of α-GAL A Aggregation
  10.1.6. Enzyme And Protein Assays
 10.2. Results
  10.2.1. Overexpression Results In Crystalline Structures Containing Human α-GAL A In Membrane-Limited Vesicles 10.2.2. α-GAL A And α-N-Acetylgalactosaminidase Aggregate At High Concentration And Low pH
10.3. Discussion
11. Deposit Of Microorganisms

1. INTRODUCTION

The present invention relates to the production of biologically active human α-Galactosidase (α-Gal A) involving cloning and expression of the genetic coding sequence for α-Gal A in eukaryotic expression systems which provide for proper post-translational modifications and processing of the expression product.

The invention is demonstrated herein by working examples in which high levels of α-Gal A were produced in mammalian expression systems. The α-Gal enzyme produced in accordance with the invention may be used for a variety of purposes, including but not limited to enzyme replacement therapy for Fabry Disease, industrial processes involving the hydrolysis of α-D-galactosyl residues of glycoconjugates, and for the conversion of the blood group B antigen on erythrocytes to the blood group O antigen.

2. BACKGROUND OF THE INVENTION

In the early 1970's, several investigators demonstrated the existence of two α-Galactosidase isozymes designated A and B, which hydrolyzed the α-galactosidic linkages in 4-MU-and/or p-NP-α-D-galactopyranosides (Kint, 1971, Arch. Int. Physiol. Biochem. 79: 633–644; Beutler & Kuhl, 1992, Amer. J. Hum. Genet. 24: 237–249; Romeo, et al., 1992, FEBS Lett. 27: 161–166; Wood & Nadler, 1992, Am. J. Hum. Genet. 24: 250–255; Ho, et al., 1992, Am. J. Hum. Genet. 24: 256–266; Desnick, et al., 1973, J. Lab. Clin. 81: 157–171; and Desnick, et al., 1989, in The Metabolic Basis of Inherited Disease, Scriver, C. R., Beaudet, A. L. Sly, W. S. and Valle, D., eds, pp. 1751–1796, McGraw Hill, New York). In tissues, about 80%–90% of total α-Galactosidase (α-Gal) activity was due to a thermolabile, myoinositol-inhibitable α-Gal A isozyme, while a relatively thermostable, α-Gal B, accounted for the remainder. The two "isozymes" were separable by electrophoresis, isoelectric focusing, and ion exchange chromatography. After neuraminidase treatment, the electrophoretic migrations and pI value of α-Gal A and B were similar (Kint, 1971; Arch. Int. Physiol. Biochem. 79: 633–644), initially suggesting that the two enzymes were the differentially glycosylated products of the same gene. The finding that the purified glycoprotein enzymes had similar physical properties including subunit molecular weight (~46 kDa), homodimeric structures, and amino acid compositions also indicated their structural relatedness (Beutler & Kuhl, 1972, J. Biol. Chem. 247: 7195–7200; Callahan, et al., 1973, Biochem. Med. 7: 424–431; Dean, et al., 1977, Biochem. Biophys. Res. Comm. 77: 1411–1417; Schram, et al., 1977, Biochim. Biophys. Acta. 482: 138–144; Kusiak, et al., 1978, J. Biol. Chem. 253: 184–190; Dean, et al., 1979, J. Biol. Chem. 254: 10001–10005; and Bishop, et al., 1980, in Enzyme Therapy in Genetic Disease: 2, Desnick, R. J., ed., pp. 17–32, Alan R. Liss, Inc., New York). However, the subsequent demonstration that polyclonal antibodies against α-Gal A or B did not cross-react with the other enzyme (Beutler & Kuhl, 1972, J. Biol. Chem. 247: 7195–7200; and Schram, et al., 1977, Biochim. Biophys. Acta. 482: 138–144); that only α-Gal A activity was deficient in hemizygotes with Fabry disease (Kint, 1971; Arch. Int. Physiol. Biochem. 79: 633–644; Beutler & Kuhl, 1972, Amer. J. Hum. Genet. 24: 237–249; Romeo, et al., 1972, FEBS Lett. 27: 161–166; Wood & Nadler, 1972, Am. J. Hum. Genet. 24: 250–255; Ho, et al., 1972, Am. J. Hum. Genet. 24: 256–266; Desnick, et al., 1973, J. Lab. Clin. Med. 81: 157–171; Desnick, et al., 1989, in The Metabolic Basis of Inherited Disease, Scriver, C. R., Beaudet, A. L. Sly, W. S. and Valle, D., eds, pp. 1751–1796, McGraw Hill, New York; and Beutler & Kuhl, 1972, J. Biol. Chem. 247: 7195–7200); and that the genes for α-Gal A and B mapped to different chromosomes (Desnick, et al., 1989, in The Metabolic Basis of Inherited Disease, Scriver, C. R., Beaudet, A. L. Sly, W. S. and Valle, D., eds, pp. 1751–1796, McGraw Hill, New York; deGroot, et al., 1978, Hum. Genet. 44: 305–312), clearly demonstrated that these enzymes were genetically distinct.

2.1. α-GAL A AND FABRY DISEASE

In Fabry disease, a lysosomal storage disease resulting from the deficient activity of α-Gal A, identification of the enzymatic defect in 1967 (Brady, et al., 1967, N. Eng. J. Med. 276: 1163) led to the first in vitro (Dawson, et al., 1973, Pediat. Res. 7: 694–690m) and in vivo (Mapes, et al., 1970, Science 169: 987) therapeutic trials of α-Gal A replacement in 1969 and 1970, respectively. These and subsequent trials (Mapes, et al., 1970, Science 169: 987; Desnick, et al., 1979, Proc. Natl. Acad. Sci. U.S.A. 76: 5326; and, Brady, et al., 1973, N. Engl. J. Med. 289: 9) demonstrated the biochemical effectiveness of direct enzyme replacement for this disease. Repeated injections of purified splenic and plasma α-Gal A (100,000 U/injection) were administered to affected hemizygotes over a four month period (Desnick, et al., 1979, Proc. Natl. Acad. Sci. U.S.A. 76: 5326). The results of these studies demonstrated that (a) the plasma clearance of the splenic form was 7 times faster than that of the plasma form (10 min vs 70 min); (b) compared to the splenic form of the enzyme, the plasma form effected a 25-fold greater depletion of plasma substrate over a markedly longer period (48 hours vs 1 hour); (c) there was no evidence of an immunologic response to six doses of either form, administered intravenously over a four month period to two affected hemizygotes; and (d) suggestive evidence was obtained indicating that stored tissue substrate was mobilized into the circulation following depletion by the plasma form, but not by the splenic form of the enzyme. Thus, the administered enzyme not only depleted the substrate from the circulation (a major site of accumulation), but also possibly mobilized the previously stored substrate from other depots into the circulation for subsequent clearance. These studies indicated the potential for eliminating, or significantly reducing, the pathological glycolipid storage by repeated enzyme replacement.

However, the biochemical and clinical effectiveness of enzyme replacement in Fabry disease has not been demonstrated due to the lack of sufficient human enzyme for adequate doses and long-term evaluation.

2.2. THE α-Gal A ENZYME

The α-Gal A human enzyme has a molecular weight of approximately 101,000 Da. On SDS gel electrophoresis it migrates as a single band of approximately 49,000 Da indicating the enzyme is a homodimer (Bishop & Desnick, 1981, J. Biol. Chem. 256: 1307). α-Gal A is synthesized as a 50,500 Da precursor containing phosphorylated endoglycosidase H sensitive oligosaccharides. This precursor is processed to a mature form of about 46,000 Da within 3–7 days after its synthesis. The intermediates of this processing have not been defined (Lemansky, et al., 1987, J. Biol. Chem. 262: 2062). As with many lysosomal enzymes, α-Gal A is targeted to the lysosome via the mannose-6-phosphate receptor. This is evidenced by the high secretion rate of this enzyme in mucolipidosis II cells and in fibroblasts treated with NH₄Cl.

The enzyme has been shown to contain 5–15% Asn linked carbohydrate (Ledonne, et al., 1983, Arch. Biochem. Biophys. 224: 186). The tissue form of this enzyme was shown to have ~52% high mannose and 48% complex type oligosaccharides. The high mannose type coeluted, on Bio-gel chromatography, with $Man_{8-9}GlcNAc$ while the complex type oligosaccharides were of two categories containing 14 and 19–39 glucose units. Upon isoelectric focusing many forms of this enzyme are observed depending on the sources of the purified enzyme (tissue vs plasma form). However, upon treatment with neuraminidase, a single band is observed (pI~5.1) indicating that this heterogeneity is due to different degrees of sialylation (Bishop & Desnick, 1981, J. Biol. Chem. 256: 1307). Initial efforts to express the full-length cDNA encoding α-Gal A involved using various prokaryotic expression vectors (Hantzopoulos and Calhoun, 1987, Gene 57:159; Ioannou, 1990, Ph.D. Thesis, City University of New York). Although microbial expression was achieved, as evidenced by enzyme assays of intact *E. coli* cells and growth on melibiose as the carbon source, the human protein was expressed at low levels and could not be purified from the bacteria. These results indicate that the recombinant enzyme was unstable due to the lack of normal glycosylation and/or the presence of endogenous cytoplasmic or periplasmic proteases.

2.3. LYSOSOMAL ENZYMES: BIOSYNTHESIS AND TARGETING

Lysosomal enzymes are synthesized on membrane-bound polysomes in the rough endoplasmic reticulum. Each protein is synthesized as a larger precursor containing a hydrophobic amino terminal signal peptide. This peptide interacts with a signal recognition particle, an 11S ribonucleoprotein, and thereby initiates the vectoral transport of the nascent protein across the endoplasmic reticulum membrane into the lumen (Erickson, et al., 1981, J. Biol. Chem. 256: 11224; Erickson, et al., 1983, Biochem. Biophys. Res. Commun. 115: 275; Rosenfeld, et al., 1982, J. Cell Biol. 93: 135). Lysosomal enzymes are cotranslationaly glycosylated by the en bloc transfer of a large preformed oligosaccharide, glucose-3, mannose-9, N-acetylglucosamine-2, from a lipid-linked intermediate to the Asn residue of a consensus sequence Asn-X-Ser/Thr in the nascent polypeptide (Kornfeld, R. & Kornfeld, S., 1985, Annu. Rev. Biochem. 54: 631). In the endoplasmic reticulum, the signal peptide is cleaved, and the processing of the Asn-linked oligosaccharide begins by the excision of three glucose residues and one mannose from the oligosaccharide chain.

The proteins move via vesicular transport, to the Golgi stack where they undergo a variety of posttranslational modifications, and are sorted for proper targeting to specific destinations: lysosomes, secretion, plasma membrane. During movement through the Golgi, the oligosaccharide chain on secretory and membrane glycoproteins is processed to the sialic acid-containing complex-type. While some of the oligosaccharide chains on lysosomal enzymes undergo similar processing, most undergo a different series of modifications. The most important modification is the acquisition of phosphomannosyl residues which serve as an essential component in the process of targeting these enzymes to the lysosome (Kaplan, et al., 1977, Proc. Natl. Acad. Sci. U.S.A. 74: 2026). This recognition marker is generated by the sequential action of two Golgi enzymes. First, N-acetylglucosaminylphosphotransferase transfers N-acetylglucosamine-1-phosphate from the nucleotide sugar uridine diphosphate-N-acetylglucosamine to selected mannose residues on lysosomal enzymes to give rise to a phosphodiester intermediate (Reitman & Kornfeld, 1981, J. Biol. Chem. 256: 4275; Waheed, et al., 1982, J. Biol. Chem. 257: 12322). Then, N-acetylglucosamine-1-phosphodiester α-N-acetylglucosaminidase removes N-acetylglucosamine residue to expose the recognition signal, mannose-6-phosphate (Varki & Kornfeld, 1981, J. Biol. Chem. 256: 9937; Waheed, et al., 1981, J. Biol. Chem. 256: 5717).

Following the generation of the phosphomannosyl residues, the lysosomal enzymes bind to mannose-6-phosphate (M-6-P) receptors in the Golgi. In this way the lysosomal enzymes remain intracellular and segregate from the proteins which are destined for secretion. The ligand-receptor complex then exits the Golgi via a coated vesicle and is delivered to a prelysosomal staging area where dissociation of the ligand occurs by acidification of the compartment (Gonzalez-Noriega, et al., 1980, J. Cell Biol. 85: 839). The receptor recycles back to the Golgi while the lysosomal enzymes are packaged into vesicles to form primary lysosomes. Approximately, 5–20% of the lysosmol enzymes do not traffic to the lysosomes and are secreted presumably, by default. A portion of these secreted enzymes may be recaptured by the M-6-P receptor found on the cell surface and be internalized and delivered to the lysosomes (Willingham, et al., 1981, Proc. Natl. Acad. Sci. U.S.A. 78: 6967).

Two mannose-6-phosphate receptors have been identified. A 215 kDa glycoprotein has been purified from a variety of tissues (Sahagian, et al., 1981, Proc. Natl. Acad. Sci. U.S.A., 78: 4289; Steiner & Rome, 1982, Arch. Biochem. Biophys. 214: 681). The binding of this receptor is divalent cation independent. A second M-6-P receptor also has been isolated which differs from the 215 kd receptor in that it has a requirement for divalent cations. Therefore, this receptor is called the cation-dependent ($M-6-P^{CD}$) while the 215 kd one is called cation-independent ($M-6-P^{CI}$). The $M-6-P^{CD}$ receptor appears to be an oligomer with three subunits with a subunit molecular weight of 46 kDa.

3. SUMMARY OF THE INVENTION

The present invention involves the production of large quantities of human α-Gal A by cloning and expressing the α-Gal A coding sequence in eukaryotic host cell expression systems. The eukaryotic expression systems, and in particular the mammalian host cell expression system described herein, provide for the appropriate cotranslational and post-translational modifications required for proper processing, e.g., glycosylation, sialylation, phosphorylation, etc. and sorting of the expression product so that an active enzyme is produced. Also described is the expression of α-galactosidase A fusion proteins which are readily purified. These fusion proteins are engineered so that the α-galactosidase A moiety is readily cleaved from the fusion protein and recovered.

Using the methods described herein, the recombinant α-Gal A is secreted by the engineered host cells so that it is recovered from the culture medium in good yield. The α-Gal A produced in accordance with the invention may be used for a variety of ends, including but not limited to the treatment in Fabry Disease, the conversion of blood type B to O, or in any commercial process that involves the hydrolysis of α-D-galactosyl residues from glycoconjugates.

Further, this invention describes a method whereby proteins that are normally intracellularly targeted may be overexpressed and secreted from recombinant mammalian cell lines.

3.1. DEFINITIONS

As used herein, the following terms and abbreviations will have the indicated meaning:

| | |
|---|---|
| α-Galactosidase A | α-Gal A |
| α-N-AcetylGalactosaminidase | α-GalNAc |
| base pair(s) | bp |
| Chinese hamster ovary | CHO |
| complementary DNA | cDNA |
| counts per minute | cpm |
| deoxyribonucleic acid | DNA |
| Dulbecco's Modified Eagle's Medium | DMEM |
| fetal calf serum | FCS |
| kilobase pairs | kb |
| kilodalton | kDa |
| mannose-6-phosphate | M-6-P |
| methotrexate | MTX |
| 4-methylumbelliferyl-α-D--galactoside | 4-MU-α-Gal |
| 4-methyl-umbelliferyl-α-N-acetyl-galactosaminide | 4-Mu-α-GalNAc |
| micrograms | μg |
| micrometer | μm |
| nanograms | ng |
| nanometer | nm |
| nucleotide | nt |
| p-nitrophenyl-α-N-Acetylgalactosaminide | pNP-α-GalNAc |
| polyacrylamide gel electrophoresis | PAGE |
| polymerase chain reaction | PCR |
| ribonucleic acid | RNA |
| sodium dodecyl sulfate | SDS |
| units | U |

4. DESCRIPTION OF THE FIGURES

Figure 1F:
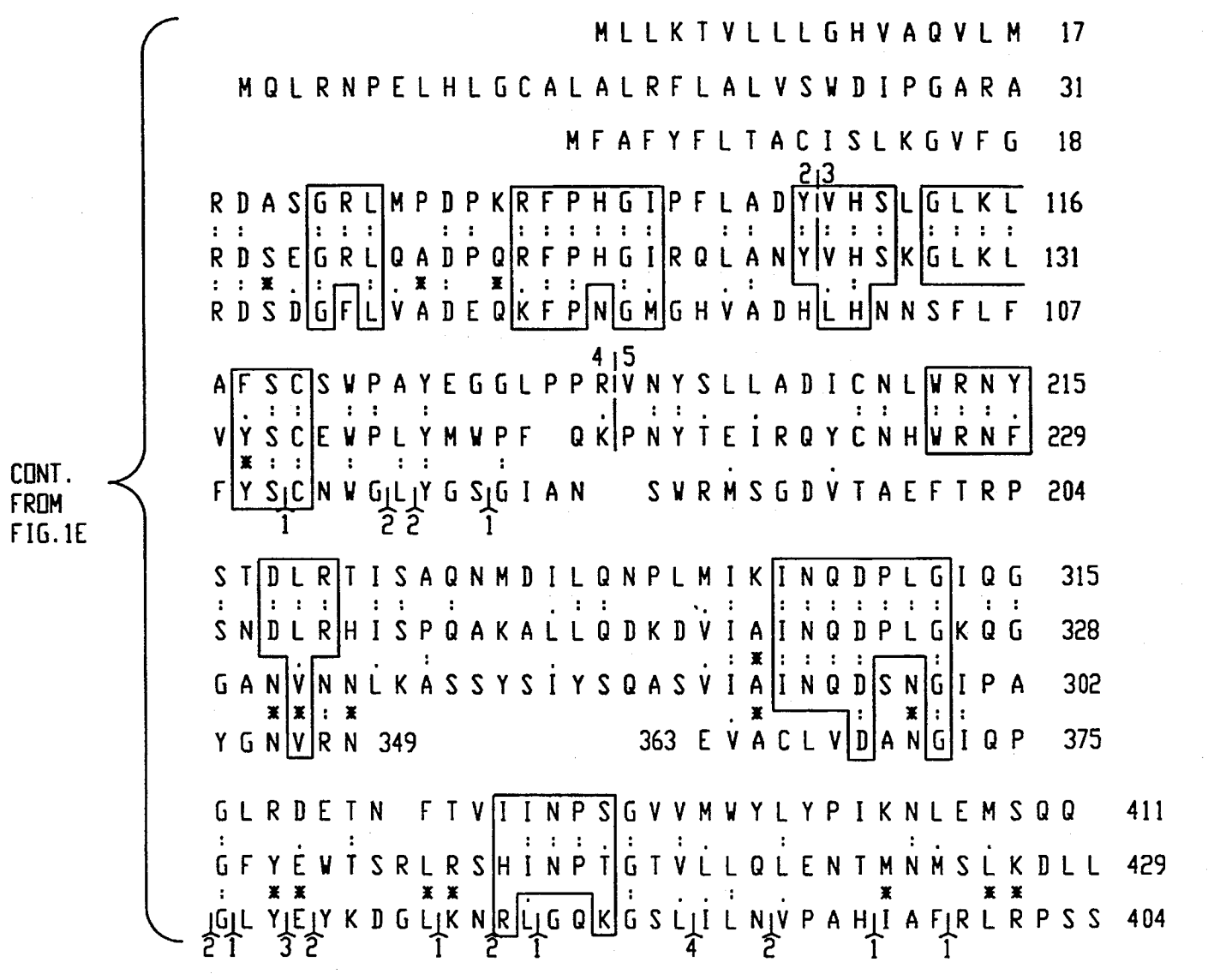

FIGS. 1A–1C. Full-length human α-Gal cDNA sequence (SEQ ID NO:6). N-terminal, cyanogen bromide (CB), and tryptic (T) peptide amino acid sequences (SEQ ID NO:7) obtained from peptide microsequencing are indicated by underlines. Differences from the sequence predicted from the cDNA are shown. The four putative N-glycosylation sites are denoted and the 3' termination signals are overlined.

FIGS. 1D–1F. Alignment of amino acid sequences deduced from the full-length cDNAs encoding human α-Gal-NAc (α-Gal B), α-Gal (SEQ ID NO:9), yeast Mel 1 (SEQ ID NO:10), and E. coli Mel A. Colons, identical residues; single dots, isofunctional amino acids; and boxes, identical residues in α-GalNAc, α-Gal, Mel 1 and/or Mel A. Gaps were introduced for optimal alignment. Numbered vertical lines indicate exon boundaries for α-Gal (Bishop, et al, 1988, Proc. Natl. Acad. Sci. U.S.A. 85: 3903–3907).

FIG. 1E. Construction of the α-Gal mammalian expression vector p91-AGA. The full-length cDNA was excised from plasmid pcDAG126, adapted by the addition of Eco RI linkers and subsequently cloned into the Eco RI site of expression vector p91023(B).

Figure 2A:
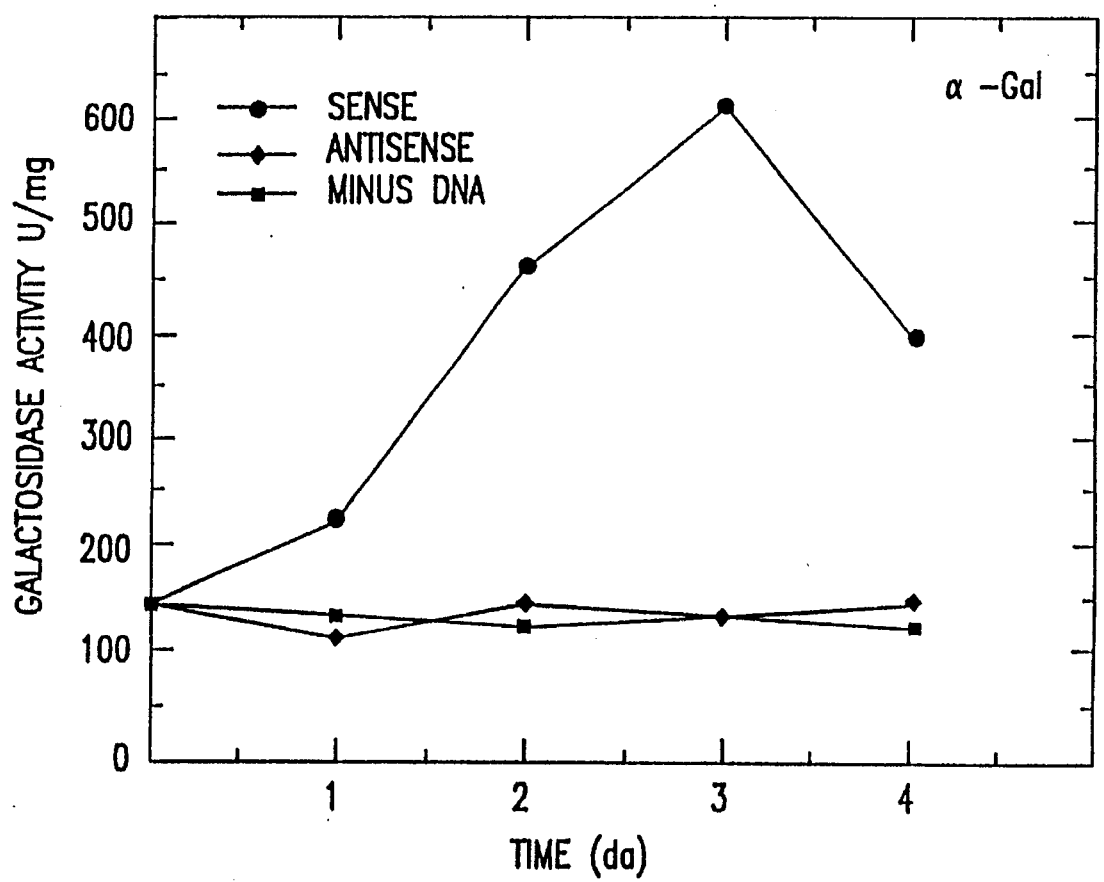
Figure 2B:
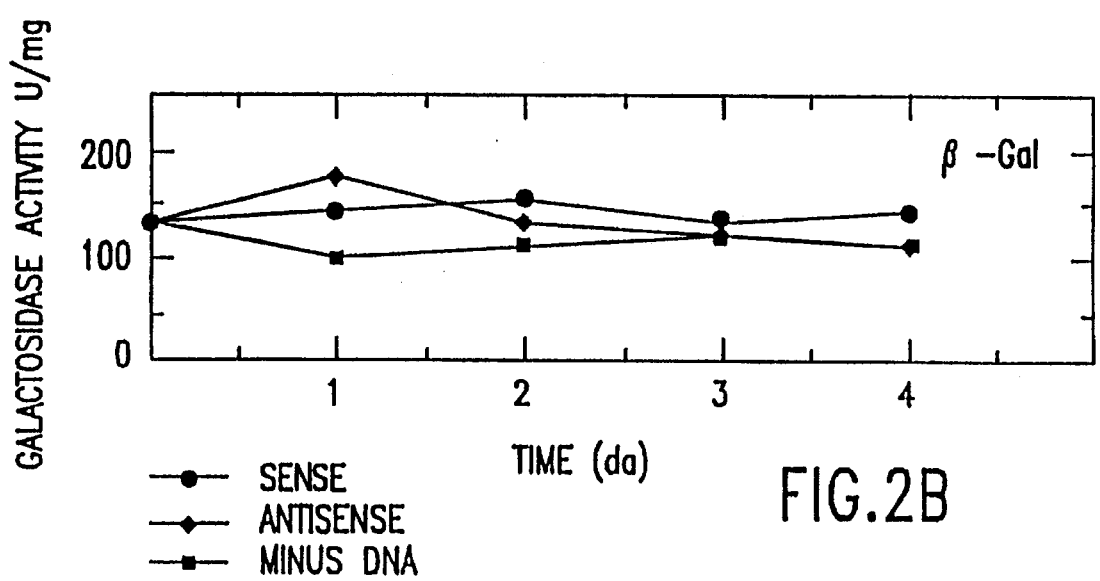

FIGS. 2A–2B. Transient expression of human α-Gal in COS-1 cells. Maximum activity (U/mg) was reached 72 hours post-transfection in cells receiving the p91-AGA construct. No increase in α-Gal activity was observed in cells receiving no plasmid DNA nor in cells receiving the p91 vector with the α-Gal cDNA in the reverse orientation.

Figure 3B:
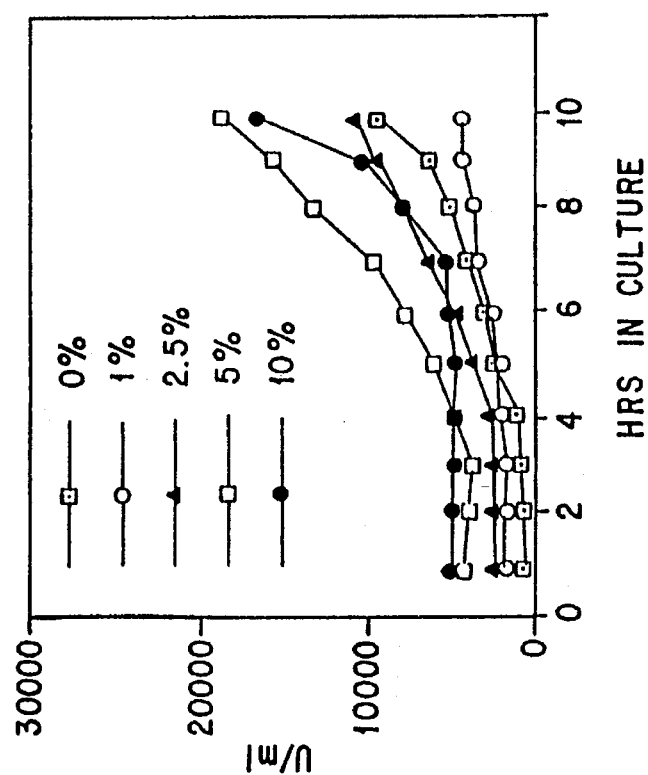
Figure 3A:
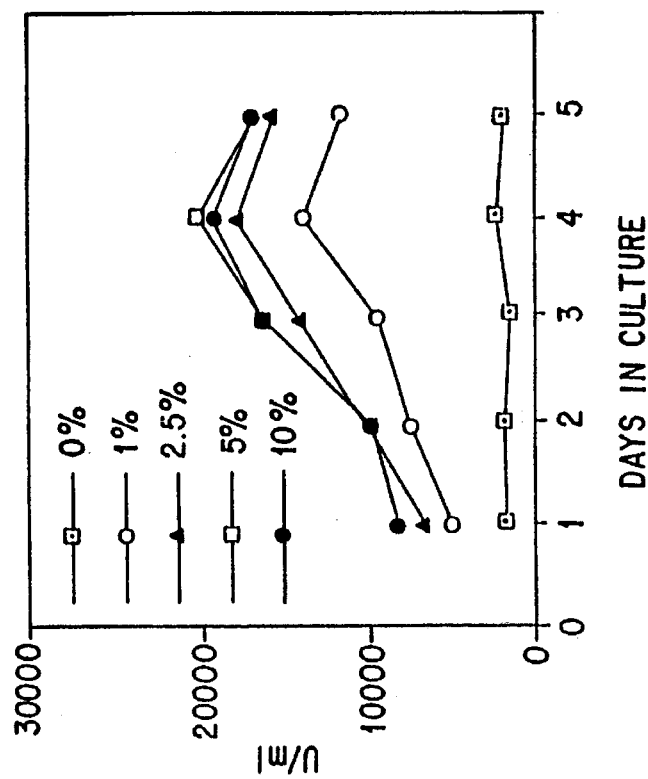

FIGS. 3A–3B. Serum effect on secretion of recombinant α-Gal by CHO DG5.3. Cells were plated in DMEM supplemented with the appropriate serum concentration (FIG. 3A.) Cells were plated in DMEM supplemented with 10% FCS. Following confluency (~4 days), the media was replaced with fresh DMEM supplemented with the appropriate serum concentration (FIG. 3B).

Figure 4:
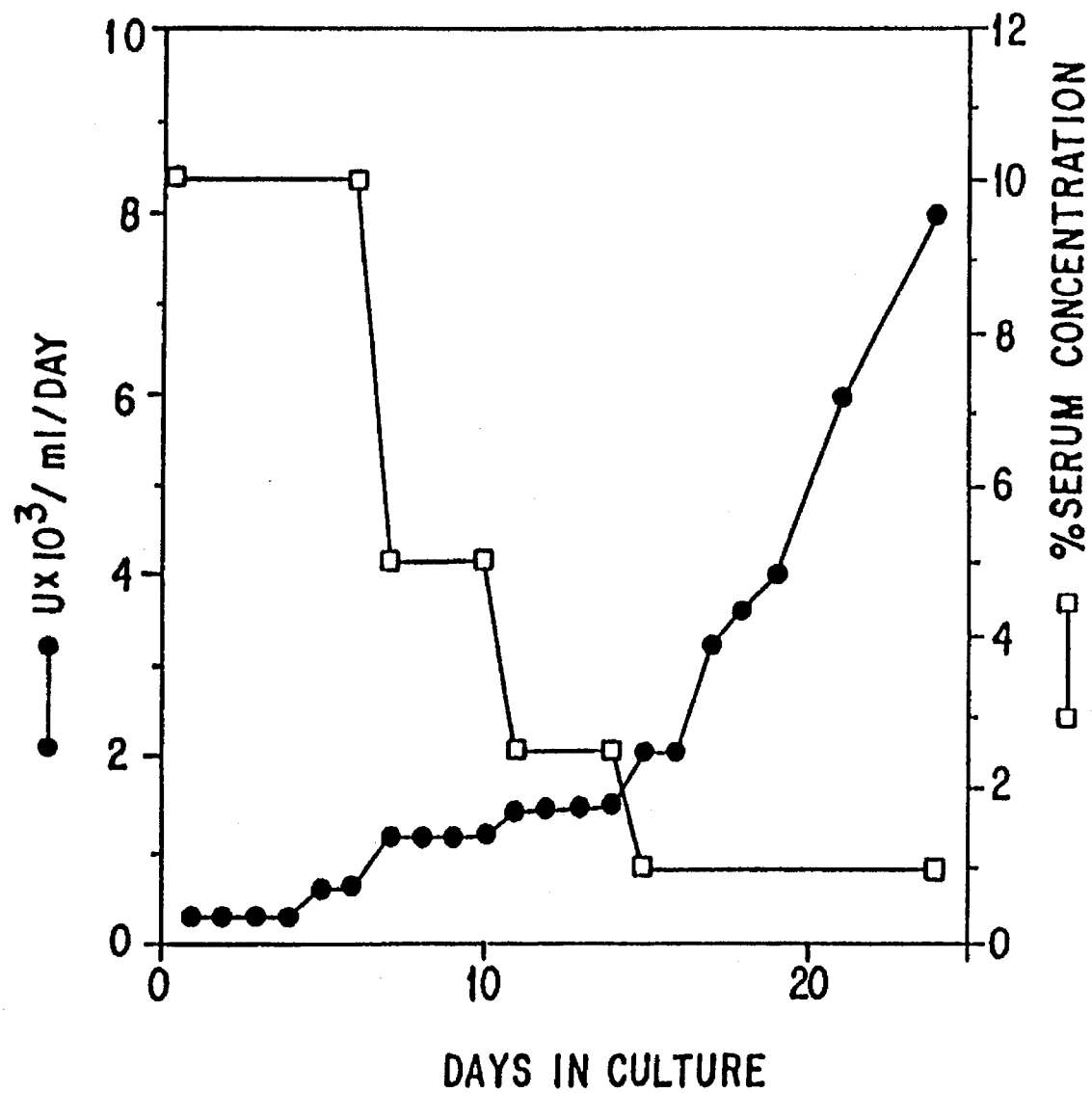

FIG. 4. High-level production of recombinant α-Gal in a hollow fiber bioreactor. The amount of fetal bovine serum required by this system for optimal cell-growth and protein secretion could be decreased to about 1%.

Figure 5:
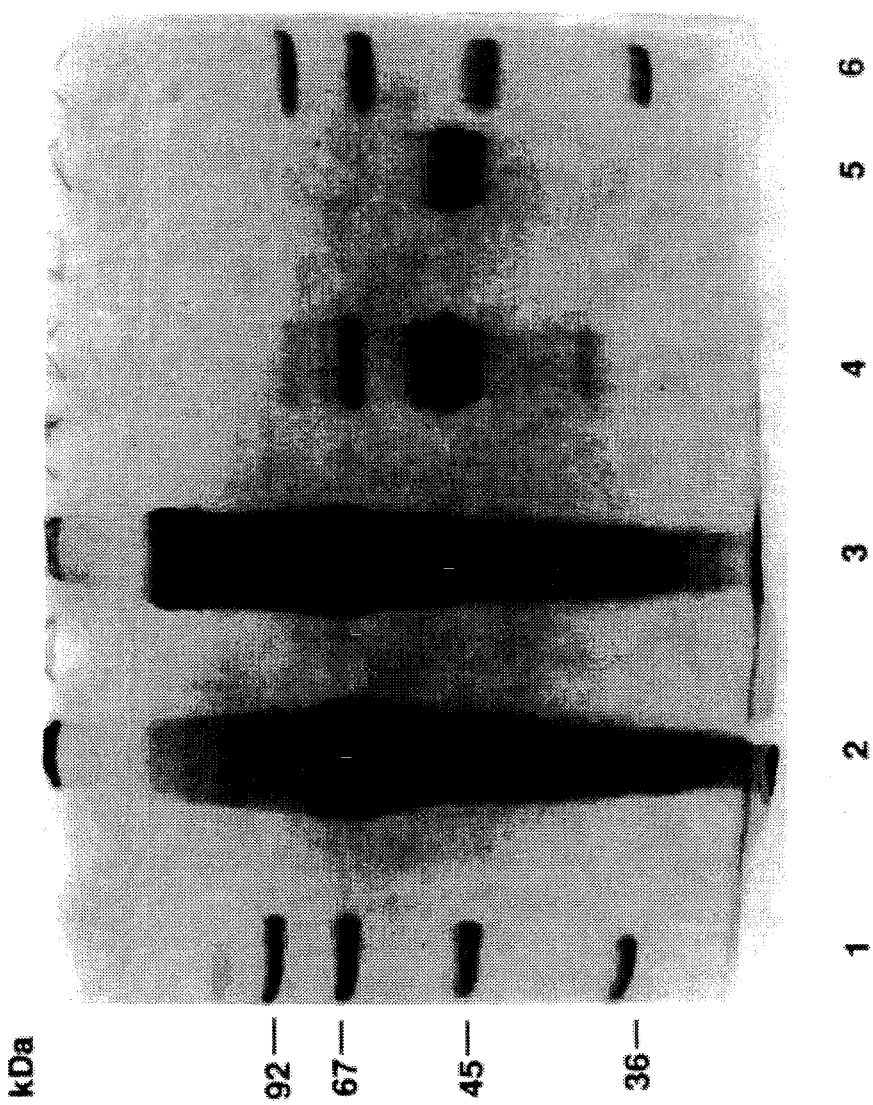

FIG. 5. SDS-PAGE of each step of the α-Gal purificiation scheme. Lanes 1, 6, molecular weight markers; lane 2, crude media; lane 3, affinity chromatography; lane 4, octyl-Sepharose chromatography; lane 5, superose 6 chromatography.

Figure 6:
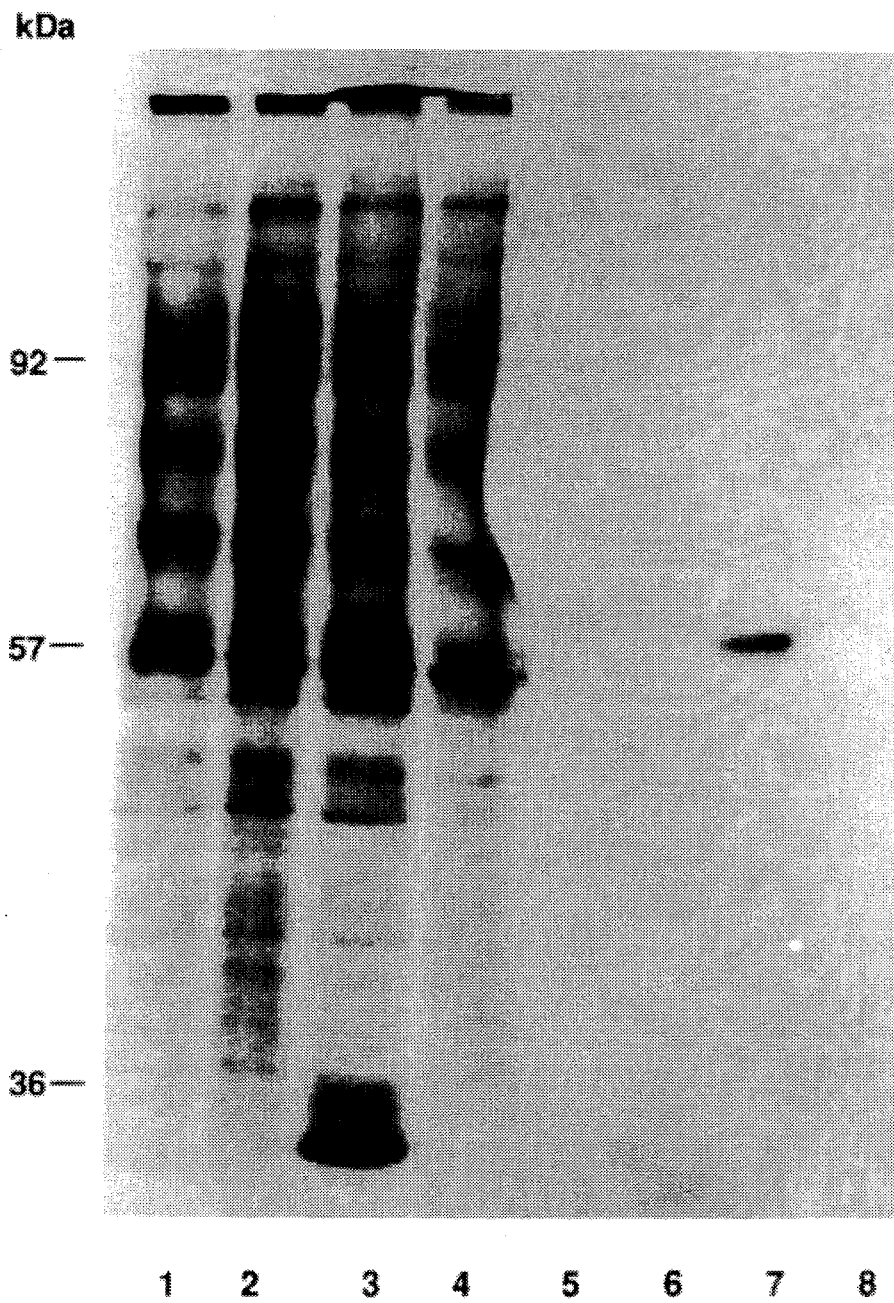

FIG. 6. Total cellular (lanes 1–4) and media (lanes 5–8) from control DG44 cells (lane 1,5), DG5 cells (lanes 2, 6), DG5.3 cells (lanes 3,7) and DG11 cells (lanes 4,8), labeled with [$^{35}$S]-methionine.

Figure 7A:
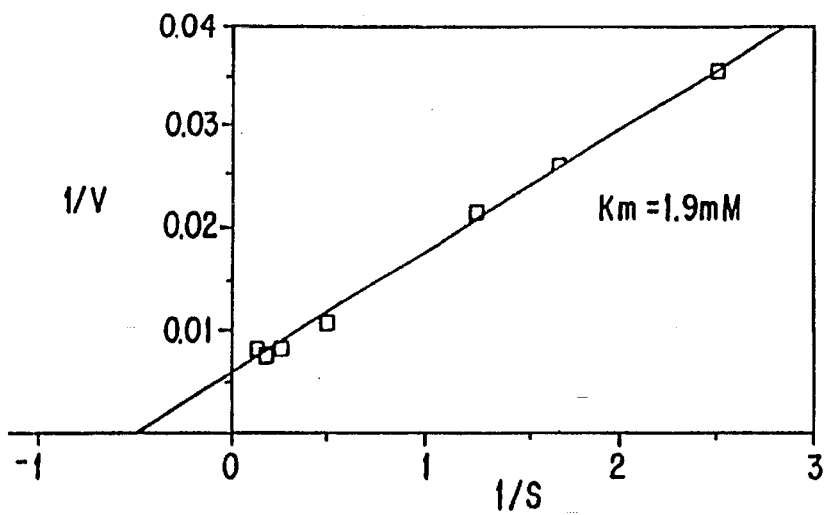
Figure 7B:
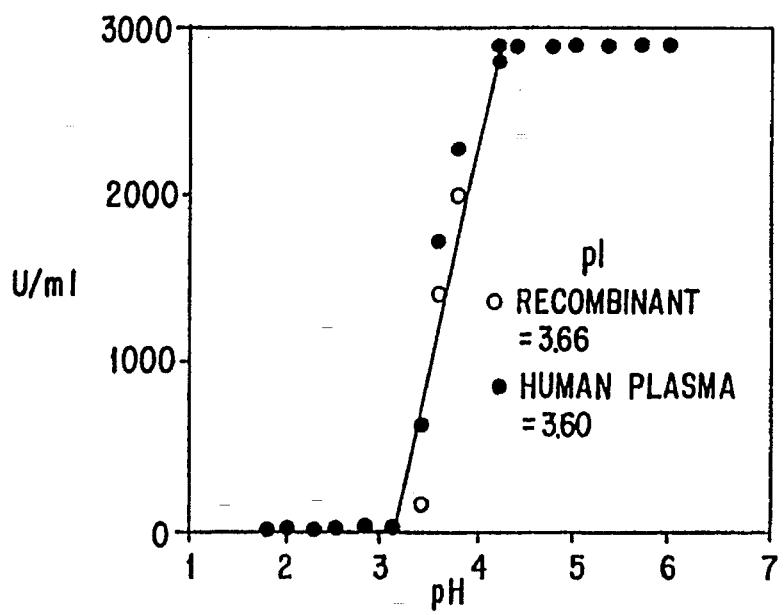
Figure 7C:
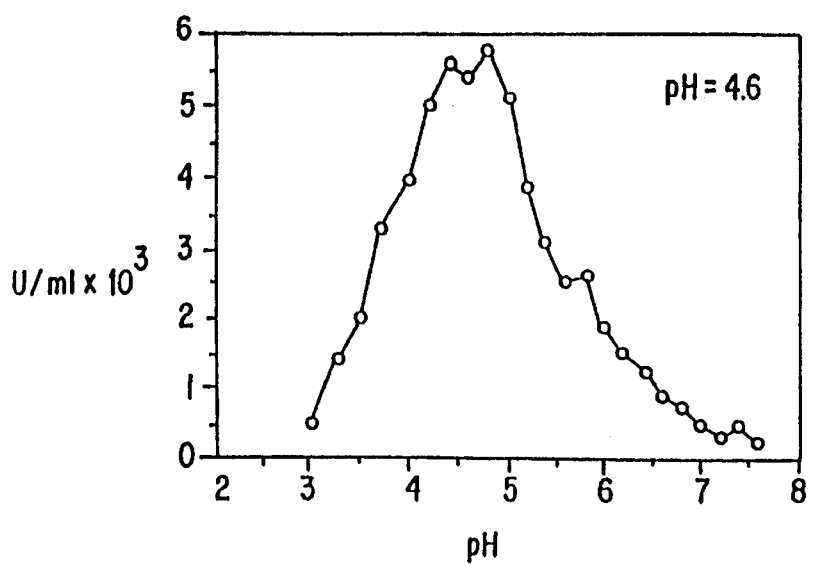

FIGS. 7A–7C. Physicokinetic properties of recombinant α-Gal. Km towards the artificial substrate 4-MU-α-D-galactopyranoside (FIG. 7A). Isoelectric point of recombinant and human plasma purified enzyme (FIG. 7C). pH optimum of the recombinant enzyme (FIG. 7B).

Figure 8A:
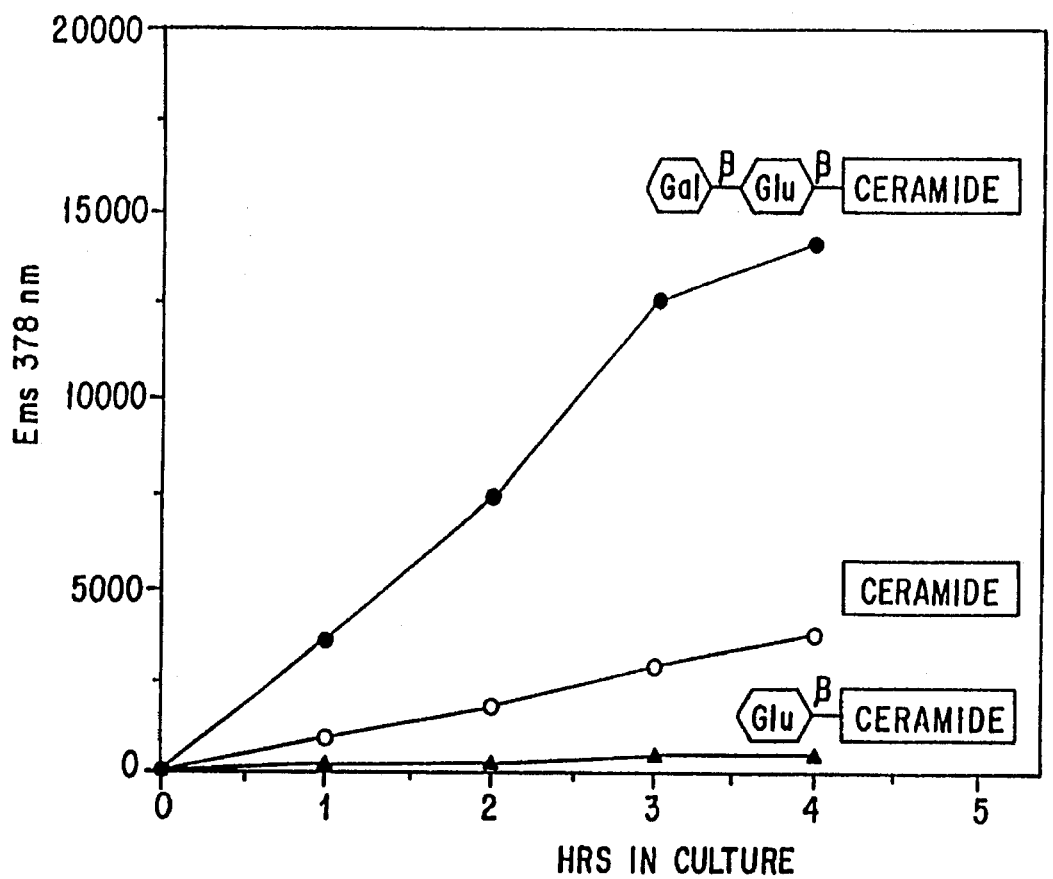
Figure 8B:
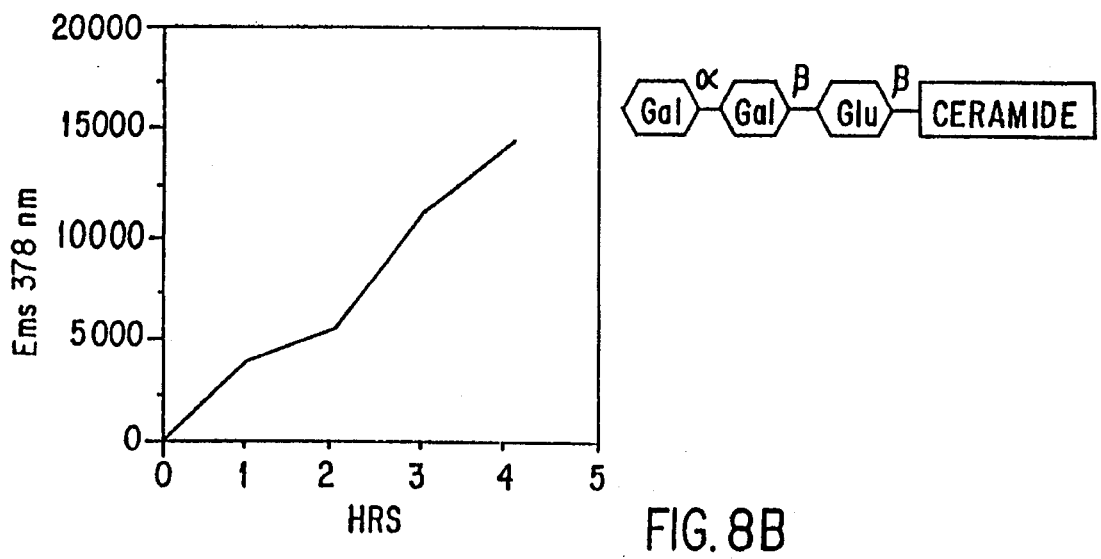

FIGS. 8A–8B. P-$C_{12}$STH degradation by CHO DG5.3 cells overproducing human α-Gal. Rapid degradation of this substrate is observed by the accumulation of P-$C_{12}$SDH.

Figure 9:
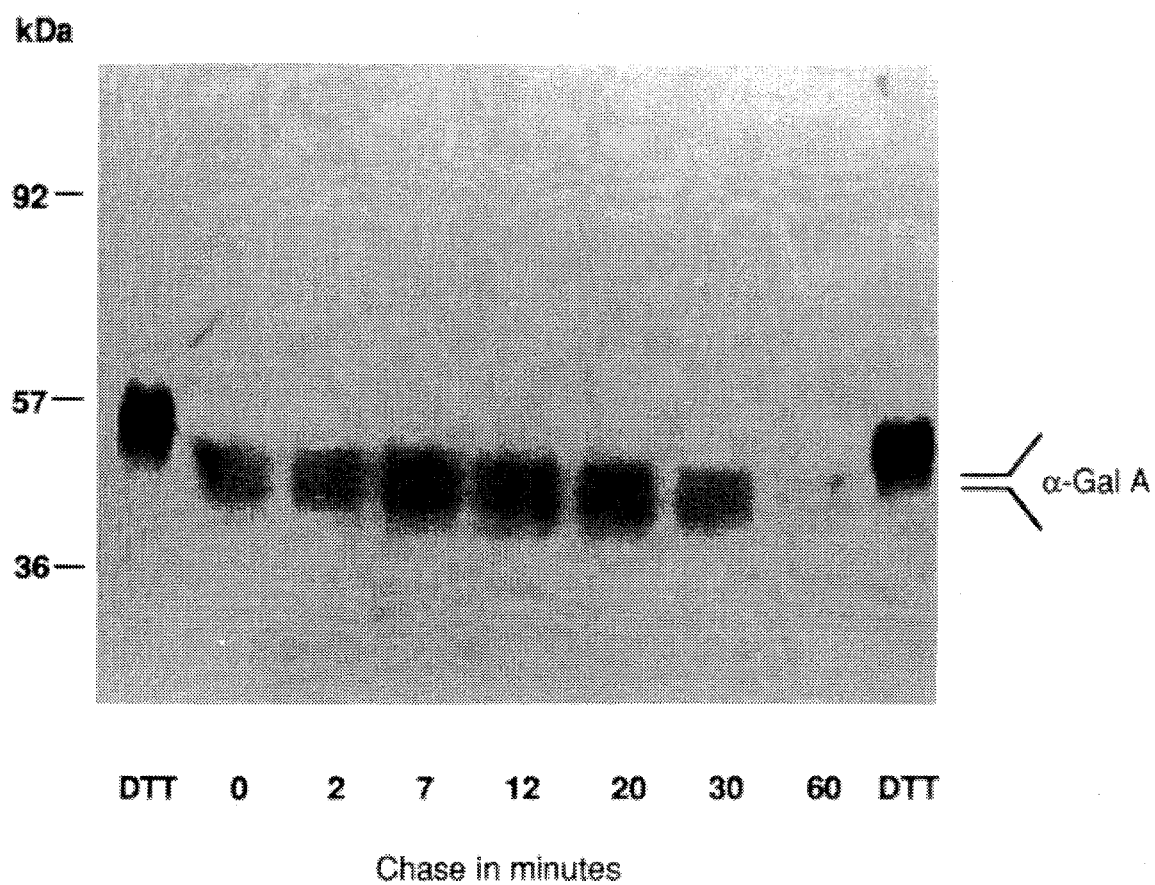

FIG. 9. Acquisition of disulfide bridges by recombinant α-Gal. CHO DG5.3 cells were labeled with [$^{35}$S]-methionine and chased for the indicated times. SDS-PAGE in the absence of a reducing agent reveals the formation of secondary structures through disulfide bond formation.

Figure 10:
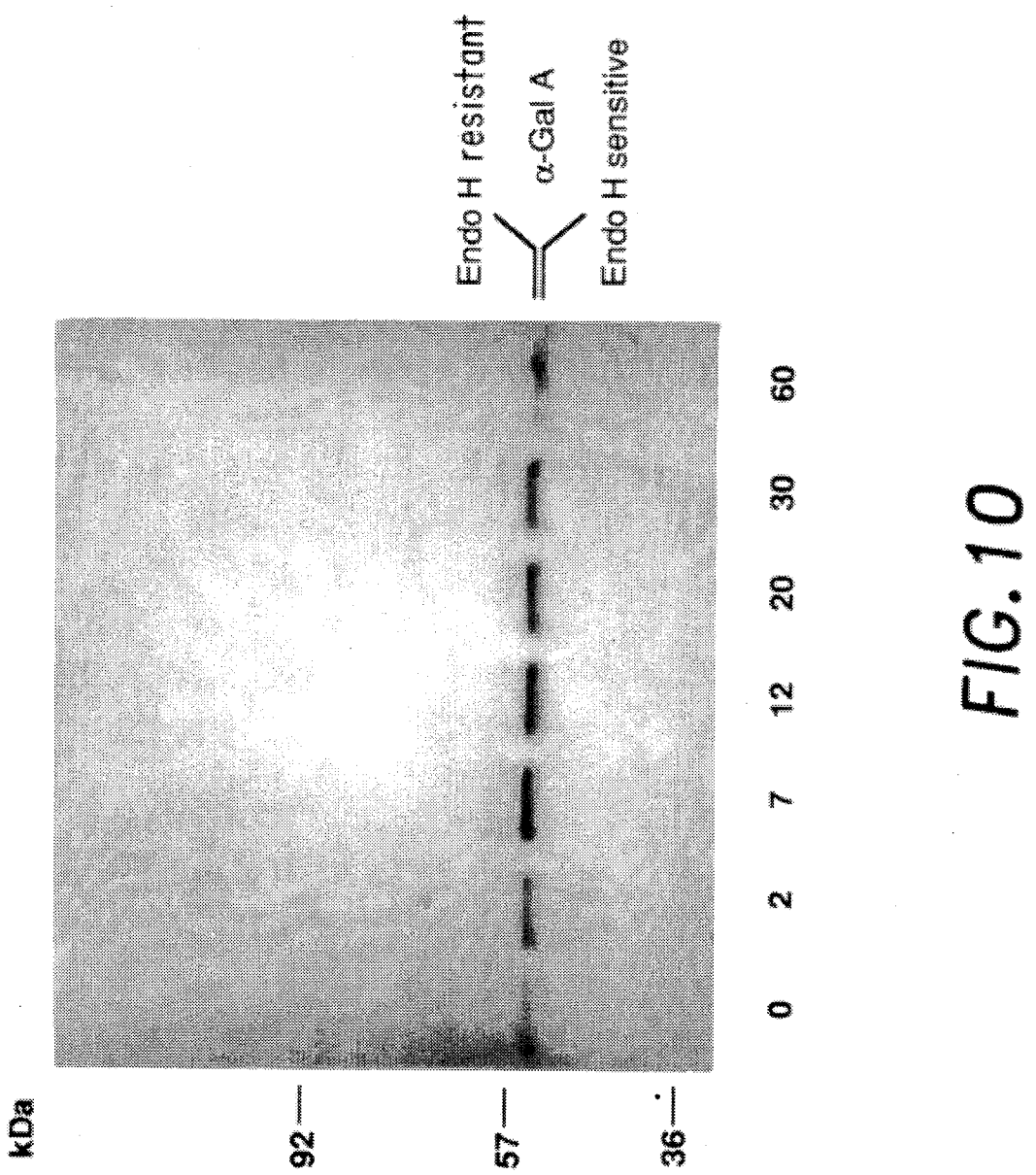

FIG. 10. Arrival of newly synthesized α-Gal to the Golgi network detected by the acquisition of Endo H resistant oligosaccharides, FIG. 11. Secretion rate of recombinant α-Gal. CHO DG5.3 cells were labeled with [$^{35}$S]-methionine for 5 min and chased with cold methionine. Culture media aliquots were removed at the indicated times and immunoprecipitated with anti-α-Gal polyclonal antibodies.

Figure 12:
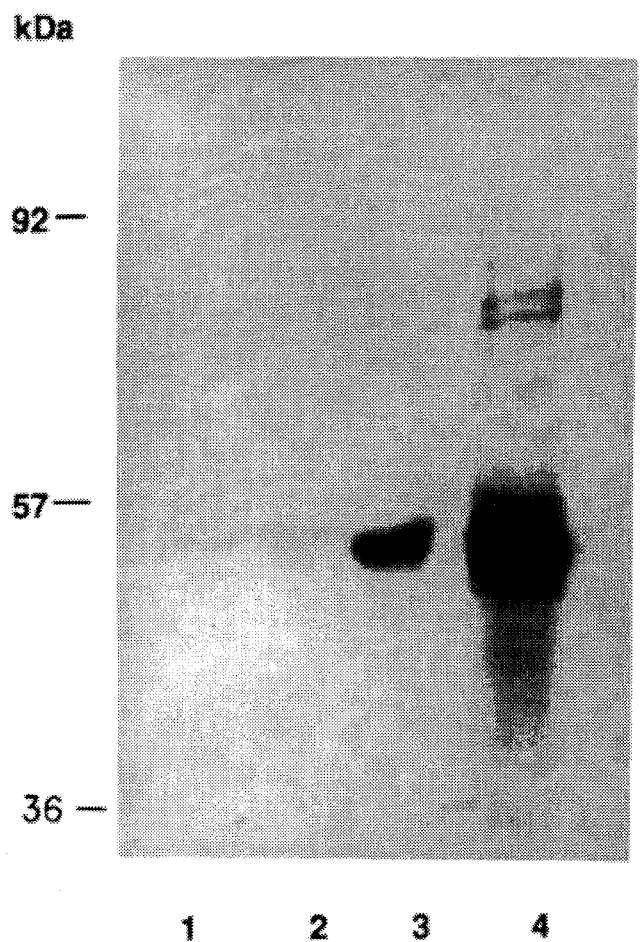

FIG. 12. SDS-PAGE of culture media from DG44 (lane 1; control), DG5 (lane 2) and DG5.3 (lanes 3,4) cells labeled with [$^{35}$S]-methionine for 1 hour (lanes 1–3) and 24 hours (lane 4).

Figure 13:
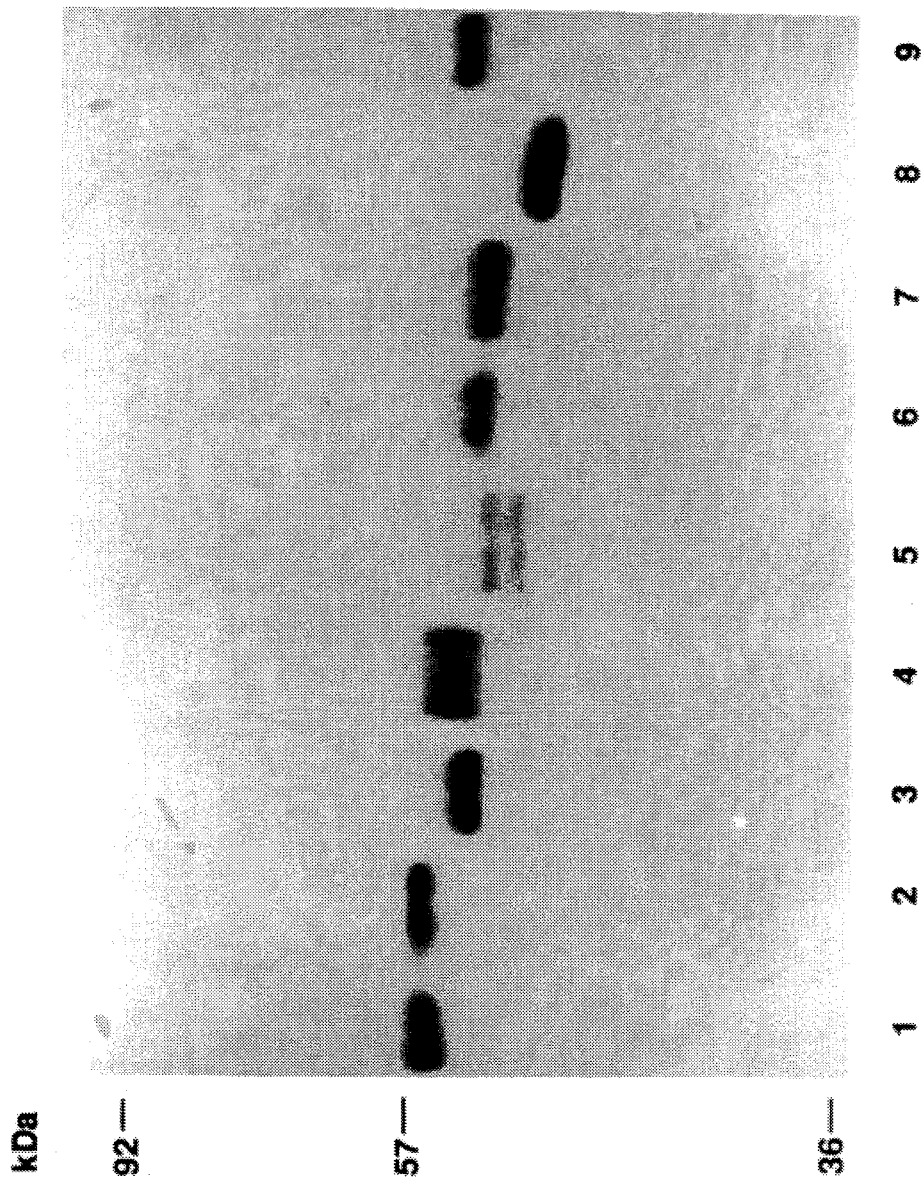

FIG. 13. Analysis of the carbohydrate moieties on recombinant α-Gal. CHO DG5.3 cells were labeled with [$^{35}$S]-methionine for 24 hours, the culture media collected and the recombinant enzyme immunoprecipitated. Aliquots were digested with endo D (lane 2), Endo H (lane 3), Endo F (lane 4), PNGase F (lane 5), Endo D and H (lane 6), Endo H and F (lane 7), and Endo H, F, and PNGase F (lane 8). Untreated samples (lanes 1, 9).

Figure 14:
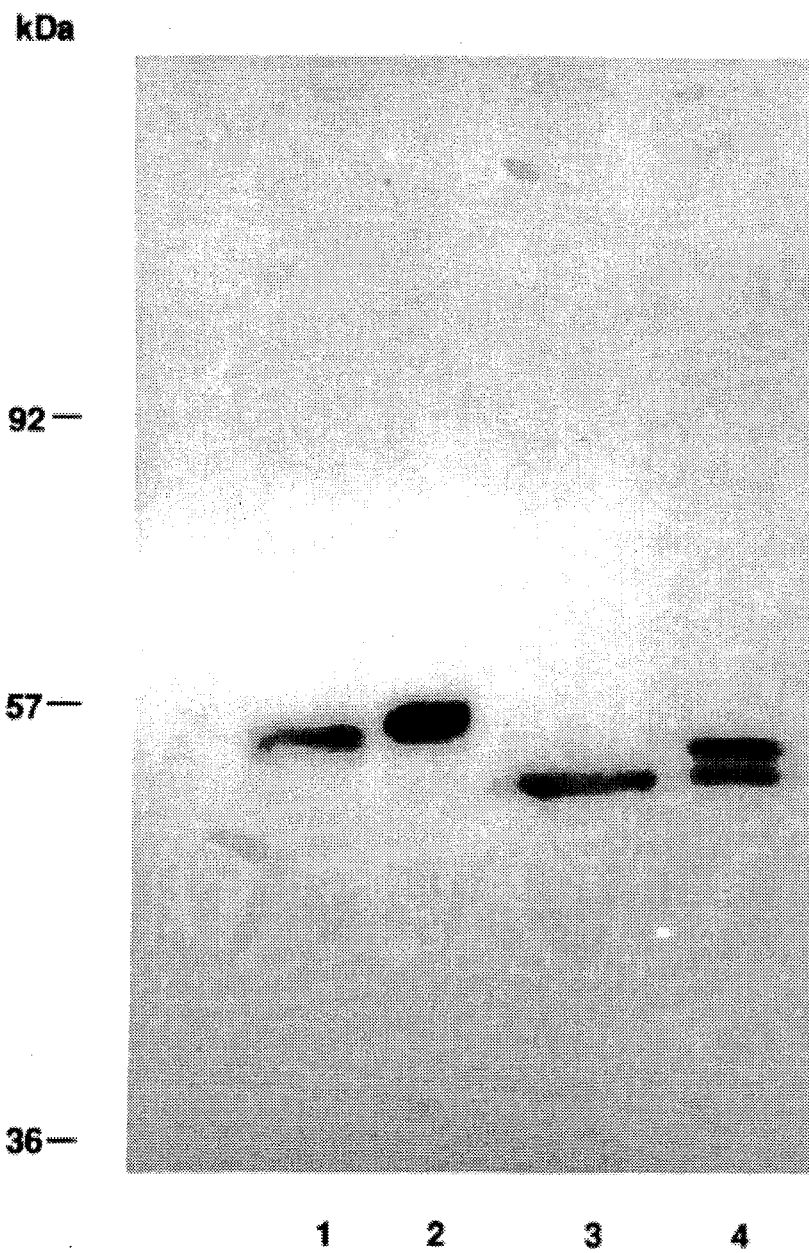

FIG. 14. Cellular (lanes 1,3) and secreted (lanes 2,4) forms of recombinant α-Gal treated with PNGase F (lanes 3,4). Controls (lanes 1,2).

Figure 15:
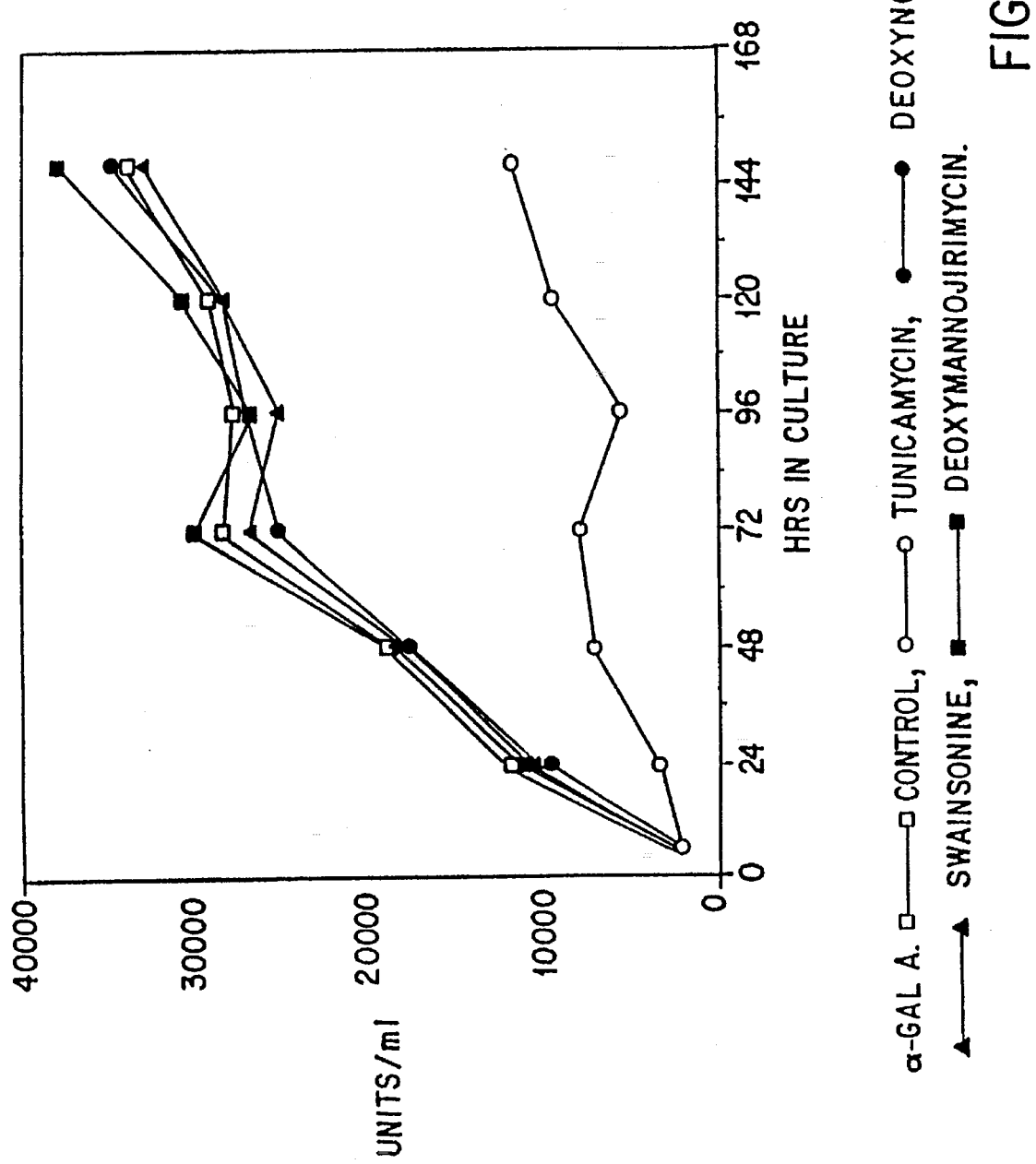

FIG. 15. Effect of glycosylation inhibitors on the secretion of recombinant α-Gal.

Figure 16:
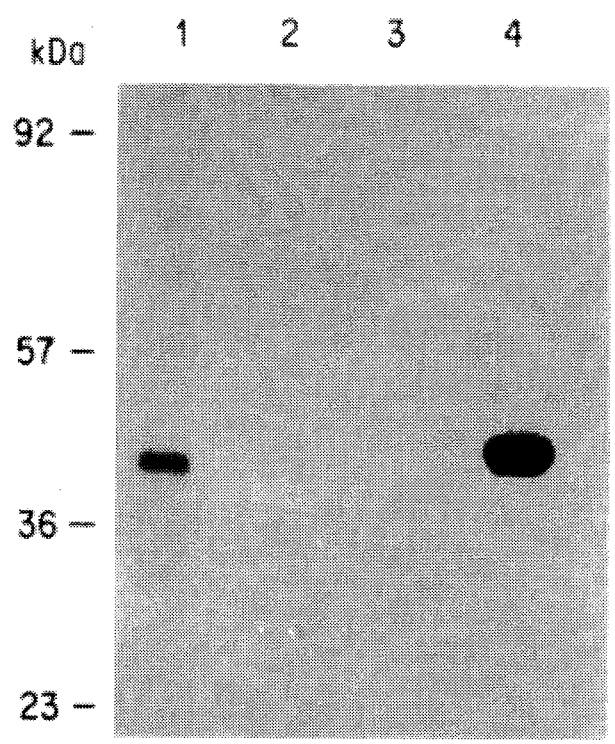

FIG. 16. $^{32}$P labelling of CHO DG44 (lanes 2, 3) and DG5.3 (lanes 1, 4). α-Gal was immunoprecipitated from cells (lanes 1, 2) and media (lanes 2, 3).

FIGS. 17A–17D. QAE-Sephadex chromatography of endo H sensitive oligosaccharides of recombinant α-Gal.

Untreated, dilute HCl treated, neuraminidase treated and alkaline phosphatase treated oligosaccharides.

Figure 18:
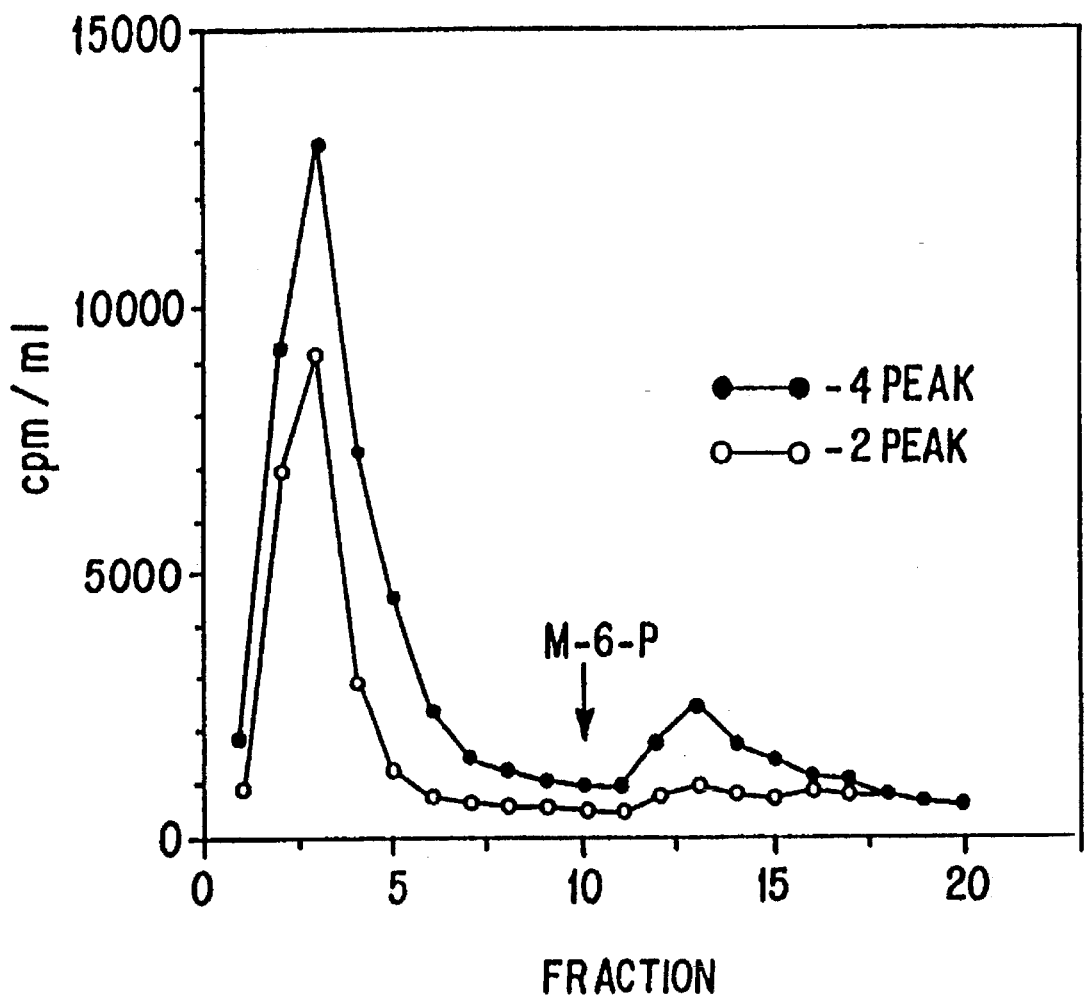

FIG. 18. Endo H sensitive oligosaccharides of recombinant α-Gal chromatographed on M-6-P receptor. solid circles, peak minus 4, open circles, peak minus 2.

Figure 19:
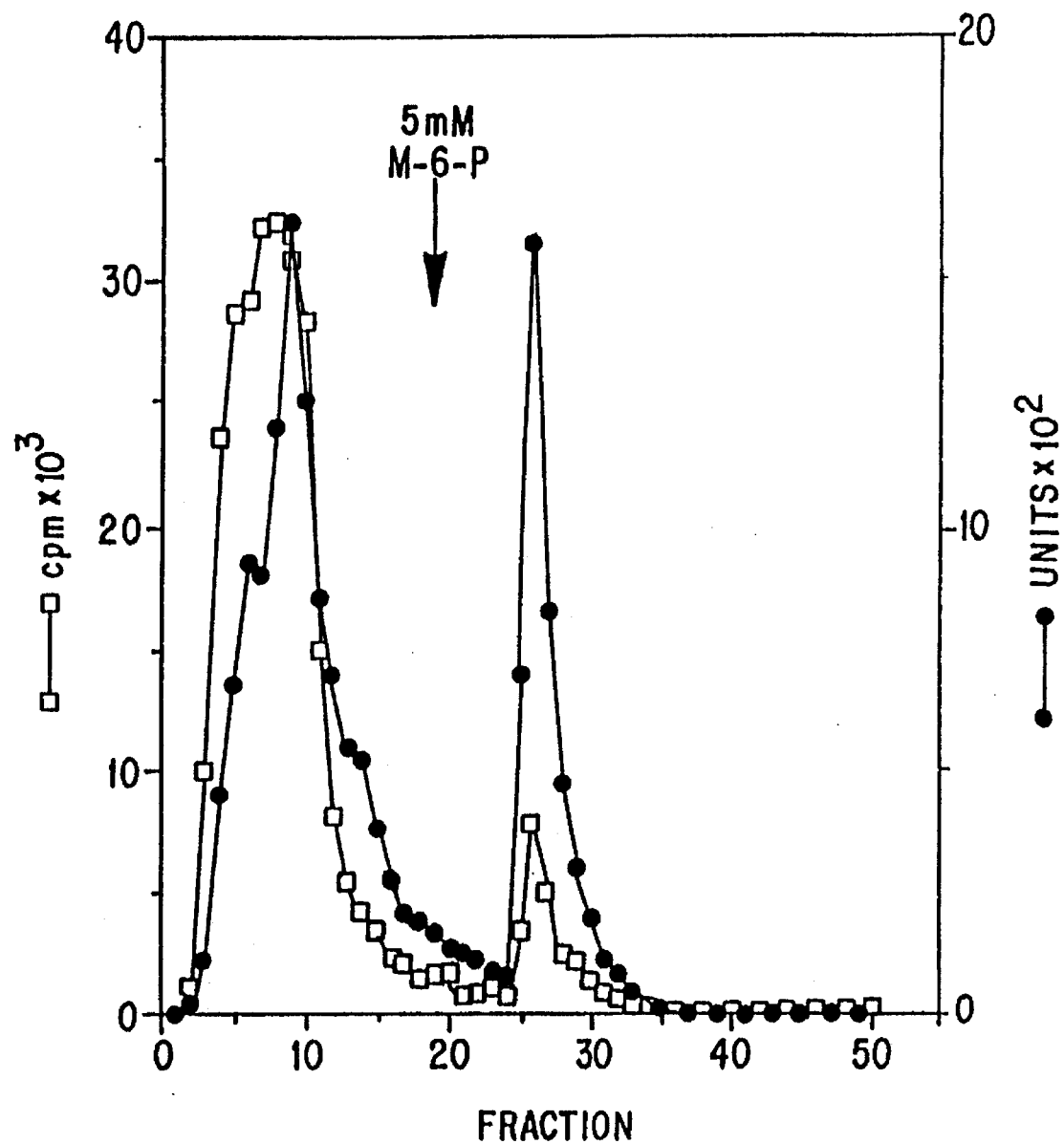

FIG. 19. Recombinant α-Gal chromatography on M-6-P receptor. DG5.3 cells labeled with [$^{35}$S]-methionine for 24 hours and media collected for chromatography. Solid circles, α-Gal activity; open boxes, total radioactivity.

Figure 20A:
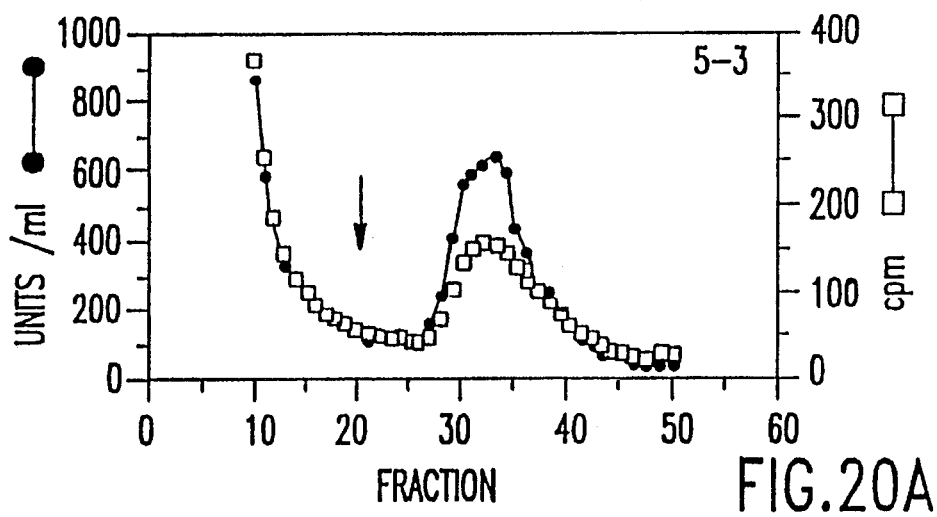
Figure 20B:
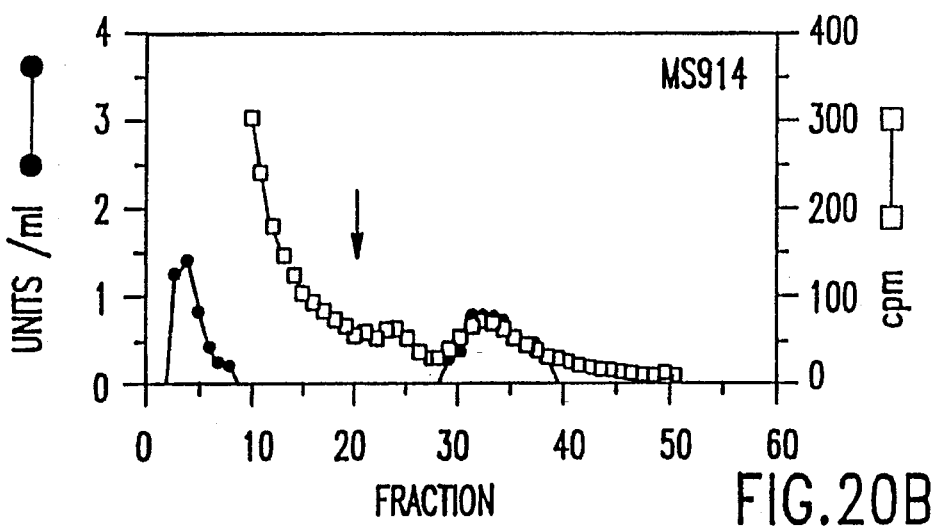
Figure 20C:
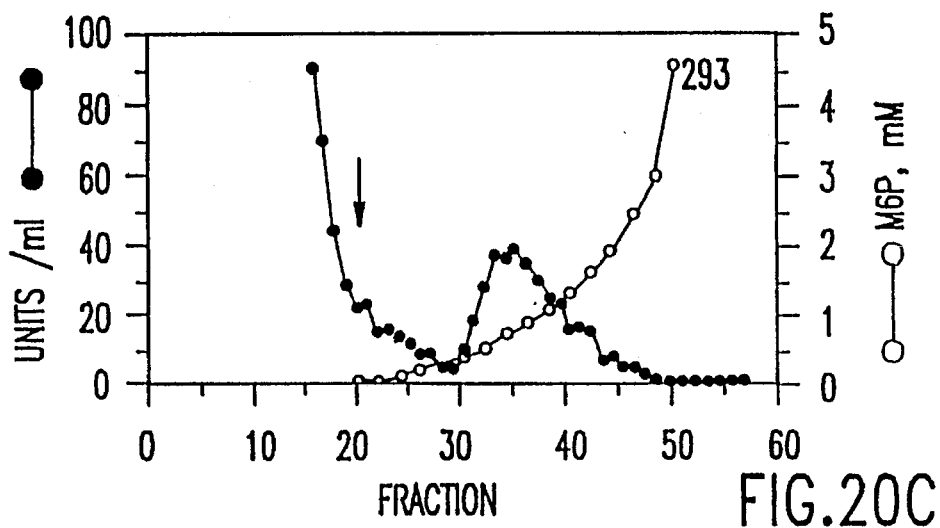

FIGS. 20A–20C. Recombinant and human α-Gal affinity chromatography on M-6-P receptor. Cells were labeled with [$^{35}$S]-methionine for 24 hours in the presence of NH$_4$Cl and the culture media were collected. DG5.3 secretions (FIG. 20A), MS914 secretions (FIG. 20B) and 293 secretions (FIG. 20C). Solid circles, α-Gal activity. Squares, total radioactivity. Open circles, M-6-P gradient used for elution.

Figure 21:
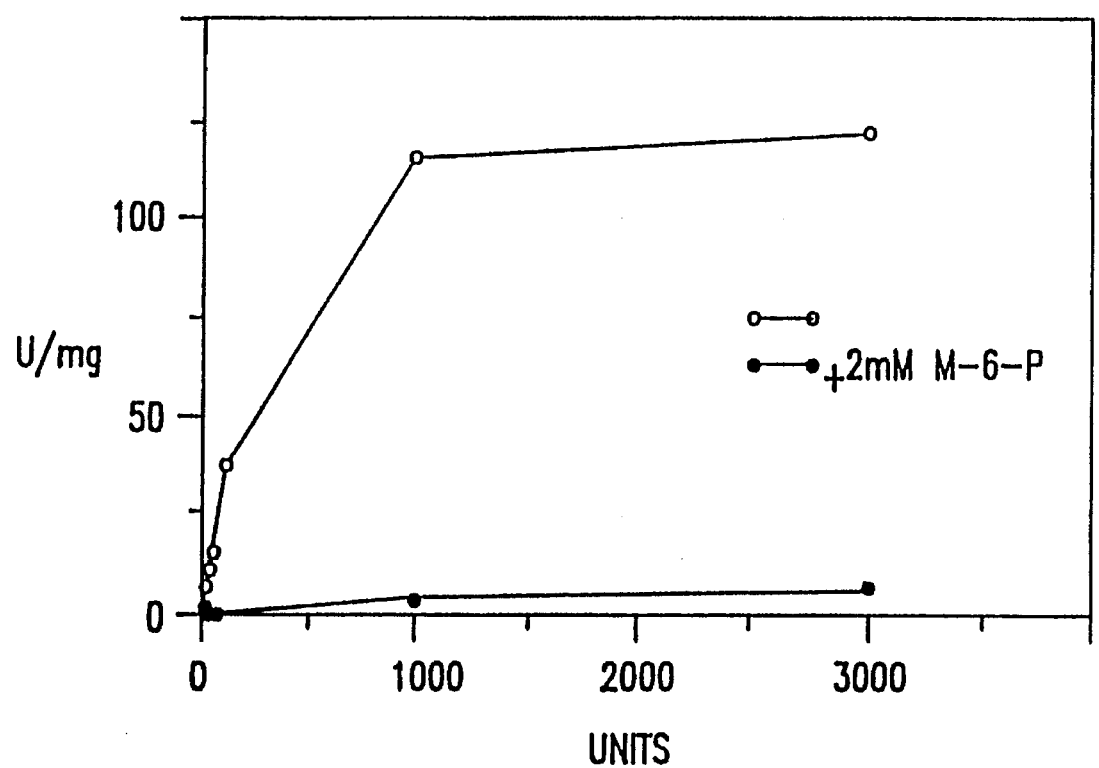

FIG. 21. Uptake of recombinant α-Gal by Fabry fibroblasts. Cells were incubated for the indicated amounts of α-Gal for 6 hours. Open circles, α-Gal uptake, closed circles, uptake in the presence of 2 mM M-6-P.

Figure 22:
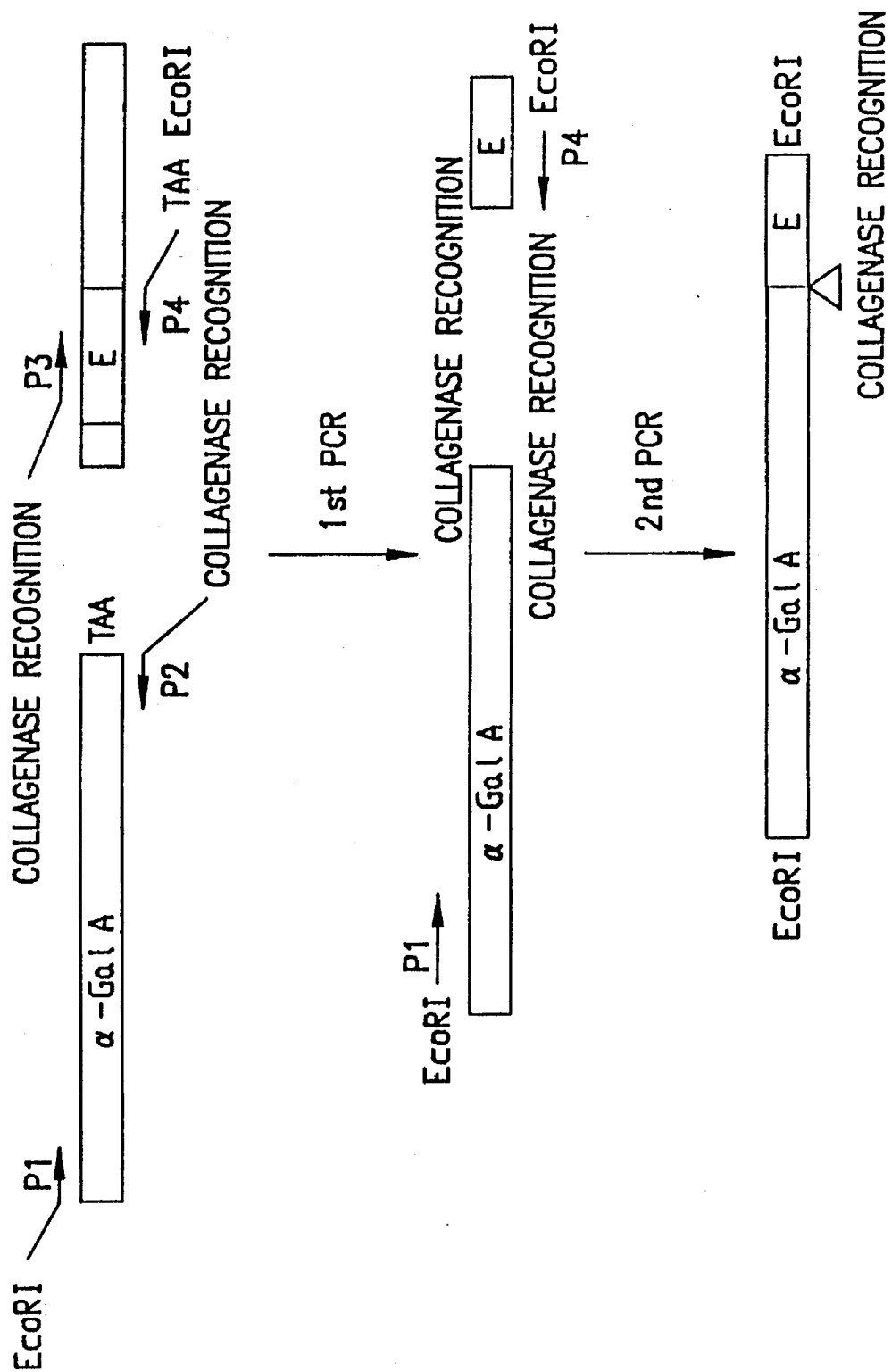

FIG. 22. Construction scheme of the α-Gal protein A fusion. The fusion was accomplished in two separate PCR reactions as described in Materials and Methods.

FIG. 23. Nucleotide sequence (SEQ ID NO:11) of the protein A domain E (SEQ ID NO:12), collagenase cleavage sequence and 3'α-Gal sequence (FIG. 23A). Schematic of the fusion construct showing the collagenase consensus in relation to the α-Gal and protein A domains (FIG. 23B).

Figure 24A:
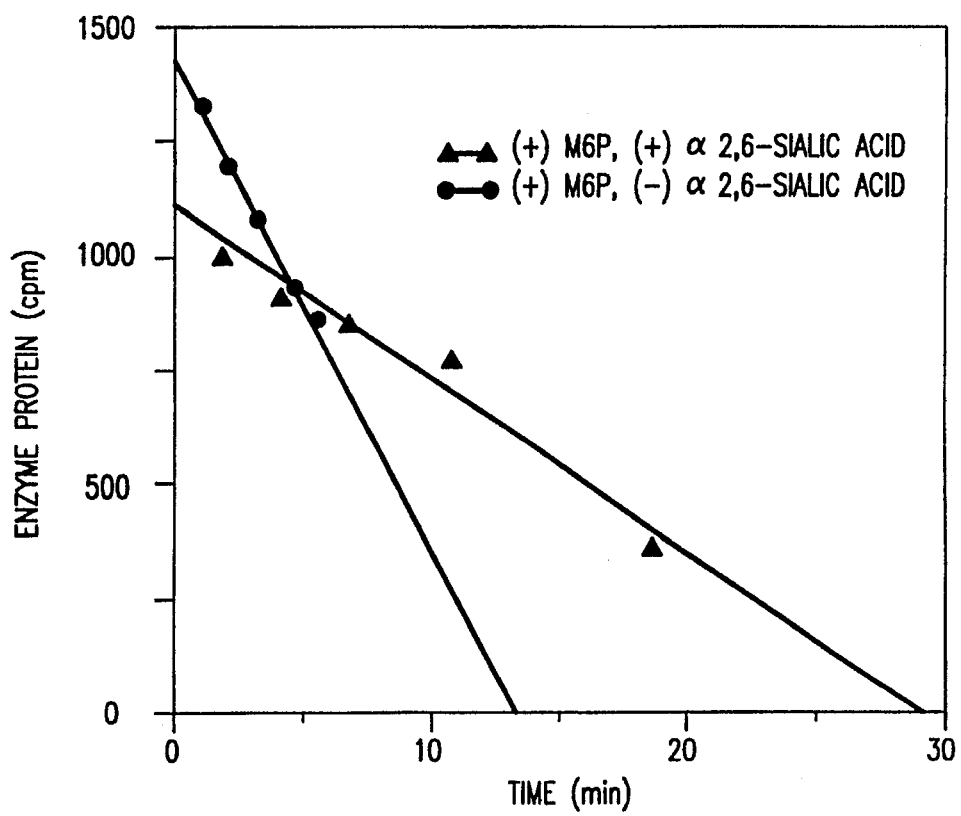
Figure 24B:
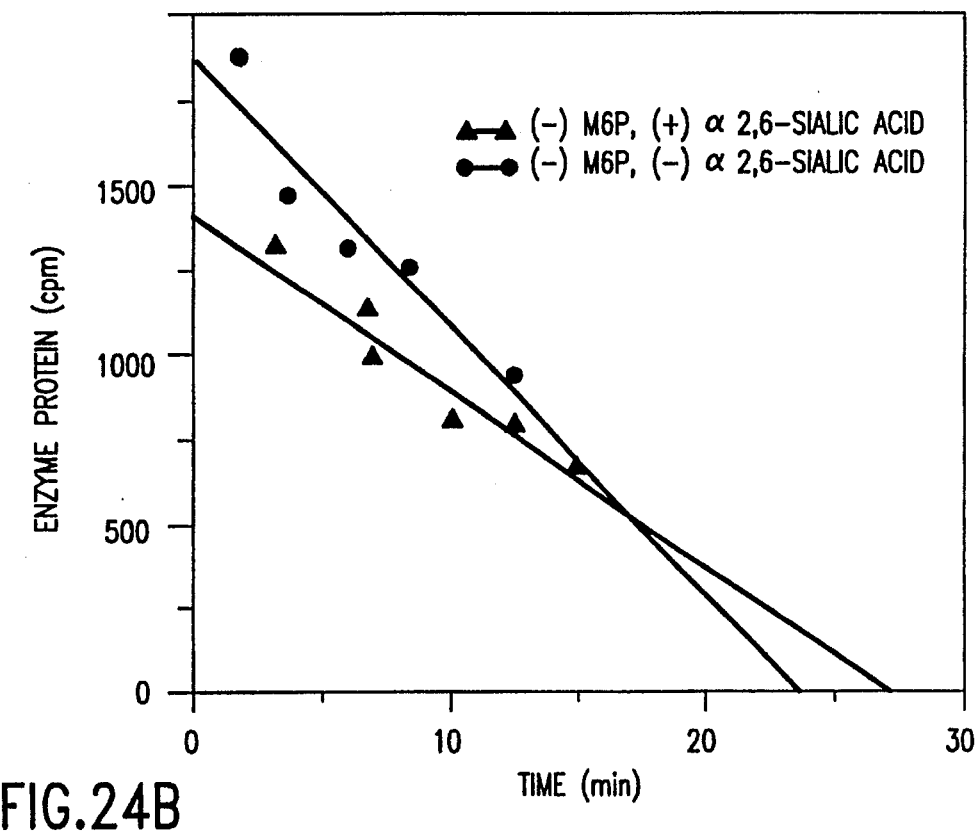

FIGS. 24A–24B. Plasma clearance following intravenous administration to mice of the recombinant human secreted α-galactosidase A containing α2,6-sialic acid residues (Δ—Δ) and the non-α2,6-sialylated glycoform (●—●) upper graph, compared with the plasma clearance of these glycoforms following treatment with acid phosphatase. Each point represents the average of the values from two independent injections. The $T_{1/2}$ values were estimated by extrapolation.

Figure 25:
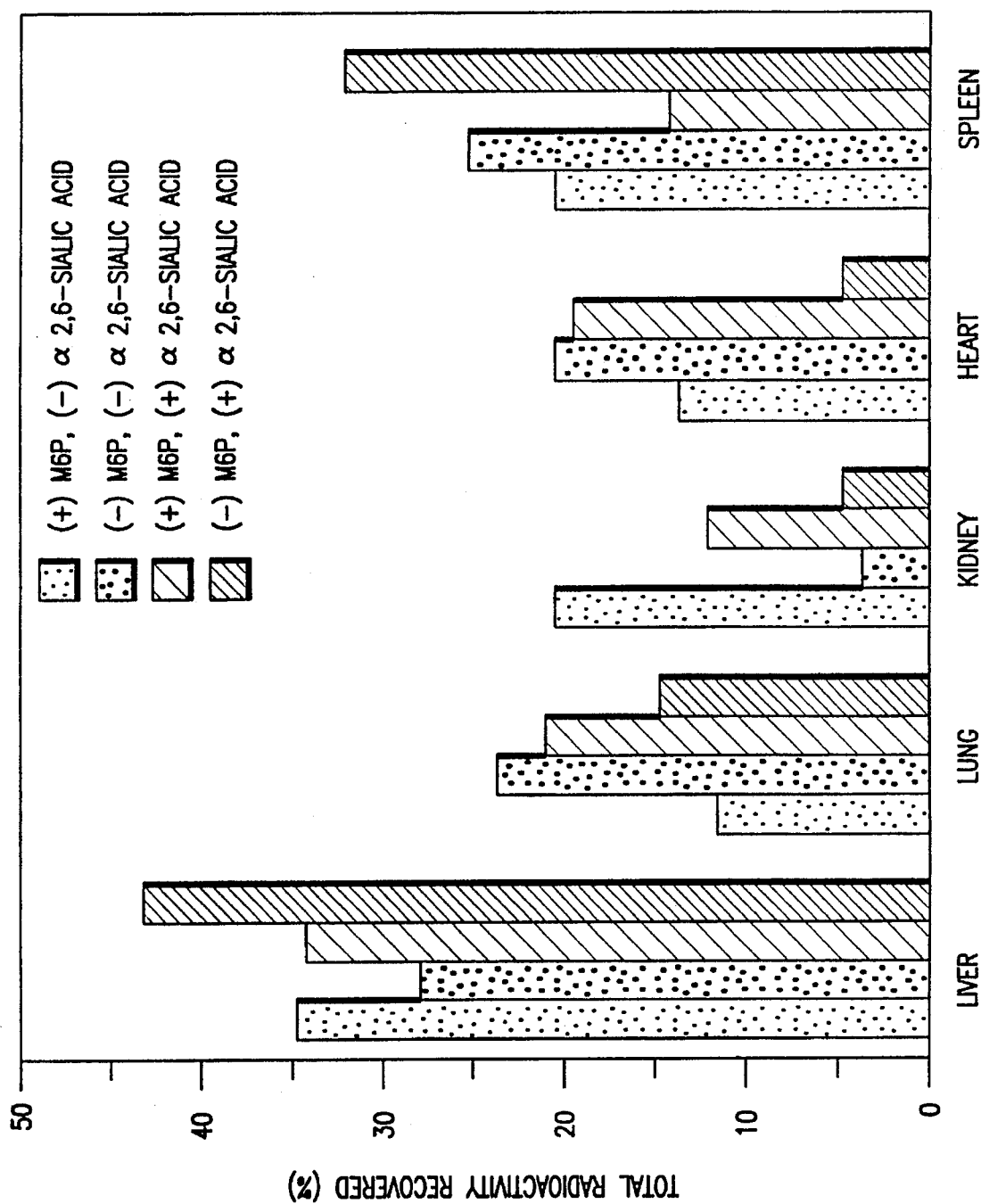

FIG. 25. Tissue distribution of different forms of recombinant human secreted α-Gal A following intravenous administration to mice. Each point represents the average of the values from two independent injections.

FIGS. 26A–26E. DG5.3-1000Mx CHO Cells Contain Crystalline Structures of Overexpressed Human α-Gal A. Electron micrographs of DG5.3-1000Mx cells showing crystalline structures in single membrane-limited vacuoles (FIG. 26A) and in vesicles, presumably in the dilated trans-Golgi (FIG. 26B; bar, 0.15 μm and 0.10 μm, respectively). (FIG. 26C and FIG. 26D) Immunoelectron microscopic localization of human α-Gal A with 10 nm colloidal gold particles (bar, 0.31 μm snf 0.19 μm, respectively). (FIG. 26E) Electron micrograph of parental dfhr DG44 cells (bar, 1.11 μm); inset showing Golgi complex (arrows) in dfhr DG44 cells (bar, 0.5 μm).

Figure 27B:
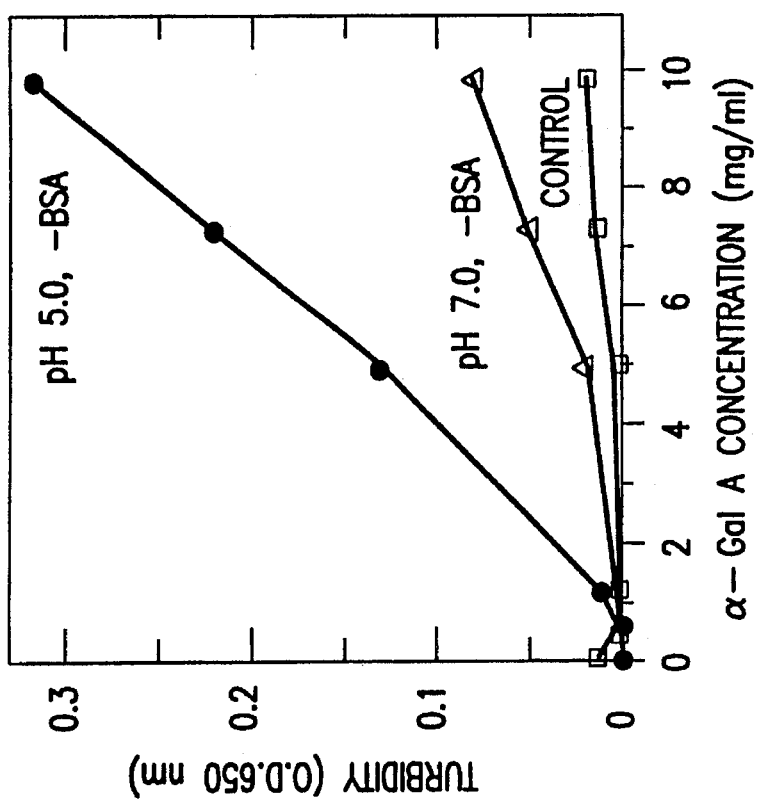
Figure 27A:
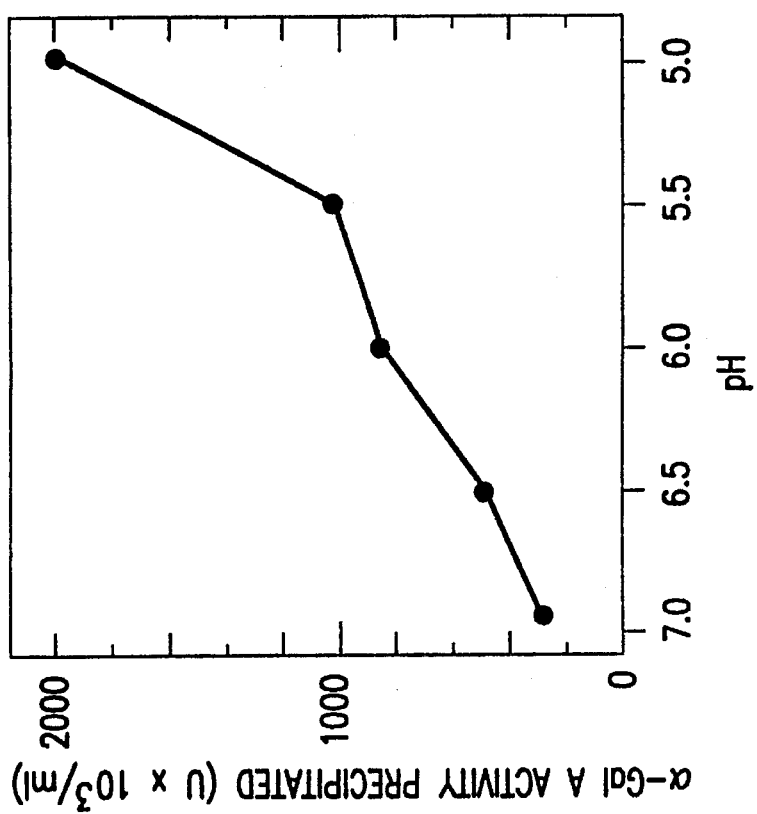
Figure 27C:
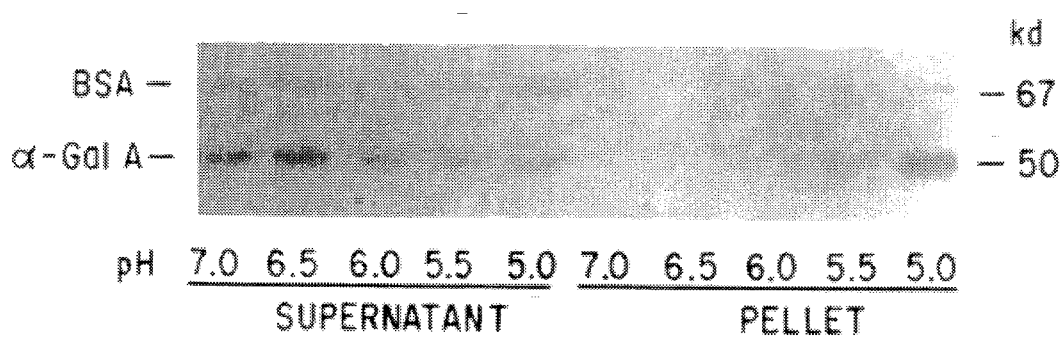

FIGS. 27A–27C. Aggregation of Purified Secreted α-Gal A is Enzyme Concentration and pH Dependent. (FIG. 27A) Precipitation of α-Gal A (10 mg/ml) with decreasing pH. Note that about 12% of incubated enzyme was precipitated at pH 6.0, the estimated pH of the trans-Golgi Network (TGN). (FIG. 29B) Turbidity of increasing concentrations of secreted α-Gal A at pH 5.0 (closed circles) and pH 7.0 (closed triangles) in the absence of Bovine Serum Albumin (BSA). As a control for non-specific precipitation with increasing protein concentration, secreted α-Gal A (1 mg/ml) was mixed with increasing BSA concentrations (0.1 to 10 mg/ml) at pH 5.0 (solid squares). (FIG. 27C) SDS-PAGE of the supernatant and pellet fractions from mixtures of purified secreted α-Gal A (10 mg/ml) and BSA (2 mg/ml) incubated at decreasing pH values. Note that α-Gal A was precipitated with decreasing pH whereas the concentrations of soluble and precipitated BSA were essentially unchanged.

Figure 28:
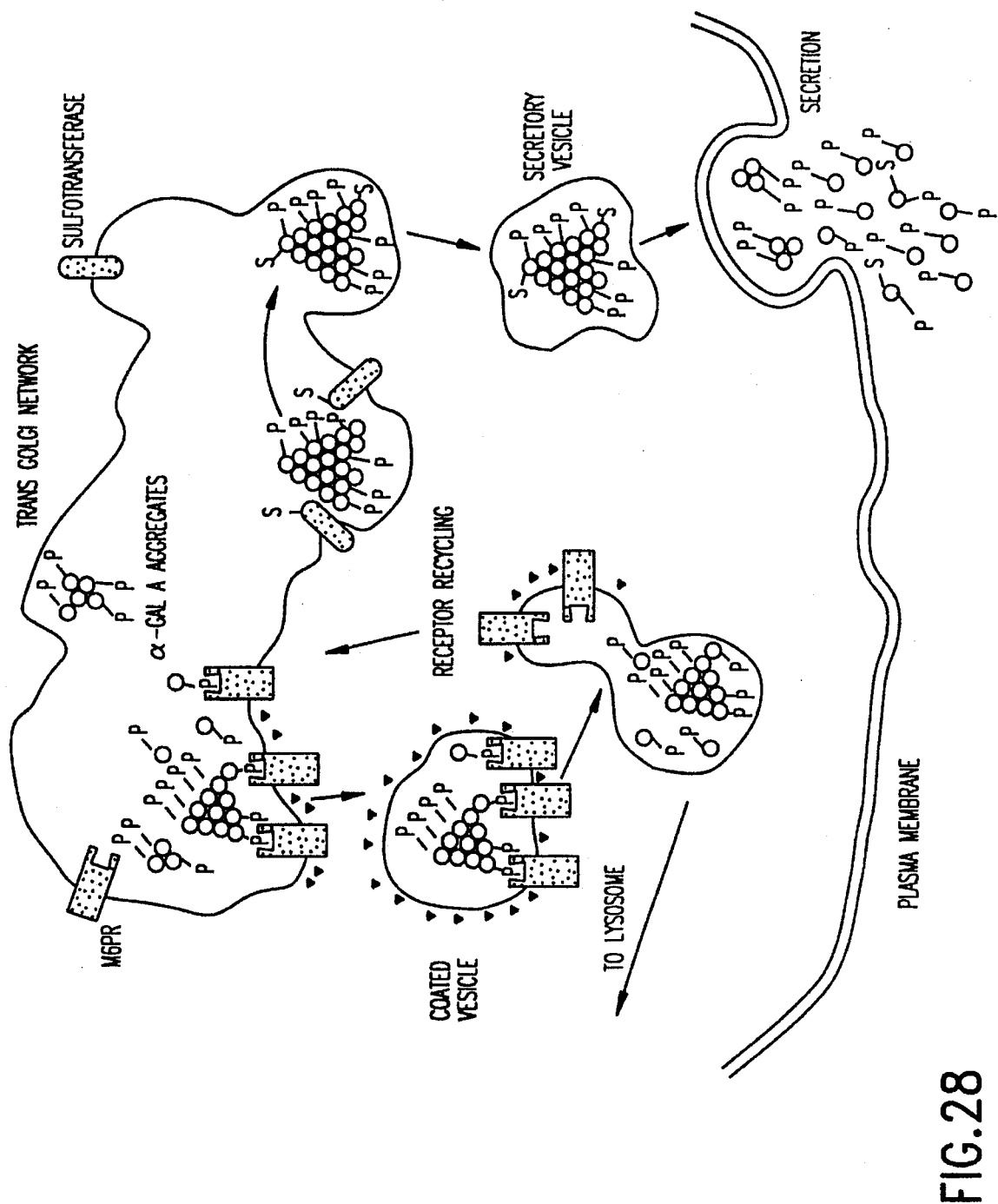

FIG. 28. Aggregation-Secretion Model for Selective Secretion of Human α-Gal A Overexpressed in CHO Cells. High level overexpression in CHO cells of human α-Gal A or other lysosomal enzymes which normally are targeted to the lysosome results in their selective secretion due to their aggregation and the resultant inaccessibility of their M6PR signals. The enzyme undergoes normal post-translational processing until it arrives in the TGN, where the overexpressed enzyme undergoes protein-protein interactions and forms smaller soluble and larger particulate aggregates, due to lower pH of the TGN. The TGN becomes dilated with the overexpressed enzyme. Some aggregates and soluble enzyme with exposed M6P signals are trafficked to lysosomes, while the majority of aggregates whose M6P are not accessible are exocytosed by default via the constitutive secretory pathway. In addition, decreased sulfation may occur as the tyrosines in the enzyme aggregates destined for secretion are unavailable to the sulfotransferase. This model may explain the selective secretion of other overexpressed proteins that normally are targeted to specific organelles.

5. DETAILED DESCRIPTION OF THE INVENTION

The present invention relates to the production of biologically active human α-Gal A involving cloning and expressing the nucleotide coding sequences for the enzyme in eukaryotic expression systems. Successful expression and production of this purified, biologically active enzyme as described and exemplified herein is particularly significant for a number of reasons. For example, past efforts to express the full-length cDNA encoding α-Gal A using various prokaryotic expression vectors resulted in expression of the enzyme, as evidenced by enzyme assays of intact microbial host cells and growth on melibiose as the carbon source; however, the human enzyme was expressed at low levels and could not be purified from the bacteria. These results indicate that the recombinant enzyme expressed in microbial systems was unstable due to the lack of normal glycosylation and/or the presence of endogenous cytoplasmic or periplasmic proteases.

Efforts to express this enzyme in eukaryotic expression systems were equally difficult for different reasons. The α-Gal A is a lysosomal enzyme encoded by a "housekeeping" gene. The primary translation product is highly modified and processed, requiring a complex series of events involving cleavage of a signal sequence, glycosylation, phosphorylation, and sialylation, which can be properly effected only by appropriate host cells. Moreover, since the expression product is destined for the lysosome, which remains intracellular, it is quite surprising that the methods described herein allow for the secretion of a properly processed, biologically active molecule.

The biologically active α-Gal A produced in accordance with the invention has a variety of uses, probably the most significant being its use in enzyme replacement therapy for the lysosomal storage disorder, Fabry disease. For example, the metabolic defect in cultured fibroblasts from Fabry disease can be corrected in vitro by the addition of exogenous α-Gal A into the culture medium. In addition, limited human trials have demonstrated the biochemical effectiveness of enzyme replacement to deplete the circulating substrate prior to vascular deposition. However, prior to the present invention, large quantities of biologically active, purified human α-Gal A could not be produced for use in replacement therapies. The α-Gal A produced in accordance with the invention also has a number of industrial uses, e.g., in any process involving the hydrolysis of α-D-galactosyl glycoconjugates, the conversion of blood group B to group O, etc., as described herein.

The invention is divided into the following sections solely for the purpose of description:

(a) the coding sequence for α-Gal A; (b) construction of an expression vector which will direct the expression of the enzyme coding sequence;

(c) transfection of appropriate host cells which are capable of replicating, translating and properly processing the primary transcripts in order to express a biologically active gene product; and (d) identification and/or purification of the enzyme so produced. Once a transformant is identified that expresses high levels of biologically active enzyme, the practice of the invention involves the expansion and use of that clone in the production and purification of biologically active α-Gal A.

The invention is demonstrated herein, by way of examples in which cDNAs of α-Gal A were cloned and expressed in a mammalian expression system. Modifications to the cDNA coding sequences which improve yield, and simplify purification without detracting from biological activity are also described. Further, modifications to the host cells are described that allow for the expression of sialylated and asialylated glycoforms of the enzyme, both of which may be easily purified. Although the invention is described for α-Gal A, the methods and modifications explained may be analogously applied to the expression of other secreted proteins, and in particular, other lysosomal enzymes, including but not limited to α-N-acetylgalactosaminidase, and acid sphingomyelinase.

Various aspects of the invention are described in more detail in the subsections below and in the examples that follow.

5.1. THE α-GAL A CODING SEQUENCE

The nucleotide coding sequence and deduced amino acid sequence for α-Gal A is depicted in FIGS. 1A–1C. This nucleotide sequence, or fragments or functional equivalents thereof, may be used to generate recombinant DNA molecules that direct the expression of the enzyme product, or functionally active peptides or functional equivalents thereof, in appropriate host cells.

Due to the degeneracy of the nucleotide coding sequence, other DNA sequences which encode substantially the same amino acid sequences as depected in FIGS. 1A–1C may be used in the practice of the invention for the cloning and expression of α-Gal A. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The coding sequences for α-Gal A may be conveniently obtained from genetically engineered microorganisms or cell lines containing the enzyme coding sequences, such as the deposited embodiments described herein. Alternatively, genomic sequences or cDNA coding sequences for these enzymes may be obtained from human genomic or cDNA libraries. Either genomic or cDNA libraries may be prepared from DNA fragments generated from human cell sources. The fragments which encode α-Gal A may be identified by screening such libraries with a nucleotide probe that is substantially complementary to any portion of the sequence depicted in FIGS. 1A–1C. Indeed, sequences generated by polymerase chain reaction can be ligated to form the full-length sequence. Although portions of the coding sequences may be utilized, full length clones, i.e., those containing the entire coding region for α-Gal A, may be preferable for expression. Alternatively, the coding sequences depicted in FIG. 1A may be altered by the addition of sequences that can be used to increase levels of expression and/or to facilitate purification. For example, as demonstrated in the working embodiments described herein, the α-Gal A coding sequence was modified by the addition of the nucleotide sequence encoding the cleavage site for collagenase followed by the Staphylococcal Protein A. Exression of this chimeric gene construct resulted in a fusion protein consisting of α-Gal A-the collagenase substrate—Protein A. This fusion protein was readily purified using an IgG column which binds to the Protein A moiety. Unfused α-Gal A was released from the column by treatment with collagenase which cleaved the α-Gal A from the Protein A moiety bound to the column. Other enzyme cleavage substrates and binding proteins can be engineered into similar constructs for the production of α-Gal A which can be readily purified and released in its biologically active form.

Techniques well-known to those skilled in the art for the isolation of DNA, generation of appropriate restriction fragments, construction of clones and libraries, and screening recombinants may be used. For a review of such techniques, see, for example, Sambrook, et al., 1989, Molecular Cloning A Laboratory Manual, 2nd Ed. Cold Spring Harbor Press, New York, Chapters 1–18.

In an alternate embodiment of the invention, the coding sequence of FIGS. 1A–1C could be synthesized in whole or in part, using chemical methods well-known in the art. See, for example, Caruthers, et. al., 1980, Nuc. Acids Res. Symp. Ser. 7: 215–233; Crea & Horn, 1980, Nuc. Acids Res. 9(10): 2331; Matteucchi & Carruthers, 1980, Tetrahedron Letters 21: 719; and Chow and Kempe, 1981, Nuc. Acids Res. 9(12): 2807–2817.

Alternatively, the protein itself could be produced using chemical methods to synthesize the amino acid sequence depicted in FIGS. 1A–1C in whole or in part. For example, peptides can be synthesized by solid phase techniques, cleaved from the resin and purified by preparative high performance liquid chromatograph. (E.g., see, Creighton, 1983, Proteins, Structures and Molecular Principles, W. H. Freeman & Co., New York pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman & Co., New York, pp. 34–49).

Human α-Gal A is a homodimeric glycoprotein. The full-length α-Gal A cDNA predicts a mature subunit of 398 amino acids. The amino acid sequence has an overall homology of about 50% with human α-N-acetylgalactosaminidase (α-Gal B). Homology searches with computerized data bases revealed short regions of α-Gal A homology with the yeast Mel 1 and the *E. coli* Mel A amino acid sequences (see FIGS. 1D–1F). It is likely that these conserved regions are important for enzyme conformation, stability, subunit association and/or catalysis. Thus, it is preferred not to alter such conserved regions. However, certain modifications in the coding sequence may be advantageous. For example, the four N-linked glycosylation consensus sequences could be selectively obliterated, thereby altering the glycosylation of the enzyme and affecting phosphorylation, sialylation, sulfation, etc. Such modified enzymes may have altered clearance properties and targeting when injected into Fabry patients.

Oligosaccharide modifications may be useful in the targeting of α-Gal A for effective enzyme therapy. Some examples of such modifications are described in more detail infra. Previous studies demonstrated that the plasma glycoform of α-Gal A, which is more highly sialylated than the splenic glycoform, was more effective in depleting the toxic accumulated circulating substrate from Fabry patients (Desnick et al., 1977, Proc. Natl. Acad. Sci. U.S.A. 76:5326–5330). Studies characterizing the purified splenic and plasma glycoforms of the enzyme revealed differences only in their oligosaccharide moieties (Desnick et al., 1977, Proc. Natl. Acad. Sci. U.S.A. 76:5326–5330). Thus, efforts to target the recombinant enzyme for effective treatment of Fabry disease may be enhanced by modification of the N-glycosylation sites.

Also, the 5' untranslated and coding regions of the nucleotide sequence could be altered to improve the translational efficiency of the α-Gal A mRNA. For example, substitution of a cytosine for the guanosine in position +4 of the α-Gal A cDNA could improve the translational efficiency of the α-Gal A mRNA 5- to 10-fold (Kozak, 1987, J. Mol. Biol. 196:947–950).

In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered into the α-Gal A enzyme to produce a more active or stable protein, more enzyme protein, or even change the catalytic specificity of the enzyme.

5.2. PRODUCTION OF RECOMBINANT α-Gal A

In order to express a biologically active α-Gal A, the coding sequence for the enzyme, a functional equivalent, or a modified sequence, as described in Section 5.1., supra, is inserted into an appropriate eukaryotic expression vector, i.e., a vector which contains the necessary elements for transcription and translation of the inserted coding sequence in appropriate eukaryotic host cells which possess the cellular machinery and elements for the proper processing, i.e., signal cleavage, glycosylation, phosphorylation, sialylation, and protein sorting. Mammalian host cell expression systems are preferred for the expression of biologically active enzymes that are properly folded and processed; when administered in humans such expression products should exhibit proper tissue targeting and no adverse immunological reaction.

5.2.1. CONSTRUCTION OF EXPRESSION VECTORS AND PREPARATION OF TRANSFECTANTS

Methods which are well-known to those skilled in the art can be used to construct expression vectors containing the α-Gal A coding sequence and appropriate transcriptional/translational control signals. These methods include in vitro recombination/genetic recombination. See, for example, the techniques described in Maniatis et al., 1982, Molecular Cloning A Laboratory Manual, Cold spring Harbor Laboratory, New York, Chapter 12.

A variety of eukaryotic host-expression systems may be utilized to express the α-Gal A coding sequence. Although prokaryotic systems offer the distinct advantage of ease of manipulation and low cost of scale-up, their major drawback in the expression of α-Gal A is their lack of proper post-translational modifications of expressed mammalian proteins. Eukaryotic systems, and preferably mammalian expression systems, allow for proper modification to occur. Eukaryotic cells which possess the cellular machinery for proper processing of the primary transcript, glycosylation, phosphorylation, and, advantageously secretion of the gene product should be used as host cells for the expression of α-Gal A. Mammalian cell lines are preferred. Such host cell lines may include but are not limited to CHO, VERO, BHK, HeLa, COS, MDCK, –293, WI38, etc. Alternatively, eukaryotic host cells which possess some but not all of the cellular machinery required for optional processing of the primary transcript, and/or post-translational processing and/or secretion of the gene product may be modified to enhance the host cell's processing capabilities. For example, a recombinant nucleotide sequence encoding a peptide product that performs a processing function the host cell had not previously been capable of may be engineered into the host cell line. Such a sequence may either be co-transfected into the host cell along with the gene of interest, or included in the recombinant construct encoding the gene of interest. Alternatively, cell lines containing this sequence may be produced which are then transfected with the gene of interest.

Appropriate eukaryotic expression vectors should be utilized to direct the expression of α-Gal A in the host cell chosen. For example, at least two basic approaches may be followed for the design of vectors on SV40. The first is to replace the SV40 early region with the gene of interest while the second is to replace the late region (Hammarskjold, et al., 1986, Gene 43: 41). Early and late region replacement vectors can also be complemented in vitro by the appropriate SV40 mutant lacking the early or late region. Such complementation will produce recombinants which are packaged into infectious capsids and which contain the α-Gal A gene. A permissive cell line can then be infected to produce the recombinant protein. SV40-based vectors can also be used in transient expression studies, where best results are obtained when they are introduced into COS (CV-1, origin of SV40) cells, a derivative of CV-1 (green monkey kidney cells) which contain a single copy of an origin defective SV40 genome integrated into the chromosome. These cells actively synthesize large T antigen (SV40), thus initiating replication from any plasmid containing an SV40 origin of replication.

In addition to SV40, almost every molecularly cloned virus or retrovirus may used as a cloning or expression vehicle. Viral vectors based on a number of retroviruses (avian and murine), adenoviruses, vaccinia virus (Cochran, et al., 1985, Proc. Natl. Acad. Sci. U.S.A. 82: 19) and polyoma virus may be used for expression. Other cloned viruses, such as JC (Howley, et al., 1980, J. Virol 36: 878), BK and the human papilloma viruses (Heilman, et al., 1980, J. Virol 36: 395), offer the potential of being used as eukaryotic expression vectors. For example, when using adenovirus expression vectors the α-Gal A coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the human enzyme in infected hosts (e.g., see Logan & Shenk, 1984, Proc. Natl. Acad. Sci. (U.S.A.) 81: 3655–3659). lternatively, the vaccinia virus 7.5K promoter may be used. (e.g., see, Mackett et al., 1982, Proc. Natl. Acad. Sci. (U.S.A.) 79: 7415–7419; Mackett et al., 1984, J. Virol. 49: 857–864; Panicali et al., 1982, Proc. Natl. Acad. Sci. 79: 4927–4931). Of particular interest are vectors based on bovine papilloma virus (Sarver, et al., 1981, Mol. Cell. Biol. 1: 486). These vectors have the ability to replicate as extrachromosomal elements. Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters such as the metallothionine IIA promoter, heat shock promoters, etc.

For long-term, high-yield production of recombinant proteins, stable expression is preferred. For example, following the introduction of foreign DNA, engineered cells may be allowed to grow for 1–2 days in an enriched media, and then are switched to a selective media. Rather than using expression vectors which contain viral origins of replication, host cells can be transformed with the α-Gal A or DNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. U.S.A. 48: 2026), and adenine phosphoribosyltransferase (Lowy, et al., 1980, Cell 22: 817) genes can be employed in tk⁻, hgprt⁻ or aprt⁻ cells respectively. Also, antimetabolite resistance can be used as the basis of selection for dhfr, which confers resistance to methotrexate (Wigler, et al., 1980, Natl. Acad. Sci. U.S.A. 77: 3567; O' Hare, et al., 1981, Proc. Natl. Acad. Sci. U.S.A. 78: 1527); gpt, which confers resistance to mycophenolic acid (Mulligan & Berg, 1981, Proc. Natl. Acad. Sci. U.S.A. 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. U.S.A. 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Alternative eukaryotic expression systems which may be used to express the α-Gal A enzymes are yeast transformed with recombinant yeast expression vectors containing the α-Gal A coding sequence; insect cell systems infected with recombinant virus expression vectors (e.g., baculovirus) containing the α-Gal A coding sequence; or plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the α-Gal A coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, New York, Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, New York, Vol. 152, pp. 673–684; and The Molecular Biology of the Yeast Saccharomyces, 1982, Eds. Strathern et al., Cold Spring Harbor Press, Vols. I and II. For complementation assays in yeast, cDNAs for α-Gal A may be cloned into yeast episomal plasmids (YEp) which replicate autonomously in yeast due to the presence of the yeast 2μ circle. The cDNA may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. D. M. Glover, 1986, IRL Press, Wash., D.C.). Constructs may contain the 5' and 3' non-translated regions of the cognate α-Gal A mRNA or those corresponding to a yeast gene. YEp plasmids transform at high efficiency and the plasmids are extremely stable. Alternatively, vectors may be used which promote integration of foreign DNA sequences into the yeast chromosome.

In cases where plant expression vectors are used, the expression of the α-Gal A coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9.

An alternative expression system which could be used to express α-Gal A is an insect system. In one such system, *Autographa californica* nuclear polyhedrosis virus (AcNPV) is used as a vector to express foreign genes. The virus grows in *Spodoptera frugiperda* cells. The α-Gal A sequence may be cloned into non-essential regions (for example the polyhedrin gene) of the virus and placed under control of an ACNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

5.2.2. IDENTIFICATION OF TRANSFECTANTS OR TRANSFORMANTS EXPRESSING THE α-Gal A PRODUCT

The host cells which contain the α-Gal A coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of α-Gal A mRNA transcripts in the host cell; and (d) detection of the gene product as measured by immunoassay or by its biological activity.

In the first approach, the presence of the α-Gal A coding sequence inserted in the expression vector can be detected by DNA-DNA or DNA-RNA hybridization using probes comprising nucleotide sequences that are homologous to the α-Gal A coding sequence substantially as shown in FIGS. 1A–1C, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the α-Gal A coding sequence is inserted within a marker gene sequence of the vector, recombinants containing the α-Gal A coding sequence can be identified by the absence of the marker gene function. Alternatively, a marker gene can be placed in tandem with the α-Gal A sequence under the control of the same or different promoter used to control the expression of the α-Gal A coding sequence. Expression of the marker in response to induction or selection indicates expression of the α-Gal A coding sequence.

In the third approach, transcriptional activity for the α-Gal A coding region can be assessed by hybridization assays. For example, RNA can be isolated and analyzed by Northern blot using a probe homologous to the α-Gal A coding sequence or particular portions thereof substantially as shown in FIGS. 1A–1C. Alternatively, total nucleic acids of the host cell may be extracted and assayed for hybridization to such probes.

In the fourth approach, the expression of the —Gal A protein product can be assessed immunologically, for example by Western blots, immunoassays such as radioimmuno-precipitation, enzyme-linked immunoassays and the like. The ultimate test of the success of the expression system, however, involves the detection of the biologically active α-Gal A gene product. Where the host cell secretes the gene product, the cell free media obtained from the cultured transfectant host cell may be assayed for α-Gal A activity. Where the gene product is not secreted, cell lysates may be assayed for such activity. In either case, a number of assays can be used to detect α-Gal A activity including but not limited to: (a) assays employing the synthetic fluorogenic or chromogenic α-D-galactosides such as 4-methylumbelliferyl-α-D-galactopyranoside (Desnick et al., 1973, J. Lab. Clin. Invest. 81:157); (b) assays employing the radiolabeled or fluorescent labeled natural substrates such as tritiated globotriaosyl ceramide or pyrene-dodecanoyl-sphingosine-trihexoside (Bishop and Desnick, 1981, J. Biol. Chem. 256:1307); and (c) assays employing X-α-gal.

5.2.3. PURIFICATION OF THE α-GAL A GENE PRODUCT

Once a clone that produces high levels of biologically active α-Gal A is identified, the clone may be expanded and used to produce large amounts of the enzyme which may be purified using techniques well-known in the art including, but not limited to immunoaffinity purification, chromatographic methods including high performance liquid chromatography and the like. Where the enzyme is secreted by the cultured cells, α-Gal A may be readily recovered from the culture medium.

As demonstrated in the working examples described infra, recombinant α-Gal A was purified from the crude media by affinity chromatography on α-GalNH$_2$—C$_{12}$Sepharose followed by hydrophobic chromatography on Octyl Sepharose and gel filtration on a 100 cm Superose 6 column. The recombinant enzyme was essentially homogeneous following the gel filtration step and was >98% pure as judged by SDS-PAGE.

Human recombinant α-Gal A was purified to homogeneity from the media of the CHO cell line, DG5.3, which was shown to secrete most of the recombinant enzyme. The culture media from this clone was highly enriched for α-Gal A when serum-free medium was used, constituting greater than 95% of the total extracellular protein. Thus, purification to homogeneity could be accomplished in only three chromatographic steps. Over half a gram of enzyme was produced in three months and from a portion of this, 280 mg was purified with a yield of 80% using only laboratory-scale equipment. Notably, the recombinant enzyme had full enzymatic activity with a specific activity equal to that of the previously purified human enzyme (Bishop, et al., 1978, Biochim. Biophys. Acta. 525: 399; Bishop and Desnick, 1981, J. Biol. Chem. 256:1307). The recombinant enzyme was able to recognize and effectively cleave an analog of the natural substrate, globotriaosylceramide.

Where the α-Gal A coding sequence is engineered to encode a cleavable fusion protein, the purification of α-Gal A may be readily accomplished using affinity purification techniques. In the working examples described infra, a collagenase cleavage recognition consensus sequence was engineered between the carboxy terminus of α-Gal A and protein A. The resulting fusion protein was readily purified using an IgG column that bound the protein A moiety. Unfused α-Gal A was readily released from the column by treatment with collagenase.

In particular, the overlap extension method (Ho, et al., 1989, Gene 77: 51; Kadowaki, et al., 1989, Gene 76: 161) was used to fuse the full-length α-Gal A cDNA to the protein A domain E of *Staphylococcus aureus*. Following transfection by electroporation, the α-Gal A activity in COS-1 cell extracts was increased 6 to 7-fold. In addition, the transfected cells secreted significant amounts of the fusion protein into the culture media (400 U/ml). The secreted fusion protein was rapidly purified by a single IgG affinity purification step. The engineering of a collagenase cleavage recognition consensus sequence between these two polypeptides facilitated the cleavage of the fusion protein so that the purified human α-Gal A polypeptide could be readily separated from the protein A domain by a second IgG purification step. Of interest was the fact that the fusion construct retained α-Gal activity, presumably indicating that the enzyme polypeptide formed the active homodimeric configuration even though the carboxy terminus was joined to an additional 56 residues of the protein A domain. Since COS-1 cells transfected with an α-Gal A construct exhibit similar levels of expression and distribution between cells and media it appears that the protein A domain does not interfere with either the folding or the proper processing of this lysosomal enzyme. Furthermore, the presence of the dimerized α-Gal A polypeptide did not inhibit the binding of the protein A domain to the IgG affinity column. The insertion of the four residue collagenase cleavage recognition sequence between the α-Gal A and protein A polypeptides permited cleavage of the fusion protein leaving only two of the collagen residues on each of the peptides.

The ease of cDNA construction using the polymerase chain reaction, transfection and purification of the expressed protein permits the isolation of small, but sufficient amount of α-Gal A for characterization of the enzyme's physical and kinetic properties. Using site-directed mutagenesis or naturally occuring mutant sequences, this system provides a reasonable approach to determine the effects of the altered primary structure on the function of the protein. Fusion constructs with the protein A domain E preceeding the amino terminus and the following the carboxy terminus may also be engineered to evaluate which fusion construct will interfere the least, if at all, with the protein's biologic function and the ability to bind IgG.

Using this aspect of the invention, any cleavage site or enzyme cleavage substrate may be engineered between the α-Gal A sequence and a second peptide or protein that has a binding partner which could be used for purification, e.g., any antigen for which an immunoaffinity column can be prepared.

5.2.4. CHARACTERIZATION OF THE RECOMBINANT ENZYME

The purified recombinant enzyme produced in the mammalian expression systems described herein (e.g., the CHO expression system), had molecular weight, pH optimum, km and isoelectric point values which were essentially identical to those of the enzyme purified from the human plasma (Bishop, et al., 1978, Biochim. Biophys. Acta. 525: 399; Bishop and Desnick, 1981, J. Biol. Chem. 256:1307). Analysis of the carbohydrate moieties on this enzyme revealed the presence of three oligosaccharide chains on the α-Gal A polypeptide. These chains were a mixture of complex, hybrid and high-mannose types as evidenced by endoglycosidase and QAE Sephadex studies. Most importantly, the recombinant enzyme was also similar to the native plasma form of α-Gal A in having terminal sialic acid moieties (Bishop & Desnick, 1981, J Biol. Chem. 256: 1307). In the limited clinical trial described supra, the plasma form of the enzyme was shown to be more effective in degrading circulating $GbOse_3Cer$ than the splenic form. Therefore, the recombinant enzyme or a modified recombinant enzyme, including but not limited to modifications of its carbohydrate chains or amino acid sequence, may be the most appropriate form for enzyme replacement therapy of Fabry disease. Indeed, the saturable uptake of recombinant α-Gal A by Fabry and normal fibroblasts is demonstrated in the examples herein, and is shown to be specifically inhibited by 2 mM mannose-6-phosphate.

In addition, the CHO expression system described herein has great promise for studies of the cell biology of lysosomal biogenesis and glycohydrolase processing. Light microscopy revealed highly vacuolated cytoplasm in the DG5.3 CHO cells suggesting a proliferation of lysosomal membranes and offering the potential for analysis of lysosomal biogenesis. Preliminary studies have indicated that the recombinant enzyme is synthesized very rapidly, exits the endoplasmic reticulum in 5–10 min following its synthesis and is secreted 45–60 min later. These fast kinetics of recombinant α-Gal A biosynthesis allow for interesting studies involving lysosomal enzyme biosynthesis and offer a methodology that, to date, is only rivaled by viral systems. In fact, recombinant α-Gal A is synthesized so rapidly that a single radioactive pulse of 3 min is sufficient to label enough enzyme for these studies. The unexpectedly specific secretion of only the overproduced recombinant α-Gal A and not other lysosomal enzymes appears analogous to "gene dosage-dependant secretion" described by Rothman, et al. (Stevens et al., 1986, J. Cell Biol. 102:1551; Rothman et al., 1986, Proc. Natl. Acad. Sci. U.S.A. 83:3248) and poses interesting questions which can be evaluated in this system.

5.2.5. MODIFIED GLYCOFORMS OF RECOMBINANT α-Gal A FOR ENZYME THERAPY IN FABRY DISEASE

Initial experiments to assess the clearance kinetics and tissue distribution of recombinant α-Gal A in mice revealed 50% targeting to the liver with the remaining enzyme being distributed to many other tissues including significant targeting to kidney, heart and skin. While this distribution is similar to that previously observed for the plasma form of human α-Gal A in mice, it may be appropriate to modify the enzyme for altered tissue targeting. Modifications of the recombinant α-Gal A to enhance tissue targeting including selective deglycosylation of the complex and high mannose carbohydrate moieties covalently attached to the recombinant enzyme. In particular, the invention includes modification of host cells that allow for expression of sialylated and asialylated glycoforms of the enzyme, both of which may be easily purified (see Section 9 infra). For example, when using CHO cells to express α-Gal A, the CHO cells may be co-transfected with sialyl-transferase gene construct that supplies the missing function to the CHO cell in order to express the sialylated glycoform of α-Gal A.

Alternatively, sequential deglycosylation to various glycoforms for use in the treatment of Fabry disease. Such modifications have proven to be important in effectively targeting β-glucocerebrosidase to macrophages in the treatment of Gaucher disease (Barton, N. W., et al., 1990, Proc. Natl. Acad. Sci. U.S.A. 87: 1913). In this case, placenta derived β-glucocerebrosidase was sequentially treated with neuraminidase, β-galactosidase and N-β-acetylglucosaminidase to expose terminal mannose residues for uptake by the mannose receptor of these cells (Stahl, et al., in The Molecular Basis of Lysosomal Disorders, Barranger, J. A. and Brady, R. O. eds., 1984 Academic Press, New York pp. 209–218).

Modifications to human recombinant α-Gal A included in the scope of this invention include, but are not limited to, sequential deglycosylation by neuraminidase to expose terminal galactose; β-galactosidase treatment to expose N-β-acetylglucosaminyl residues; and N-β-acetylglucosaminidase treatment to expose mannose residues for specific targeting and uptake by various cell types. The sequentially deglycosylated recombinant α-Gal A glycoforms may be analyzed by determining the clearance kinetics and tissue distribution of each of the radiolabeled glycoforms following intravenous administration in mice and monkeys.

Deglycosylation of recombinant α-Gal A may be accomplished in a number of ways. The general methods of sequential treatment by exo-glycosidases which may be used are essentially those previously described (Murray, G. J., 1987, Meth. Enzymol, 149: 25). For example, terminal sialic acid residues can be removed by treatment with neuraminidase covalently bound to agarose; e.g., type VI neuraminidase attached to agarose (SIGMA Chemical Co., St. Louis, Mo.) may be used at 40 U/g to treat 100 mg α-Gal A with 8 units of conjugated neuraminidase at pH 5.0 for 4 hour at 37° C. The conjugated neuraminidase can be removed by centrifugation. Similarly, β-galactosidase (3 Units per 100 mg α-Gal A) purified from Streptococcus pneumoniae may be used to remove terminal galactose residues. Finally, jack bean N-β-acetylglucosaminidase (SIGMA Chemical Co., St. Louis, Mo.) can be used; e.g., $3 \times 10^6$ units can be mixed with each 100 mg aliquot of the recombinant α-Gal A for four hours at 37° C. At each step, the recombinant enzyme can be rapidly purified free of deglycosylating enzymes and free carbohydrate by purification over the α-galactosylamine-Sepharose affinity column.

For the analysis of the in vivo fate of the various glycoforms, including plasma clearance kinetics and tissue distribution studies, the recombinant α-Gal A may be labeled prior to modification. For example, the recombinant α-Gal A can be radiolabelled by growth in the CHO DG5.3 cell line in the presence of 50 μCi/ml [$^{35}$S]methionine (>1000 Ci/mmole) for 24 hours. The secreted radiolabeled enzyme can be purified from the harvested media by α-galactosylamine-Sepharose affinity chromatography as previously described. Essentially 100% of the radiolabelled protein secreted by these cells is α-Gal A which can then be used for the sequential generation of the glycoforms.

5.3. USES OF THE RECOMBINANT α-Gal A

The purified products obtained in accordance with the invention may be advantageously utilized for enzyme replacement therapy in patients with the lysosomal storage disorder, Fabry Disease. Alternatively, the purified products obtained in accordance with the invention may be used in vitro to modify α-D-galacto-glycoconjugates in a variety of processes; e.g., to convert blood group B erythrocytes to blood group O; in commercial processes requiring the converion of sugars such as raffinose to sucrose or melibiose to galactose and glucose; etc. These are discussed in more detail in the subsections below.

5.3.1. α-Gal A ENZYME THERAPY IN FABRY DISEASE

Among the inborn errors of metabolism, studies of patients with lysosomal storage disorders have provided basic understanding of the biology of the lysosomal apparatus and its hydrolases, their biosynthesis and processing (Rosenfeld, et al., 1982, J. Cell Biol. 93: 135; Lemansky, et al., 1984, J. Biol. Chem. 259: 10129), the mechanisms of their transport to the lysosomes (Neufeld, et al., 1975, Ann. Rev. Biochem. 44: 357; Sly et al., 1982, J. Cell Biochem. 18:67; Kornfeld, S., 1986, J. Clin. Invest. 77: 1), and their cofactor requirements (Verheijen, et al., 1985. Eur. J. Biochem. 149: 315; d'Azzo, et al., 1982, Eur. J. Biochem. 149:315; Mehl, et al., 1964, Physiol. Chem. 339: 260; Conzelman, et al., 1978, Proc. Natl. Acad. Sci. U.S.A. 75: 3979). Of the over 30 lysosomal storage disorders, Fabry disease is an ideal candidate for the application of the recombinant DNA techniques described herein to evaluate and utilize various therapeutic approaches in model systems, as well as to correlate the effects of site-specific changes on enzyme structure and function. The disease has no central nervous system involvement; thus, the blood/brain barrier does not present an obstacle to enzyme replacement therapy. The defective enzyme, α-Gal A, is a homodimer (Bishop & Desnick, 1981, J. Biol. Chem. 256: 1307), in contrast to some lysosomal enzymes which have different subunits such as β-hexosaminidase A (Mahuran, et al., 1982, Proc. Natl. Acad. Sci. U.S.A. 79: 1602); therefore, only a single gene product must be obtained. The metabolic defect in cultured fibroblasts from Fabry disease has been corrected in vitro by the addition of exogenous enzyme into the culture medium (Cline, et al., 1986, DNA 5: 37). Also, atypical variants with Fabry disease have been identified, these males are clinically asymptomatic, having sufficient residual α-Gal A activity (3 to 10%) to protect them from the major morbid manifestations of the disease (Lemansky, et al., 1987, J. Biol. Chem. 262:2062; Clarke, et al., 1971, N. Engl. J. Med. 284: 233; Romeo, et al., 1975, Biochem. Genet. 13: 615; Bishop, et al., 1981, Am. J. Hum. Genet. 71: 217A; Bach, et al., 1982, Clin. Genet. 21: 59; and, Kobayashi, et al., 1985, J. Neurol. Sci. 67: 179). Finally, as noted above, limited human trials have demonstrated the biochemical effectiveness of enzyme replacement to deplete the circulating substrate prior to vascular deposition as well as the absence of immunologic complications (Brady, et al., 1973, N. Engl. J. Med. 289: 9; Desnick, et al., 1979, Proc. Natl. Acad. Sci. U.S.A. 76:5326; Bishop, et al., 1981, Enzyme Therapy XX: In: Lysosomes and Lysosomal Storage Diseases, Callahan, J. W. and Lowden, J. A., (eds.), Raven Press, New York, pp. 381; Desnick, et al., 1980, Enzyme Therapy XVII: In: Enzyme Therapy in Genetic Disease: 2, Desnick, R. J. (ed.), Alan, R. Liss, Inc., New York, pp. 393).

In these studies, both splenic and plasma isoforms of the α-Gal A enzyme were administered intravenously. The circulating half-life of the splenic isozyme was about 10 min whereas that for the plasma isozyme was approximately 70 min. After each dose of the splenic isozyme, the concentration of the accumulated circulating substrate decreased maximally in 15 min. In contrast, injection of the plasma isozyme decreased circulating substrate levels gradually over 36–72 hours. Since the secreted form of the recombinant α-Gal A appears to be similar to the plasma isozyme, the secreted form of the recombinant enzyme could be effective for the long term depletion and control of circulating substrate levels.

The dose of the partially purified plasma and splenic isozymes administered in the above clinical trials was 2000 U/kg body weight, or a dose equivalent to giving 1 μg/kg of pure enzyme. Since this dose proved effective in reducing the level of circulating substrate, a similar dose of the recombinant enzyme should have a similar effect. However, the recombinant enzyme could be administered at a dosage ranging from 0.1 μg/kg to about 10 mg/kg and, preferably from about 0.1 mg/kg to about 2 mg/kg. The ability to produce large amounts of the recombinant enzyme in accordance with this invention will permit the evaluation of the therapeutic effect of significantly larger doses.

5.3.2. IN VITRO USES OF α-Gal A

α-Gal A is a galactosyl hydrolase which has activity toward various oligosaccharides, glycoproteins, glycopeptides and glycolipids with terminal α-galactosidic linkages. Thus, the enzyme can be used in vitro to modify these α-galacto-glycoconjugates. For example, the recombinant α-Gal A of the invention could be utilized for a variety of desirable modifications including but not limited to: (a) the conversion of blood group B erythrocytes to cells expressing the blood group O antigen (Harpaz, et al., 1977, Eur. J. Biochem. 77:419–426); and (b) the hydrolysis of stacchyose to raffinose, raffinose to the disaccharide sucrose, or the hydrolysis of melibiose to galactose and glucose (Silman, et al., 1980, Biotechnol. Bioeng. 22:533). Such hydrolyses have commercial applications as in the degradation of molasses as a substrate for yeast production (Liljestrom-Suominen, et al., 1988, Appl. Environ. Micro. 54:245–249).

EXAMPLE: OVEREXPRESSION AND SPECIFIC SECRETION OF BIOLOGICALLY ACTIVE α-GALACTOSIDASE A IN A MAMMALIAN CELL SYSTEM

The subsections below describe the production of large quantities of human recombinant α-Gal A. A full-length cDNA encoding human α-Gal A was inserted into the expression vector p91023(B) in front of the amplifiable dihydrofolate reductase (DHFR) cDNA. The functional integrity of cDNA construct (p91-AGA) was confirmed by transient expression of active enzyme in COS-1 cells; 650 U/mg (nmol/hour) versus endogenous levels of ~150 U/mg of 4-MU-α-D-galactopyranoside activity. The p91-AGA construct was introduced by electroporation into DG44 dhfr⁻ CHO cells. Positive selection in media lacking nucleosides resulted in the isolation of clones expressing the active enzyme at levels ranging from 300 to 2,000 U/mg. Selected subclones, grown in increasing concentrations of methotrexate (MTX, 0.02 to 1.3 $\mu$M) to co-amplify DHFR and α-Gal A cDNAs, expressed intracellular levels of α-Gal A activity ranging from 5,000 to 25,000 U/mg. Notably, subclone DG44.5, which expressed high intracellular levels of α-Gal A, secreted more than 80% of the total recombinant enzyme produced. At a MTX concentration of 500 $\mu$M, $10^7$ cells secreted ~15,000 U/ml culture media/day. Of note, endogenous CHO lysosomal enzymes were not secreted including β-hexosaminidase, α-mannosidase, β-galactosidase and β-glucuronidase, indicating that the secretion was α-Gal A specific and not due to saturation of the mannose-6phosphate receptor-mediated pathway. Using a hollow fiber bioreactor, up to 5 mg per liter per day of recombinant α-Gal A enzyme was produced per day. The secreted α-Gal A was purified by affinity chromatography for characterization of various physical and kinetic properties. The recombinant α-Gal A had a pI, electrophoretic mobility and Km values which were similar to the enzyme purified from human plasma. In addition, $^{32}$p labeling studies revealed that both the lysosomal and secreted forms were phosphorylated, presumably in their oligosaccharide moieties. Current studies are directed to characterize additional kinetic and physical properties, the oligosaccharide moieties and the crystal structure of the recombinant enzyme. Furthermore, the availability of large amounts of soluble active enzyme will permit the evaluation of enzyme replacement in animal systems prior to clinical trials in hemizygotes with Fabry disease.

6.1. MATERIALS AND METHODS

6.1.1. MATERIALS

Restriction endonucleases, the Klenow fragment of DNA polymerase I, T4 polymerase and T4 ligase were from New England Biolabs; αand γ-32[P] dNTPs (3000 Ci/mole) and α35[S]dATP (100 Ci/mole) were from Amersham. The COS-1 cell line was purchased from ATCC, Rockville, Md. The CHO DG44 dhfr⁻ cell line is described (Urlaug, et al., 1986, Somat. Cell Genet. 12:555–566).

6.1.2. CONSTRUCTION OF EXPRESSION VECTOR p91-AGA

Plasmid pcDAG126 (Bishop, et al., 1988, in, Lipid Storage Disorders, Salvayre, R., Douste-Blazy, L. Gatt, S. Eds. Plenum Publishing Corporation, New York, pp. 809 to 822) containing the full-length α-Gal A cDNA was digested with Bam HI and Pst I and the 1.45 kb insert fragment was purified by agarose gel elctrophoresis. The cDNA was then force-subcloned into plasmid pGEM-4 at the Bam HI and Pst I sites resulting in pGEM-AGA126. This plasmid was then digested with Hind III, end-filled using Klenow and ligated to Eco RI linkers. After digestion with Eco RI, the 1.45 kb fragment was purified as above and cloned into the Eco RI site of the mammalian expression vector p91023(B) (Wong et al., 1985, Science 228:810) resulting in p91-AGA (FIG. 1G).

6.1.3. CELL CULTURE, ELECTROTRANSFECTION, AND GENE AMPLICATION

COS-1 and DG44 CHO cells were maintained at 37° C. in 5% $CO_2$ in Dulbecco's modified Eagle's medium (DMEM) with 10% fetal calf serum (FCS) and antibiotics; DG44 (dhfr⁻) cells were maintained by addition of 0.05 mM hypoxanthine and 0.008 mM thymidine to the media. Following transfection, the recombinant CHO lines were grown in DMEM supplemented with 10% dialyzed FCS in the absence or presence of MTX.

For electroporation, cells were trypsinized and centrifuged at 800×g at room temperature for 10 min. The pellet was washed once with DMEM supplemented with 10% FCS serum and twice in ice-cold electroporation buffer (phosphate buffered sucrose; 272 mM sucrose, 7 mM sodium phosphate, pH 7.4, containing 1 mM $MgCl_2$). Cells were then resuspended in phosphate buffered sucrose at ~0.65 to 1.0×10⁷/ml. The cell suspension (0.8 ml) was placed in a 0.4 cm gap cuvette (Bio-Rad), 5–20 $\mu$g of plasmid DNA was added and kept on ice for 10 min. The cuvette was placed in the "Gene Pulser" chamber (Bio-Rad) and pulsed once at 25 $\mu$F with 300 V for COS-1 cells or 400 V for CHO DG44 (dhfr⁻) cells, the optimized settings for the respective cell lines. The cuvette containing the pulsed cells was placed on ice for 10 min and then the cells were removed from the cuvette and placed in 15 ml of DMEM supplemented with 10% FCS.

For transient expression, COS-1 cells were harvested at 72 hours and assayed immediately. For stable expression, the transfected DG44 cells were grown for 48 hours and then were removed from the culture dish by trypsinization and replated at a 1:15 ratio in DMEM supplemented with 10% dialyzed FCS. Media was replaced every four days. After two weeks of growth, cell foci became visible and individual clones were isolated with cloning rings. Clones which expressed the highest levels of α-Gal A were subjected to amplification en masse by step-wise growth in increasing concentrations of methotrexate (MTX), 0.02, 0.08, 1.3, 20, 40, 80, 250 and 500 $\mu$M.

6.1.4. ENZYME AND PROTEIN ASSAYS

For enzyme assay, the cells in a 100 mm culture dish were washed twice with 5 ml of phosphate buffer saline (PBS) and scraped into a 12 ml conical tube using a rubber policeman. Following centrifugation at 800×g for 10 min, the cells were resuspended in 1 ml of 25 mM $NaPO_4$ buffer, pH 6.0, and then disrupted in a Branson cup sonicator with three 15 second bursts at 70% output power. The sonicate was centrifuged at 10,000×g for 15 min at 4° C. and the supernatant was removed and assayed immediately. Alternatively, for rapid screening, cells were washed as above and 1 ml of lysis buffer (50 mM sodium phosphate buffer, pH 6.5, containing 150 mM NaCl, 1 mM EDTA, 1% NP-40, and 0.2 mM PMSF) was added to the dish. The lysed cells were incubated at 4° C. for 30 min, the lysates collected and transfered to a 1.5 ml tube, centrifuged in a microfuge, and then the supernatant was removed for assay.

The α-Gal A activities in the cell lysates and media were determined using 5 mM 4-methylumbelli-feryl-α-D-galactopyranoside (4MU-α-Gal) as previously described (Bishop, et al., 1980, In Enzyme Therapy in Genetic Diseases: 2. Desnick, R. J. (Ed.). Alan R. Liss, Inc. New York, p. 17). Briefly, a stock solution of 5 mM 4MU-α-Gal was prepared in 0.1M citrate/0.2M phosphate buffer, pH 4.6, in an ultrasonic bath. The reaction mixture, containing 10 to 50 μl of cell extract and 150μl of the stock substrate solution, was incubated at 37° C. for 10 to 30 min. The reaction was terminated with the addition of 2.3 ml of 0.1M ethylenediamine. The fluorescence was determined using a Turner model 111 Fluorometer. One unit of activity is the amount of enzyme which hydrolyzes one nmol of substrate per hour. The activities of α-mannosidase, β-galactosidase, β-hexosaminidase, β-glucuronidase and acid phosphatase were determined using the appropriate 4-methylumbelliferyl substrate. Protein concentrations were determined by the fluorescamine method (Bohlen, et al., 1973, Arch. Biochem. Biophys. 155: 213) as modified by Bishop et al. (Bishop, et al., 1978, Biochim. Biophys. Acta 524: 109).

6.2. RESULTS

6.2.1. EXPRESSION OF HUMAN α-Gal A IN COS-1 CELLS

The full-length human α-Gal A cDNA was cloned into the expression vector p91023(B) (Wong, et al., 1985, Science 228: 810) and the construct, designated p91-AGA, was introduced into COS-1 cells by electroporation. Increased levels of α-Gal A activity were detected at 24, 48 and 72 hours after transfection (FIG. 2A), indicating the functional integrity of the p91-AGA construct. At 72 hours after transfection, the α-Gal A activity increased about four-fold, while no increase in α-Gal A activity was observed in cells transfected with the p91023(B) vector containing the α-Gal A cDNA in the antisense orientation, nor in the cells that received no DNA. In addition, the β-galactosidase levels, determined as a lysosomal enzyme control, were not changed (FIG.2B).

6.2.2. TRANSFECTION AND AMPLIFICATION OF α-Gal A IN DHFR⁻ CHO CELLS

Recombinant clones stably expressing human α-Gal A were obtained by electrotransfection of the p91-AGA construct into DG44 dhfr⁻ CHO cells and amplification of the integrated vector DNA with selection in increasing MTX concentrations. Initial growth in media lacking nucleosides resulted in the identification of over 100 clones expressing α-Gal A at levels ranging from 100 to 1,800 U/mg protein (Table I). Clones with the highest α-Gal A level were grown in the presence of 0.02 to 0.08 μM MTX to amplify the integrated p91-AGA DNA. Table II shows that the intracellular α-Gal A levels in representative amplified clones increased 2 to 6 fold in 0.02 μM MTX and up to 10 fold when further amplified in 0.08 μM MTX.

TABLE I

Intracellular α-Galactosidase A Activity In
DG 44 (dhfr⁻) CHO Cells* Following
Elecrotransfection with p91-AGA

| CLONE | α-Gal A Activity (U/mg protein) |
|---|---|
| Parental DG44: | 497 |
| Transfected: | |
| 4 | 493 |
| 5 | 1,243 |
| 7 | 108 |
| 8 | 524 |
| 9 | 1,155 |
| 11 | 1,115 |
| 20 | 624 |
| 24 | 1,864 |
| 46 | 720 |
| 52 | 180 |

*Cells grown in DMEM supplemented with 10% dialyzed FCS.

TABLE II

Intracellular α-Galactosidase A Activities
In p91-AGA Transfected DG44 (dhfr⁻) CHO Cells
Following Initial Applification In Methotrexate

| CLONE | α-Gal A (U/mg) |
|---|---|
| 0.02 μM MTX: | |
| 5 | 4,990 |
| 9 | 2,900 |
| 11 | 3,170 |
| 46.1 | 1,230 |
| 46.5 | 4,570 |
| 46.12 | 4,100 |
| 0.08 μM MTX: | |
| 5.3 | 23,400 |
| 5.7 | 7,950 |
| 5.9 | 14,680 |
| 5.11 | 3,070 |
| 9.1 | 10.290 |
| 9.4 | 7,950 |
| 9.6 | 3,860 |

6.2.3. HIGH LEVEL EXPRESSION CLONES SECRETE HUMAN α-Gal A

Among the positive clones amplified in the presence of 0.08 μM MTX, clone 5.3 had the highest intracellular α-Gal A level (Table II) and therefore was chosen for further amplification. When grown in the presence of 1.3 μM MTX, the α-Gal A activity in the growth media of clone DG5.3 was determined to be 2,500 U/ml, or 25-fold greater than the level in untransfected parental DG44 cells (50 to 100 U/ml). Growth in the presence of increasing concentrations of MTX, resulted in increased intracellular and secreted α-Gal A activities (Table III). Interestingly, over 80% of the total α-Gal A produced was secreted and growth in increasing MTX concentrations continued to increase the percentage of enzyme secreted. Note that the data shown in Table III were obtained after the cells were amplified in the presence of the indicated MTX concentration and then assayed for α-Gal A activity after growth for three weeks in the absence of MTX, which accounts for their lower intracellular activities than during growth under selective pressure (Pallavicini, et al., 1990μMol. Cell Biol. 10: 401; Kaufman, R. J., 1990, Meth. Enzymol, 185: 537; Kaufman, R. J., 1990, Meth. Enzymol, 185: 487).

TABLE III

Intracellular And Secreted α-Galactosidase A Activities In p91-AGA Transfected CHO Line DG5.3 Following Step-Wise Amplification In Methotrexate. Data Were Obtained On Clones After Three Weeks Of Growth In The Absence Of Methotrexate.

| Methotrexate Concentration (μM) | CHO Cells (U/mg) | Media* (U/ml) |
| --- | --- | --- |
| Untransfected DG44: | 250 | 100 |
| Transfected p91AGA5-3: | | |
| 0.00 | 375 | 150 |
| 0.02 | 550 | 265 |
| 0.08 | 600 | 560 |
| 1.3 | 2,560 | 2,090 |
| 20 | 6,270 | 6,530 |
| 40 | 5,795 | 6,855 |
| 80 | 6,365 | 8,750 |
| 250 | 5,720 | 9,945 |
| 500 | 12,560 | 18,140 |

*$10^7$ cells and 10 ml of media for each Methotrexate concentration.

6.2.4. SPECIFIC SECRETION OF OVER-EXPRESSED LYSOSOMAL ENZYMES

To determine whether the secretion of α-Gal A was due to saturation of the receptors for lysosomal targeting, the culture media from clone DG5.3 was assayed for the presence of other lysosomal enzymes. As shown in Table IV, the activities of seven representative lysosomal enzymes were not increased or were lower than those in the media of the DG44 parental cell line, indicating that the DG5.3 secretion of α-Gal A was specific.

To determine if the secretion was specific to clone DG5.3, another clone, DG9, which was not secreting α-Gal A (i.e., activity in media was 120 U/ml), was subjected to step-wise growth in increasing MTX concentrations (i.e., from 0.02 to 20 μM MTX). After amplification in 20 μM MTX, clone DG9 had intracellular and secreted levels of α-Gal A ativity of 9,400 U/mg and 7,900 U/ml, respectively; i.e. 89% of the total α-Gal A activity produced was secreted.

TABLE IV

Lysosomal Enzyme Activities Secreted In Culture Media Of Transfected CHO Cells

| | CHO Cell Line | |
| --- | --- | --- |
| Lysosomal Enzyme | DG44* Control | 5-3$_{250}$* α-Gal A |
| α-Galactosidase A | 56 | 16,900 |
| α-Arabinosidase | 2.4 | 0.9 |
| α-Fucosidase | 341 | 358 |
| β-Galactosidase | 35.2 | 8.9 |
| β-Gaucuronidase | 90.0 | 53.7 |
| β-Hexosaminidase | 2,290 | 2,090 |

TABLE IV-continued

Lysosomal Enzyme Activities Secreted In Culture Media Of Transfected CHO Cells

| | CHO Cell Line | |
| --- | --- | --- |
| Lysosomal Enzyme | DG44* Control | 5-3$_{250}$* α-Gal A |
| α-Mannosidase | 147 | 82.8 |
| Acid Phosphatase | 30.6 | 6.1 |

*Average of Triplicate Determinations in Two Independent Experiments.

Since treatment of recombinant CHO cells with 50 mM butyrate has been shown to specifically increase transcription of the stably integrated p91023(B) vector in CHO cells (Dorner, et al., 1989, J. Biol. Chem. 264: 20602; Andrews & Adamson, 1987, Nucl. Acids Res. 15: 5461) another transfected clone, DG11, which was not amplified, was grown in the presence of 5 mM butyrate (Table V). The intracellular levels of α-Gal A activity increased from 259 U/mg to 687 U/mg. Notably, in the presence of butyrate, increased α-Gal A activity was secreted into the media (103 to 675 U/ml), suggesting that secretion occured when the gene copy number increased (or, more precisely, the steady state of α-Gal A mRNA was increased). Incubation of butyrate-induced cells with 5 mM M-6-P (to prevent recapture of the secreted enzyme by the cell surface receptor) did not result a significant increase in the amount of α-Gal A secreted.

TABLE V

Butyrate Effect On α-Gal A Secretion in CHO DG11

| | α-Gal A Activity | |
| --- | --- | --- |
| Clone | Cells (U/mg) | Media (U/ml) |
| Control | 259 | 102.6 |
| Butyrate | 687 | 675 |
| Butyrate + 5 mM M-6-P | 604 | 700 |

6.2.5. EFFECT OF SERUM CONCENTRATION ON SECRETION

To determine if the serum concentration of the growth media had an effect on the levels of recombinant α-Gal A secretion, clone DG5.3 was grown in 100 mm culture dishes at a density of $5 \times 10^6$ cells per dish, in the presence of 0% to 10% dialyzed FCS for 5 days. There was no apparent effect on α-Gal A secretion in cells grown with 2.5% to 10% serum (FIG. 3A–3B). The decreased level of secretion by DG5.3 cells cultured in 0% and 1% serum presumably reflected the poor growth of these cells.

6.2.6. PRODUCTION IN BIOREACTORS

To produce large quantities of recombinant human α-Gal A, $10^8$ cells of clone DG5.3 which had been grown in the presence of 500 μM MTX (DG5.35$_{500}$), were used to seed a hollow fiber bioreactor. As shown in FIG. 4, the level of α-Gal A produced increased to about 10,000 U/ml per day. This level remained constant for about three months. In addition, the serum concentration required by these cells in the bioreactor was step-wise decreased to 1% without seriously decreasing α-Gal A production (FIG. 4). A single 90-day run of this bioreactor resulted in >350 mg of active recombinant α-Gal A secreted into the culture media.

6.3. DISCUSSION

For human α-Gal A, post-translational modifications appear to be essential for stability and activity, as evidence by the fact that the unglycosylated enzyme expressed in *E. coli* was unstable and rapidly degraded (Hantzopoulos & Calhoun, 1987, Gene 57: 159). In addition, the α-Gal A subunit, which has four potential N-glycosylation sites, undergoes carbohydrate modification and phosphorylation for lysosomal delivery (Lemansky, et al., 1987, J. Biol. Chem. 262: 2062). Previous characterization of α-Gal A purified from plasma and tissue identified their different carbohydrate compositions, the plasma glycoform having more sialic acid residues (Bishop, et al., 1978, Biochim. Biophys. Acta 524: 109; Bishop, et al., 1980, Birth Defects 16:1; p. 17; Bishop and Desnick, 1981, J. Biol. Chem. 256:1307). Moreover, clinical trials of enzyme therapy revealed that compared to the tissue-derived form, the plasma glycoform had a prolonged retention in the circulation and was more effective in depleting the circulating accumulated substrate following intravenous administration to patents with Fabry disease (Desnick, et al., 1979, Proc. Natl. Acad. Sci. U.S.A. 76: 5326). Thus, the amplified expression of human α-Gal A in CHO cells was chosen for the expression of this recombinant enzyme whose native composition includes galactosyl and sialic acid residues (Ledonne, et al., 1983, Arch. Biochem. Biophys. 224:186).

Although this is the first human lysosomal hydrolase to be successfully overexpressed, an unexpected finding was the secretion of over 80% of the enzyme produced. This could result from several different mechanisms including (a) saturation of the mannose-6-phosphate receptor pathways; (b) a mutation that alters a critical glycosylation site; (c) failure to expose the mannose-6-phosphate moiety for receptor binding; or (d) an unusually low affinity of recombinant α-Gal A for the mannose-6-phosphate receptor (Reitman & Kornfeld, 1981, J. Biol Chem. 256: 11977; Lang, et al., 1984, J. Biol. Chem. 259: 14663; and, Gueze, et al., 1985, J. Cell. Biol. 101: 2253; for review see, Kornfeld & Mellman, 1989, Ann. Rev. Cell. Biol. 5: 483). If the secretion of α-Gal A was due to the saturation of the receptor-mediated pathway, then it would be expected that the other endogenous lysosomal enzymes also would be secreted. However, the levels of secreted CHO hydrolases were unchanged, or decreased (Table IV). To rule out a possible mutation in the α-Gal A cDNA introduced during construction and integration of the vector (Calos, et al., 1983, Proc. Natl. Acad. Sci. U.S.A. 80: 3015), the integrated vector DNA was amplified by the polymerase chain reaction. Ten subclones were completely sequenced in both orientations, and no mutations were identified. In companion studies of the purified recombinant protein (described infra), it was shown that the mannose-6-phosphate moiety was present on the enzyme and that the enzyme bound efficiently to the immobilized mannose-6-phosphate receptor. Furthermore, to prove that the secretion of this protein in the expression system utilized was not α-Gal A dependent, the cDNA encoding another lysosomal hydrolase α-N-acetylgalactosaminidase, was inserted into p91023(B) and amplified in CHO cells. Analogous to the observations with α-Gal A, cells that were high expressors of α-N-acetylgalactosaminidase (α-GalNAc), also secreted the recombinant enzyme in the medium.

The presence of functional mannose-6-phosphate moieties on the secreted enzyme implied that perhaps a different mechanism was responsible for its secretion. In fact, many other secreted proteins have been shown to contain mannose-6-phosphate. Some of these proteins include lysosomal proteins while the location of others is not clear. These proteins include, proliferin (Lee & Nathans, 1988, J. Biol. Chem. 263: 3521) secreted by proliferating mouse placental cell lines; epidermal growth factor receptor in A-431 cells (Todderud & Carpenter, 1988, J. Biol. Chem. 263: 17893); transforming growth factor β1 (Purchio, et al., 1988, J. Biol. Chem. 263: 14211); uteroferrin, an iron containing acid phosphatase secreted in large amounts by the uterine endometrium of pigs (Baumbach, et al., 1984, Proc. Natl. Acad. Sci. U.S.A. 81: 2985); and cathepsin L (MEP), a mouse lysosomal cystein protease secreted by mouse NIH 3T3 fibroblasts (Sahagian & Gottesman, 1982, J. Biol. Chem. 257: 11145). Of interest, transformation of NIH 3T3 cells with Kirstein virus results in a 25-fold increase in the synthesis of MEP causing this enzyme to be selectively secreted even though it contains functional mannose-6-phosphate moieties (Sahagian & Gottesman, 1982, J. Biol. Chem. 257: 11145). Recently, the mechanism for the selective secretion of MEP has been identified and it involves an inherent low affinity of MEP for the mannose-6-phosphate receptor (Dong, et al., 1989, J. Biol. Chem. 264: 7377).

It is also notable that the plasma-directed overexpression of yeast vacuolar carboxypeptidase Y in yeast results in over 50% of the normally glycosylated protein secreted as the precursor form (Stevens, et al., 1986, J. Cell. Biol. 102: 1551). Similar findings were observed for the yeast proteinase A gene (Rothman, et al., 1986, Proc. Natl. Acad. Sci. U.S.A. 83: 3248). Studies have suggested that the precursor glycoproteins have subcellular localization signals located within the N-terminal propeptide that are recognized by the secretion pathway, thereby precluding delivery to the lysosome-like vacuole. It is notable that the secretion of these yeast genes is gene-dosage dependent and that a similar phenomenon is observed for the expression in CHO cells of human α-Gal A. Also, it is of interest that the precursor form of the yeast enzymes was secreted. The plasma form of α-Gal A is more sialyated and secreted, and others have shown that the lysosomal enzymes in human urine are the precursor forms (Oude-Elferink, et al., 1984, Eur. J. Biochem. 139:489). However, N-terminal sequencing of recombinant α-Gal A expressed by DG44.5 revealed that the amino-terminus was identical to that of α-Gal A purified from human lung (Bishop, et al., 1986, Proc. Natl. Acad. U.S.A. 83:4859). Thus, it is possible that the high-level expression of human lysosomal hydrolases results in their secretion due to the inability to modify the precursor and/or inability of the subcellular localization machinery to accommodate the intracellular delivery of the overexpressed glycoprotein. However, this again would result in the secretion of other lysosomal enzymes. Since no other lysosomal enzymes are detected in the culture media, it is less likely that secretion of α-Gal A results from saturation of a component of the subcellular localization machinery.

Further studies, directed to determine amino acid, carbohydrate or other differences (e.g., sulfation) between the secreted and intracellular forms of recombinant α-Gal A may provide insights into the mechanism underlying the mislocalization and selective secretion of human α-Gal A. In addition, efforts to evaluate the generality of this observation should include the overexpression of other human lysosomal enzymes. The fact that large amounts of recombinant human α-Gal A are secreted by CHO cells permits the convenient production of the recombinant enzyme. Section 8, infra, describes a method for the purification of the recombinant enzyme and the characterization of its physical and kinetic properties including its receptor-mediated uptake by Fabry fibroblasts.

7. EXAMPLE: PURIFICATION, CHARACTERIZATION AND PROCESSING OF RECOMBINANT α-GalACTOSIDASE A

The subsections below describe the purification of human α-galactosidase A cloned into the amplifiable eukaryotic expression vector, p91023(B), and overexpressed in Chinese hamster ovary (CHO) cells. The recombinant enzyme protein, was selectively secreted into the culture media and over 200 mg was purified to homogeneity by a Fast Protein Liquid Chromatographic procedure including affinity chromatography on α-galactosylamine-Sepharose. The purified secreted enzyme was a homodimeric glycoprotein with native and subunit molecular weights of about 110 and 57 kDa, respectively. The recombinant enzyme had a pI of 3.7, a pH optimum of 4.6, and a km of 1.9 mM toward 4-methylumbelliferyl-α-D-galactopyranoside. It rapidly hydrolyzed pyrene-dodecanoyl-sphingosyl-trihexoside, a fluorescently labeled analogue of the natural glycosphingolipid substrate, which was targeted with apolipoprotein E to the lysosomes of the enzyme-producing CHO cells. Pulse-chase studies indicated that the recombinant enzyme assumed its disulfide-defined secondary structure in <3 min, W,s in the Golgi by 5 min where it became Endo H resistant and was secreted into the media by 45–60 min. Both the intracellular and secreted forms were phosphorylated. The secreted enzyme subunit was slightly larger than the intracellular subunit. However, following endoglycosidase treatment, both subunits co-migrated on SDS-PAGE, indicating differences in the oligosaccharide moieties of the two forms. Treatment of the radiolabeled secreted enzyme with various endoglycosidases revealed the presence of three N-linked oligosaccharide chains, two high-mannose types (Endo H sensitive) and one complex type, the latter being Endo H and F resistant. Analyses of the Endo H-released oligosaccharides revealed that one had two phosphate residues which specifically bound to immobilized mannose-6-phosphate receptors while the other was a hybrid structure containing sialic acid. These physical and kinetic properties and the presence of complex-type oligosaccharide chains on the recombinant secreted enzyme were similar to those of the native enzyme purified from human plasma. The secreted form of α-Gal A was taken up by cultured Fabry fibroblasts by a saturable process that was blocked in the presence of 2 mM mannose-6-phosphate indicating that binding and internalization were mediated by the mannose-6-phosphate receptor. The binding profiles of the recombinant secreted enzyme and the α-Gal A secreted by $NH_4Cl$-treated human fibroblasts to the immobilized receptor were identical. The production of large amounts of soluble, active recombinant α-Gal A in accordance with the invention, which is similar in structure to the native enzyme isolated from plasma, will permit further comparison to the native enzyme forms and the clinical evaluation of enzyme replacement in Fabry disease.

7.1. MATERIALS AND METHODS

7.1.1. MATERIALS

Endo-β-N-acetylglucosaminidase H (Endo H), endo-β-N-acetylglucosaminidase D (Endo D), endoglycosidase F (Endo F) and peptide:N-glycosidase F (PNGase F) were obtained from Boeringer Mannheim, Indianapolis, Ind. [$^{35}$S]-methionine (>1,000 Ci/mmol), D-[2,6-$^3$H]-mannose (60 Ci/mmol), $^{32}$P-Phosphorus (10 mCi/ml) and Amplify were obtained from Amersham, Arlington Heights, Ill. Pansorbin was obtained from Calbiochem, San Diego, Calif. 4-MU glycosides were obtained from Genzyme, Cambridge, Mass. Freund's adjuvants, sphingomyelin (from brain) and phenylmethylsulfonyl fluoride (PMSF) were obtained from Sigma, St. Louis, Mo. QAE Sephadex, Sephadex G-25, octyl Sepharose and Superose 6 were obtained from Pharmacia-LKB, Piscataway, N.J. The TLC silica plates (cat. 5626) were purchased from EM Science, Gibbstown, N.J. The COS-1 cell line was obtained from the ATCC. All tissue culture reagents were obtained from Gibco, Grand Island, N.Y. Sinti Verse I scintillation cocktail was obtained from Fisher, Pittsburgh, Pa. The immobilized mannose-6-phosphate receptor was obtained from Dr. Stuart Kornfeld, Washington University, St. Louis, Mo. The pyrene-dodecanoyl-sphingosyl-trihexoside (P-$C_{12}$STH) was obtained from Dr. Shimon Gatt, Hebrew University, Israel. Apolipoprotein E was obtained from BTG Inc., Ness-Ziona, Israel.

7.1.2. CELL CULTURE

Cells were maintained at 37° C. in 5% $CO_2$ in Dulbecco's Modification of Eagle's Medium (DMEM) with 10% fetal calf serum (FCS) and antibiotics. The DG44 line was cultured in DMEM supplemented with HT (hypoxanthine, thymidine, Sigma) while the recombinant CHO line DG5.3 received DMEM supplemented with 10% dialyzed FCS. (Kaufman, et al., 1988, J. Biol. Chem. 263: 6352).

7.1.3. PURIFICATION OF RECOMBINANT α-Gal A

Recombinant CHO culture media was collected (20 L) and concentrated to 500 ml using a Pellicon cassette tangential-flow concentrator, with a molecular weight cutoff of 10,000 daltons (Millipore, Mass.). The pH of the concentrate was adjusted to 4.7 to 5.0 with 10N HCl and subsequently clarified by centrifugation at 10,000×g in an RC-5 refrigerated centrifuge for 10 min.

All chromatographic steps were automated on an FPLC apparatus (Pharmacia) and were performed at room temperature. Approximately 100 ml of the media concentrate (~20 mg of α-Gal A enzyme protein) was applied to an α-Gal A affinity column (α-GalNH$_2$-Sepharose; 2.5×8 cm) (Bishop & Desnick, 1981, J. Biol. Chem. 256: 1307) pre-equilibrated with buffer A (0.1M citrate-phosphate, pH 4.7, 0.15M NaCl). The column was washed with buffer A until the protein concentration in the eluate returned to the pre-application level (~200 ml) and was eluted with 150 ml of buffer B (0.1M citrate-phosphate, pH 6.0, 0.15M NaCl, 70.4 mM galactose). The eluate was collected, concentrated to about 20 ml using an ultrafiltration cell, molecular weight cutoff 30,000 daltons, under positive nitrogen pressure (Amicon). The concentrate was mixed with an equal volume of buffer C (25 mM Bis-Tris, pH 6.0, 3M ($N_4$)$_2SO_4$), centrifuged at 10,000×g and the pellet which contained up to 40% of the activity, was redissolved in buffer A and mixed with an equal volume of buffer C and centrifuged as above. The combined supernatants were applied to a column of Octyl-Sepharose (1.5×18 cm) pre-equilibrated with buffer D (25 mM Bis-Tris, pH 6.0, 1.5M (NH$_4$)$_2SO_4$). The column was washed as above until the eluting protein concentration returned to pre-application levels (~100 ml) and the column was eluted with buffer E (5 mM sodium-phosphate, pH 6.0, 50% ethylene glycol). The product from three Octyl-Sepharose elutions, totalling approximately 75 ml, was concentrated as above to about 2 ml using an Amicon concentrator. The concentrate was finally applied to a column of Superose 6 (20–40 μm, Pharmacia, 1.6 ×100 cm)

equilibrated in buffer F (25 mM sodium phosphate, pH 6.5, 0.1M NaCl). The α-Gal A peak was collected, ~20 ml, concentrated as above and stored in buffer F at 4° C.

7.1.4. ENZYME AND PROTEIN ASSAYS

α-Gal A was assayed using 4-methylumbelliferyl-α-D-galactopyranoside (4-MU-α-Gal) as previously described (Bishop, et al., 1980, In Enzyme Therapy in Genetic Diseases: 2. Desnick, R. J. (Ed.). Alan R. Liss, Inc. New York, p. 17). Briefly, a stock solution of 5 mM 4-MU was prepared in 0.1M citrate-phosphate buffer, pH 4.6 solubilized in an ultrasonic bath. The reaction mixtures containing 10–50 μl of enzyme preparation or cell extracts and 150 μl substrate, were incubated at 37° C. for 10–30 min. The reactions were terminated with the addition of 2.33 ml of 0.1M ethylenediamine. One unit of activity is that amount of enzyme which hydrolyzes 1 nmol of substrate/hour.

Endo H, Endo D, Endo F and PNGase F digestions were performed as described (Tarentino, et al., 1989, Meth. Cell. Biol. 32: 111). Samples were diluted to 0.2–0.5% SDS before digestion. All reaction volumes were 50 μl. A drop of toluene was added to each reaction tube to prevent bacterial growth. Briefly, Endo H digestions (5 mU/reaction) were performed at 37° C. overnight in 5 mM sodium citrate, pH 5.5 and 0.2 mM PMSF. Endo D digestions (10 mU/reaction) were performed at 37° C. overnight in 0.2M citrate phosphate buffer, pH 6.0 a,d 0.2 mM PMSF. Endo F digestions (50 mU/reaction) were performed overnight at 30° C. in 0.17 M sodium acetate, pH 6.0, 1.6% NP-40 and 0.2 mM PMSF. PNGase F digestions (100 mU/reaction) were carried out overnight at 30° C. in 0.17M potassium phosphate, pH 8.6, 1.6% NP-40, 0.2 mM PMSF.

Protein concentration was determined by the fluorescamine method (Bohlen, et al., 1973, Arch. Biochem. Biophys. 155: 213) as modified by Bishop et al. (Bishop et al., 1978, Biochim. Biophys. Acta 524: 109).

7.1.5. IN VIVO NATURAL SUBSTRATE ASSAY

For this assay, 30 nmoles of P-$C_2$STH and 70 nmoles of-sphingomyelin were mixed in a chloroform:methanol solution (1:1), evaporated under nitrogen and dried in a Speed-Vac (Savant). The pellet was resuspended in 2 ml of saline, sonicated using a Heat Systems Ultrasonics, Inc., Microson sonicator for 3–5 min at 40% output power and allowed to stand at room temperature for 1 hour. Apolipoprotein E (80 μg) was added and the mixture was incubated for an additional 15 min at room temperature. The liposomes were added to the culture media of recombinant CHO cells and incubated at 37° C. in a $CO_2$ incubator for 1 to 4 hours. Cells were removed from the culture dishes by trypsinization, washed once in DMEM supplemented with 10% fetal calf serum and twice with saline. The cell pellet was resuspended in chloroform-methanol and heated to 60° C. for 10 min and centrifuged at 600×g for 10 min. The supernatant was dried under nitrogen and the pellet resuspended in 100 μl of chloroform:methanol. Samples were spotted on a silica gel thin layer chromatography plate and chromatographed in chloroform:methanol:water (90:10:1) for 45 min followed by chromatography in chloroform:methanol:water (75:25:4) for 30 min. Products were visualized under UV light (330 nm), excised from the plate by scraping, resuspended in chloroform:methanol, and their fluorescence quantitated in a Farrand spectrofluorometer (343 nm excitation, 378 nm emission).

7.1.6. POLYCLONAL ANTIBODIES

A New Zealand white rabbit (2 kg) was injected with 150 μg of purified splenic α-Gal A in Freund's complete adjuvant prepared as follows: 150 μg of α-Gal A was added to 0.5 ml of PBS in a glass syringe. Using a stainless steel 21 gauge needle, the PBS/α-Gal A solution was mixed with 0.5 ml of Freund's complete adjuvant in a second glass syringe, until a homogenous emulsion was obtained. The emulsion was injected into 8 different subcutaneous sites (back) and 1 intramuscular site (thigh). Two months following the initial injection, the rabbit was boosted with 50 μg of α-Gal A in Freund's incomplete adjuvant as above. Serum was collected from an ear vein at days 8 and 12 following the boost. The titer was checked using a standard ELISA assay (Johnstone & Thorpe, 1982, Iummunochemistry in Practice. Balckwell Scientific Publications, Oxford). Subsequent boosts were given approximately every two months followed by a bleeding 10 days later. A typical bleed yielded 30–40 ml of blood.

7.1.7. SDS-PAGE AND AUTORADIOGRAPHY

Polyacrylamide gel electrophoresis was carried out under reducing conditions (where appropriate) as described by Laemmli in a 1.5 mm thick slab containing 10% acrylamide (Laemmli, U.K., 1970, Nature 227: 680). The gel was fixed in 10% acetic acid and 20% methanol for 30 min and then soaked in Amplify for 30 min with agitation. Gels were vacuum dried for 90 min (Hoffer) and exposed to Kodak X Omat AR for 4 to 72 hours.

7.1.8. ISOELECTRIC POINT AND pH OPTIMUM DETERMINATION

The isoelectric point was determined using QAE sephadex essentially as described by Yang and Langer (Yang & Langer, 1987, Biotechniques 5: 1138). The pH optimum was determined in 25 mM sodium phosphate buffer at 37° C.

7.1.9. MANNOSE-6-PHOSPHATE RECEPTOR AFFINITY CHROMATOGRAPHY AND QAE SEPHADEX CHROMATOGRAPHY

The 215 kDa mannose-6-phosphate receptor (M-6-P receptor) coupled to Affigel-10 was at a concentration of 0.4 mg/ml of packed gel. Samples, in binding buffer (50 mM imidazole, pH 7.0, 150 mM NaCl, 0.05% Triton X-100, 5 mM sodium-β-glycerolphosphate, 0.02% sodium azide), were applied to a 1.5×0.8 cm column at a flow rate of 0.3 ml/minute. Following sample application (5 ml), the column was washed with 5 ml of binding buffer and eluted with a nonlinear gradient of mannose-6-phosphate in binding buffer (0–5 mM). This exponential gradient (Dong, et al., 1990, J. Biol. Chem. 265: 4210) was formed by an apparatus consisting of two chambers of 2.5 cm diameter and 1 cm diameter. Fractions were collected (0.5 ml) and 10 μl aliquots assayed for α-Gal A activity using 4-MU-α-Gal, and for radioactivity using 10 ml of Sinti Verse I scintillation coctail.

QAE Sephadex chromatography in a 3×0.8 cm column was performed as described (Varki & Kornfeld, 1983, J. Biol. Chem. 258: 2808; Varki & Kornfeld, 1980, J. Biol. Chem. 255: 10847). Briefly, following digestion with Endo H, the released oligosaccharides (labeled with [$^3$H]-mannose) were isolated and desalted on an 18×0.8 cm column of Sephadex G-25. Samples were applied to the column of QAE Sephadex and eluted with successive 5 ml aliquots of 2 mM Tris, pH 8.0 containing 0, 20, 40, 80, 100, 120, 140, 160, 200, 400 and 1,000 mM NaCl. Oligosaccharides eluted according to the number of their negative charges; 0 charge at 0 mM NaCl, 1 at 20 mM NaCl, 2 at 70 mM NaCl, 3 at 100 mM NaCl and 4 at 140 mM NaCl.

7.1.10. LABELING OF CELLS WITH [$^{35}$S]-METHIONINE, [$^{3}$H]-MANNOSE AND [$^{32}$p]-PHOSPHOROUS

Confluent cultures in 100 mm dishes were washed once with 5 ml of methionine-free DMEM. A fresh aliquot of this medium (5 ml) was placed in each dish and cultures were incubated in a 37° C. incubator for 30 min. The media was removed from the dishes and a fresh aliquot of methionine-free DMEM (1 ml), supplemented with 10% dialyzed FCS and 50–100 µCi of [$^{35}$S]-methionine was added. Cells were incubated at 37° C. for 3 to 5 min, the radioactive media was removed and cells washed twice with DMEM plus FCS. Cells were chased for the indicated times in 5 ml of DMEM plus FCS containing 2 mM methionine. For overnight labeling, cultures received 5 ml of methionine-free DMEM supplemented with dialyzed FCS, glutamine, antibiotics, 10 mM NH$_4$Cl and 200 µCi [$^{35}$S]-methionine.

For [$^{3}$H]-mannose labeling, cultures were grown as above in supplemented DMEM. Cells were washed with 5 ml of low-glucose DMEM and a fresh aliquot of media was added. [$^{3}$H]-mannose (250 µCi; dried under nitrogen and resuspended in DMEM), was added and cells were incubated in a 37° C. incubator for 24 hours.

For $^{32}$P labeling, cultures were switched to phosphate-free DMEM supplemented with 10% dialyzed FCS. Following addition of [$^{32}$P]-orthophosphate (1 mCi) cultures were incubated in a 37° C., CO$_2$ incubator for 24 hours.

7.1.11. CELL LYSIS AND IMMUNOPRECIPITATION

Cells grown in 100 mm culture dishes were washed twice with 5 ml of phosphate buffered saline (PBS) and scraped into 12 ml conical tubes using a rubber policeman and 10 ml of PBS. Following centrifugation at 2,500 rpm for 10 min cells were resuspended in 1 ml of 25 mM NaPO$_4$, pH 6.0 and received three 15-second bursts in a Branson cup sonicator. Cell debris was removed by centrifugation (10,000×g for 15 min at 4° C.). Alternatively, cells were washed as above and 1 ml of lysis buffer (50 mM sodium phosphate, pH 6.5, 150 mM NaCl, 1 mM EDTA, 1% NP-40, 0.2 mM PMSF) was added to the dish. The culture dish was incubated at 4° C. for 30 min and cells were transferred to a 1.5 ml microcentrifuge tube. Cell debris was removed as above.

Immunoprecipitation was carried out as described (Sambrook, et al., 1989, Molecular Cloning: A Laboratory Manual Cold Spring Harbor Laboratory Press pp. 18.42–18.46). Briefly, 0.5 ml of cell lysate or culture media was placed in a 1.5 ml microcentrifuge tube and 50 µl of preimmune rabbit serum was added. The mixture was incubated at 4° C. for 1 hour with gentle agitation. Fifty µl of Pansorbin was added and incubation was continued for 30 min. The mixture was clarified by centrifigation at 10,000×g for 5 min, 100 µl of anti-α-Gal A polyclonal antibody was added and incubation was continued for 1 hour at 4, C with gentle rocking. Pansorbin (100 µl) was added and incubation continued for 30 min as above. The tertiary S. aureus cells-antibody-antigen complex was collected by centrifugation as above. The supernatant was discarded and the pellet washed successively in NET buffer (50 mM sodium phosphate, pH 6.5, 150 mM NaCl, 1 mM EDTA, 1% NP-40, 0.25% gelatin) supplemented with 0.5M NaCl, in NET buffer with 0.1% SDS and in TN buffer (10 mM Tris, pH 7.5, 0.1% NP-40). The immunoprecipitated protein was denatured by heating at 100° C. for 5 min in the presence of 2% SDS, 100 mM DTT (DTT was not used for experiments involving secondary structure conformations). S. aureus cells were removed by centrifugation at 10,000×g for 5 min at room temperature.

7.2. RESULTS

7.2.1. PURIFICATION

Recombinant α-Gal A produced in the cell bioreactor was purified from the crude media by affinty chromatography on α-GalNH$_2$-C$_{12}$-Sepharose (Bishop & Desnick, 1981, J. Biol. Chem. 256: 1307) followed by hydrophobic chromatography on Octyl Sepharose and gel filtration on a 100 cm Superose 6 column as described above. Table VI shows a typical purification of a 20 mg lot of recombinant α-Gal A and the specific activities of the enzyme at each stage of purification. The recombinant enzyme was essentially homogeneous, following the gel filtration step, and was >98% pure as judged by SDS-PAGE (FIG. 5). A minor contaminant of bovine serum albumin was removed by an additional gel filtration step on a column of Blue-Sepharose (Travis, et al., 1976, Biochem. J. 157: 301) resulting in an enzyme preparation which was greater than 99% pure as judged by loading 20 µg of α-Gal A on SDS-PAGE.

TABLE VI

FPLC Purification Of Recombinant α-GAL A
A Typical Purification Run Starting With 20 MG Of α-GAL A

| Step | U × 10$^3$ | U × 10$^3$ | Fold Purification | Yield % |
| --- | --- | --- | --- | --- |
| Media | 39,750 | 5 | 1 | 100 |
| α-GalNH$_2$-Sepharose | 36,500 | 680 | 136 | 91 |
| Octyl Sepharose | 31,750 | 3,400 | 680 | 79 |
| Superose 6 | 30,800 | 4,150 | 830 | 78 |

That the purification of recombinant α-Gal A would be facilitated by growth of the CHO cells in serum-free media was demonstrated by metabolic labelling of total cellular and secreted protein. In contrast to the result seen in FIG. 5, radiolabeled α-Gal A was essentially the only protein seen in the media of the high-expressor line, DG5.3 (FIG. 6).

7.2.2. PHYSICOKINETIC PROPERTIES

Recombinant α-Gal A was found to have a subunit molecular weight of ~57 Kd based on SDS-PAGE (FIG. 5). The Km towards the artificial substrate 4-MU-α-D-galactopyranoside was 1.9 mM (FIG. 7A) and the pH optimum and isoelectric point were 4.6 and 3.7 respectively (FIG. 7B and 7C).

In order to determine whether the recombinant enzyme recognized and hydrolyzed its natural substrate, liposomes containing the fluorescently-labeled α-Gal A substrate P-C$_{12}$STH and apolipoprotein E (for lysosomal targeting) were incubated with CHO cells over-expressing α-Gal A (clone DG5.3). As shown in FIG. 8A–8B, recombinant lysosomal α-Gal A rapidly hydrolyzed the substrate to P-C$_{12}$SDH (the dihexoside). The rapid hydrolysis of P-C$_{12}$STH indicates that recombinant α-Gal A can recognize this natural substrate analog and very efficiently hydrolyze it. Also, since this substrate is targeted to the lysosome, cell associated recombinant α-Gal A must be correctly targeted to this location. These results indicate that recombinant α-Gal A produced and secreted by CHO cells is essentially identical to the enzyme purified from human plasma (Table VII).

TABLE VII

Property Comparison Of Recombinant α-GALACTOSIDASE A Enzyme Purified From Human Tissue

| Property | α-Gal A | | |
| --- | --- | --- | --- |
| | Spleen | Plasma | Recombinant |
| MW-Subunit, (KDa) | 53 | 57 | 57 |
| pH Optimum | 4.5 | 4.6 | 4.6 |
| Isoelectric Point, PI | 4.3 | 3.7 | 3.7 |
| Km (4-MU-α-D-Gal), mM | 2.5 | 1.9 | 1.9 |
| Phosphorylation (M-6-P) | + | ? | + |
| Natural Substrate Hydrolysis (GL-3) | + | + | + |

7.2.3. PROCESSING AND RATE OF SECRETION OF RECOMBINANT α-Gal A

Nascent polypeptides, transversing the endoplasmic reticulum assume secondary structure conformations cotranslationally or soon after their synthesis is completed (Gething, et al., 1989, Meth. Cell. Biol. 32: 185). α-Gal A was labeled with [$^{35}$S]-methionine for three min and then chased with cold methionine for the indicated times. Immunoprecipitated α-Gal A was visualized on SDS-PAGE. The samples were prepared without DTT in order to maintain disulfide bridges that might have formed during the chase, indicative of a secondary structure conformation. A control (+DTT) was prepared by boiling an aliquot of the 60 minute sample in the presence of DTT to destroy disulfide bonds and the secondary structure. At 0 min of chase (after 3 min of labeling) there was already a change in the mobility of this enzyme indicating that conformational changes occur cotranslationally or soon after completion of synthesis (FIG. 9).

Arrival of the new polypeptide to the Golgi network was detected by the acquisition of Endo H resistant oligosaccharides (Gething, et al., 1989, Meth. Cell. Biol. 32: 185). Radiolabeled α-Gal A (3 minute pulse) was chased with nonradioactive methionine and immunoprecipitated as above. The immunoprecipitates were then treated with Endo H and visualized on SDS-PAGE. Between 2 and 7 min of chase, the first Endo H-resistant form of α-Gal A could be detected, indicative of arrival of the recombinant enzyme at the Golgi, about 5 to 10 min following its synthesis (FIG. 10). The majority of the Endo H sensitive form was rendered resistant by 60 min of chase.

Figure 11:
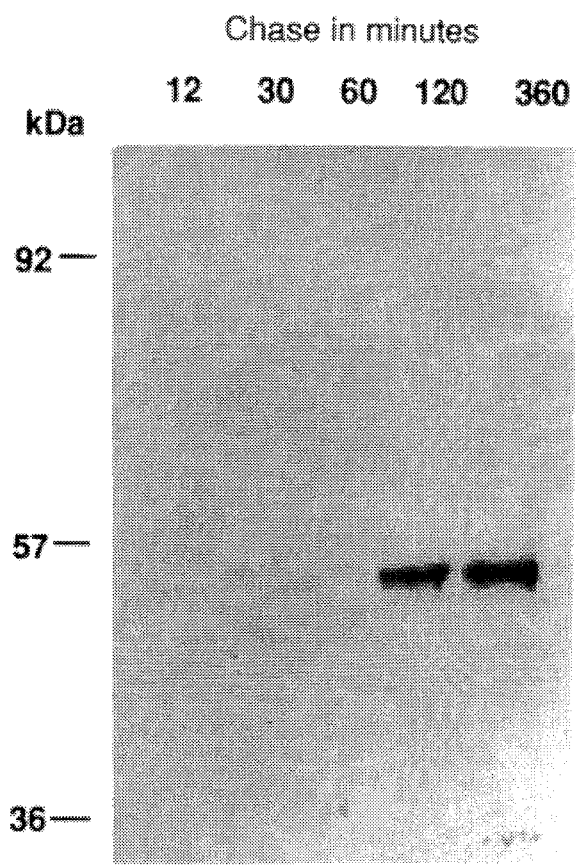

This enzyme transverses the Golgi network and is secreted at 45 to 60 min of chase (FIG. 11). Analysis of total media, from [$^{35}$S]-methionine labeled cells, revealed that >95% of the secreted protein by the recombinant CHO cells was α-Gal A (FIG. 12).

7.2.4. ANALYSIS OF CARBOHYDRATE MOIETIES ON RECOMBINANT α-Gal A

There are four N-glycosylation consensus sequences (Asn-X-Ser/Thr) in the α-Gal subunit predicted by the cDNA sequence. The fourth site is probably not utilized since it contains a proline residue in the X position. Recombinant α-Gal A was digested with Endo H, Endo F, Endo D and PNGase F. Digestion with PNGase F caused an ™7 kDa shift in mobility on SDS-PAGE of half of the α-Gal A (FIG. 13). This change in molecular weight can be attributed to the removal of 3N-linked carbohydrate moieties. Digestion of the recombinant enzyme with a cocktail of Endo H, Endo F and PNGase F did not result in any further decrease in molecular weight, indicating that all of the enzyme contains three N-linked carbohydrate moieties.

Endo D, a glycosidase with a strict specificity for the lower Manα1-3 branch of the high-mannose core pentasaccharide (Tarentino, et al., 1989, Meth. Cell. Biol. 32: 111), did not have an effect on the mobility of α-Gal A, indicating that the recombinant enzyme does not contain this type of oligosaccharide (FIG. 13). Endo H and Endo F together resulted in a 4 kDa shift indicating that two out of the three oligosaccharides on this enzyme are of the high-mannose type (Varki & Kornfeld, 1980, J. Biol. Chem. 225: 10847).

Interestingly, intracellular α-Gal A was completely sensitive to PNGase F while half of the secreted enzyme was partially resistant to PNGase F (FIG. 14). Since this resistance was eliminated by co-treatment with Endo H and Endo F (FIG. 13), further studies are necessary with Endo H and Endo F separately to determine the molecular nature of either the selective inhibition of PNGase F or the resistance of a proportion of the recombinant secreted enzyme to PNGase F digestion.

Having determined that the recombinant enzyme contains three oligosaccharides, two of which are of the high-mannose type, the effect of inhibition of glycosylation was investigated (Furhmann, et al., 1985, Biochim. Biophys. Acta 825: 95). Processing and secretion of recombinant α-Gal A is not affected by selective inhibition of oligosaccharide processing. In the presence of deoxynojirimycin (an inhibitor of glucosidase I and II), deoxymannojirimycin (an inhibitor of mannosidase I), and swainsonine (an inhibitor of mannosidase II) α-Gal A secretion rate remains the same as the controls (FIG. 15). However, tunicamycin (an inhibitor of oligosaccharide addition) inhibits secretion of α-Gal A by as much as 80% (FIG. 15). The secreted enzyme from tunicamycin-treated cultures could bind to a Con A Sepharose column indicating that this enzyme is partially glycosylated, probably due to incomplete inhibition of glycosylation by tunicamycin. These results indicate that oligosaccharide addition but not the processing events tested is necessary for maturation and secretion of the recombinant enzyme.

7.2.5. PHOSPORYLATION

Since the recombinant α-Gal A contained high-mannose moieties, the recombinant enzyme could contain M-6-P and be competent for receptor mediated uptake. Cells from clone DG5.3 were metabolically labeled with [$^{32}$P]-orthophosphate for 12 hours and then the cell extracts and media immunoprecipitated and visualized on SDS-PAGE. As shown in FIG. 16, both cell-associated and secreted α-Gal A were phosphorylated, presumably at their carbohydrate moieties as suggested by the in vitro experiments described above.

7.2.6. ANALYSIS OF ENDO H SENSITIVE OLIGOSACCHARIDES

Figure 17A:
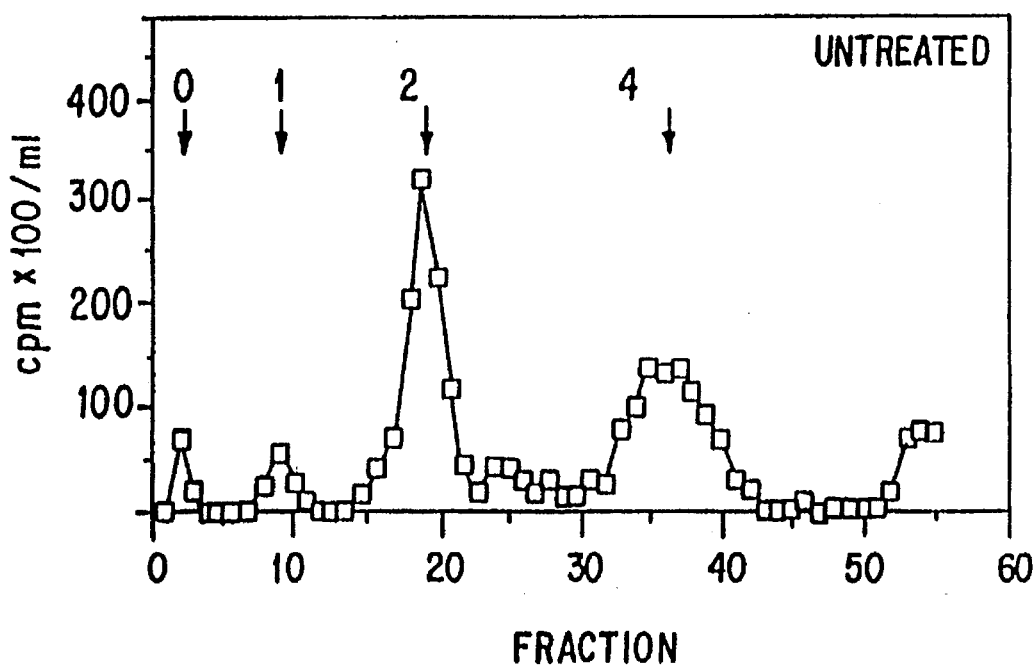
Figure 17B:
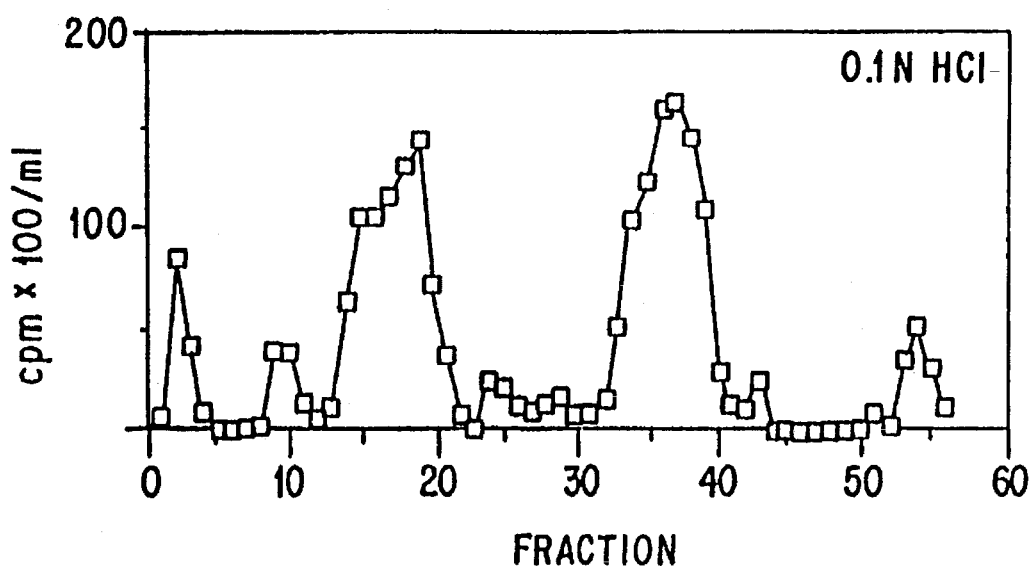
Figure 17C:
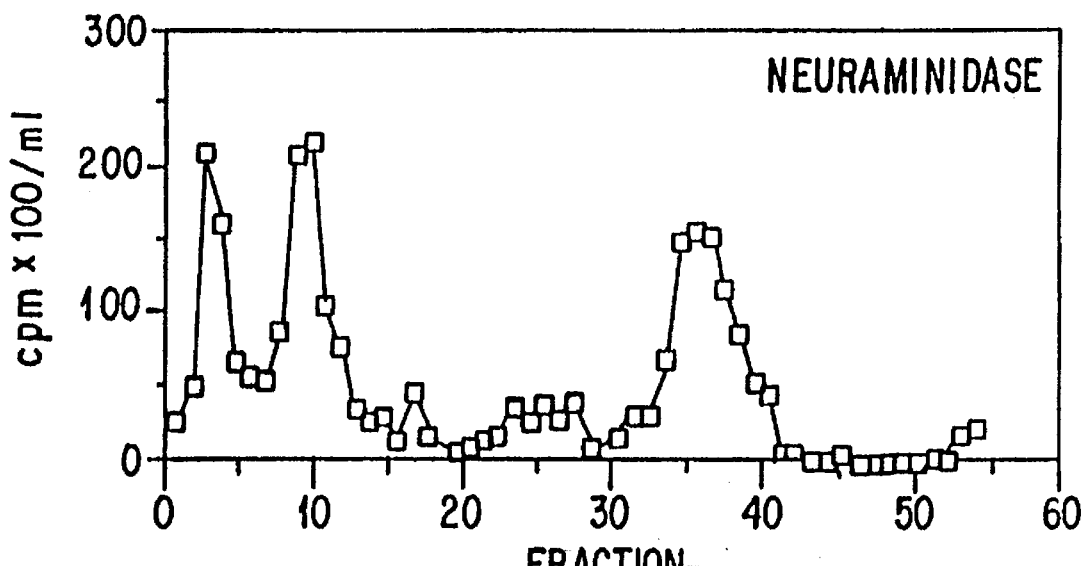
Figure 17D:
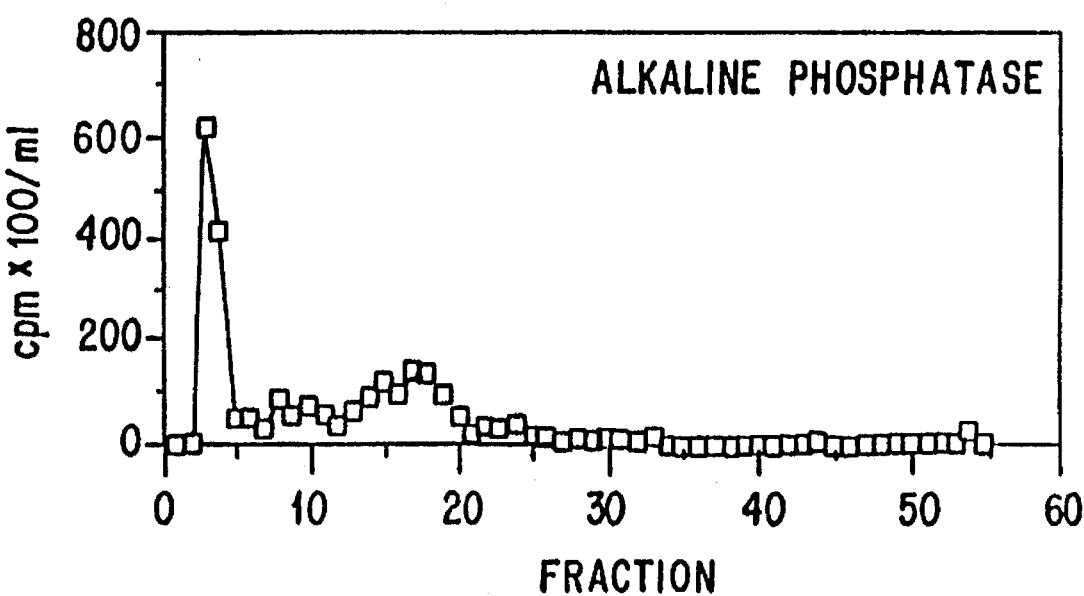

The high-mannose oligosaccharides were removed by treating immunoprecipitated [$^3$H]-mannose labeled α-Gal A with Endo H. These oligosaccharides were analysed by chromatography on QAE Sephadex (Varki & Kornfeld, 1983, J. Biol. Chem. 258: 2808; and, Varki & Kornfeld, 1980, J. Biol. Chem. 255: 10847). Two major forms of these oligosaccharides were detected, a form with 2 negative charges and one with 4 negative charges (FIG. 17A). The negative charge can be contributed by a phosphodiester moiety (−1), a phosphomonoester moiety (−2) or sialic acid (−1). Treatment of these sugars with dilute HCl did not shift the profile of any of the peaks indicating that there are no phosphodiester groups on these sugars (FIG. 17B) (Varki & Kornfeld, 1983, J. Biol. Chem. 258: 2808). Treatment with neuraminidase causes a shift of the −2 peak resulting in two new peaks at 0 and −1 negative charges (FIG. 17C). Therefore, the charge of the −2 peak is contributed by sialic acid, most likely two moieties. The resulting −1 peak following neuraminidase treatment is probably a partial digestion of the −2 peak by the enzyme. Treatment of these oligosaccharides with alkaline phosphatase caused a shift of the −4 peak to 0 negative charge (FIG. 17D). There was no effect on the −2 peak, indicating that the charge of the −4 peak is contributed by two phosphomonoester bonds while the −2 peak does not contain any such bonds. Thus, it is evident from these results that Endo H releases two types of high-mannose oligosaccharides from recombinant α-Gal A, one containing sialic acid (possibly a hybrid oligosaccharide) and the other containing 2 phosphomonoester bonds (presumably as mannose-6-phosphate).

To further confirm these findings peaks −2 and −4 were chromatographed on an immobilized mannose-6-phosphate receptor column (FIG. 18). Although peak −4 interacted weakly with the receptor, it could be bound to the column and required the addition of mannose-6-phosphate for elution. A very weak interaction was observed between the receptor column and the −2 peak, suggesting that a portion of these hybrid oligosaccharides may contain M-6-P.

The weak interaction of the high-mannose oligosaccharides with the M-6-P receptor could be explained by the absence of the protein core (Varki & Kornfeld, 1983, J. Biol. Chem. 258: 2808). DG5.3 cells were labeled with [$^{35}$S]-methionine and the secretions chromatographed on a column of immobilized mannose-6-phosphate receptor. Notably, the recombinant enzyme bound strongly to the column was eluted specifically by the addition of 5 mM M-6-P (FIG. 19).

7.2.7. INTERACTION OF α-Gal A WITH THE MANNOSE-6-PHOSPHATE RECEPTOR

Since recombinant α-Gal A has been shown to contain mannose-6-phosphate moieties, it was important to establish whether this was also true for normal human α-Gal A. CHO proteins were labeled with [$^{35}$S]methionine in the presence of NH$_4$Cl, to cause quantitative secretion of newly synthesized lysosomal enzymes (Dean, et al., 1984, Biochem. J. 217: 27). The media was collected and chromatographed on a column of immobilized mannose-6-phosphate receptor. The column was eluted with a gradient of mannose-6-phosphate as described above. This elution protocol can separate lysosomal enzymes into low and high affinity receptor-binding ligands (Dong & Sahagian, 1990, J. Biol. Chem. 265: 4210).

The recombinant enzyme co-eluted with the bulk of the lysosomal enzymes at an M-6-P concentration indicative of high affinity forms (FIG. 20A). The same experiment was performed with secretions of MS914 (normal diploid human fibroblasts) cells (FIG. 20B) and 293 cells (human adenovirus transformed embryonic kidney cells) (FIG. 20C). When the same M-6-P gradient was applied, human α-Gal A also co-eluted with the bulk of the lysosomal enzymes, demonstrating that the recombinant enzyme exhibits affinity to the M-6-P receptor similar to that of the normal human enzyme.

7.2.8. RECEPTOR MEDIATED UPTAKE OF RECOMBINANT α-Gal A IN FABRY FIBROBLASTS

Fabry fibroblasts were incubated with varying amounts of the recombinant enzyme for 6 hours (FIG. 21). The enzyme uptake was saturatable and was specifically inhibited by the addition of 2 mM M-6-P in the uptake media, indicating that the uptake was via the cell surface M-6-P receptor.

8. EXAMPLE: α-Gal A-PROTEIN A FUSION EXPRESSED IN MAMMALIAN CELLS

The subsections below describe a fusion construct of the human α-Galactosidase A cDNA and the staphylococcal protein A IgG binding domain E expressed in COS-1 cells and purified to apparent homogeneity by IgG affinity chromatography. The fusion construct was engineered using PCR techniques to insert the 16 nucleotide collagenase cleavage recognition sequence between the α-Gal A and the protein A domain E sequence. In addition, the termination codon was deleted from the α-Gal cDNA and inserted at the terminus of the domain E sequence. Transient expression of the fusion construct in COS-1 cells resulted in a 6 to 7-fold increase over endogenous levels of α-Gal A activity and significant secretion into the media (4,000 units; nmoles/hour). The fusion protein from the culture media was purified to homogeneity on IgG sepharose chromatography. After collagenase treatment, the liberated α-Gal A was separated from the protein A peptide by IgG chromatography. By this method over 85% of secreted α-Gal A fusion protein was purified as the active, glycosylated homodimeric protein. This method should be useful for the expression and rapid purification of normal and mutant proteins. In addition, this construct has been inserted into the CHO DG44 cells so that large amounts of the secreted recombinant enzyme can be produced and rapidly and efficiently purified.

8.1. MATERIALS AND METHODS

8.1.1. MATERIALS

Restriction endonucleases, Taq polymerase, T4 ligase and pGem plasmids were obtained from Promega (Madison, Wis.). Vector pRIT5 and IgG-Sepharose were purchased from Pharmacia (Piscataway, N.J.). Sequenase sequencing kits were from United States Biochemical Corp. (Cleveland, Ohio). Collagenase was obtained from Sigma (St. Louis, Mo.). Oligonucleotides were synthesized using an Applied Biosystems DNA synthesizer model 380B.

8.1.2. CELL CULTURE AND TRANSFECTIONS

COS-1 cells were obtained from the ATCC (Rockville, Md.). The cells were cultured by standard techniques in Dulbecco's Modified Eagle's Medium (DMEM) with 10% fetal calf serum and antibiotics.

Exponentially growing COS-1 cells (5×10$^6$ cells/T75 flask) were detached from the plastic by trypsinization, collected by centrifugation at 3,000×g, and then washed once in ice-cold electroporation buffer (phosphate buffered sucrose: 272 mM sucrose, 7 mM sodium phosphate, pH 7.4, containing 1 mM MgCl$_2$). Following centrifugation at 3,000×g, the cells were resuspended in 0.8 ml of electroporation buffer and placed in an electroporation cuvette with a 0.4 cm gap. Ten to fifteen μg of plasmid DNA was added and cells were kept on ice for 5 min. The cell-containing cuvette was placed in a Gene Pulser electroporation apparatus (Bio-Rad) and the cells were pulsed at 350 V, 25 μF. The cells were maintained on ice for an additional 10 min and then placed into a 100 mm culture dish containing 10 ml of growth medium.

8.1.3. PCR, DNA SEQUENCING AND VECTOR CONSTRUCTIONS

The fusion construct was synthesized using a recently described PCR technique (Ho, et al., 1989, Gene 77: 51; Kadowaki, et al., 1989, Gene 76: 161). Briefly, the full-length α-Gal A cDNA was subcloned into the pGEM plasmid and the resulting pG6-AGA plasmid was used for PCR amplification of the α-Gal A sequence with primers designed to delete the termination codon, to add a collagenase cleavage consensus sequence at the 3' end and to include an Eco RI recognition sequence at the 5' end of the cDNA (FIG.2). The sense primer was 5'-CCGAATTCATGCTGTCCGGT-CACCGTG-3' (SEQ ID NO:1) and the antisense primer was 5'-CGCCGGACCAGCCGGAAGTAAGCTTTTAATG-3' (SEQ ID NO:2). The protein A domain E (Nilsson, et. al., 1985, EMBO J. 4: 1075) was similarly amplified with the collagense consensus sequence in 5' oligonucletotide; the sense and antisense oligoncleotides were 5'-CCGGCTG-GTCCGGCGCAACACGATGAAGCT-3', (SEQ ID NO:3) and 5'-GGCCGAATTCCGGGATCCTTATTTTG-GAGCTTGAGA-3', (SEQ ID NO:4) respectively. The 1323 nt and 201 nt products of the α-Gal A and protein A PCR reactions were gel-purified on an 0.8% agarose gel and mixed together for the fusion PCR reaction. The sense primer from the α-Gal A reaction and the antisense primer from the protein A reaction were used for the final fusion reaction. The product of this reaction was digested with Eco RI and ligated into the Eco RI digested plasimid pGEM4Z. The protein A domain E and junctions between the linker and α-Gal A and protein A were confirmed by the deoxynucleotide chain termination sequencing method of Sanger (Hanahan & Meselson, 1998, Method Enzymol. 100:33). The confirmed fusion sequence then was digested with Eco RI and subcloned into the eukaryotic expression vector p91023(B).

8.2. RESULTS

8.2.1. CONSTRUCTION OF α-Gal A-PROTEIN A (AGA-PA) FUSION

FIG. 22 shows the strategy used for the construction of the α-Gal A-Protein A domain E fusion sequence. The full-length α-Gal A cDNA (1323 nt) and protein A domain E sequence (201 nt) were amplified separately and then fused by a second PCR amplification (FIG. 22) using the 5' α-Gal A cDNA sense primer (P1) and the 3' Protein A antisense primer (P4). The primers were designed to (a) eliminate the α-Gal A TAA stop codon; (b) insert the 16 nt collagenase cleavage consensus recognition sequence encoding Pro Ala Gly Pro (SEQ ID NO:5) between the α-Gal A and protein A cDNA sequence; and (c) introduce a TAA stop codon at the 3' end of protein A domain E. The integrity of this construct was confirmed by sequencing the protein A domain, linker and 3' of the α-Gal A cDNA (FIG. 23).

8.2.2. EXPRESSION OF pAGA-PA IN COS-1 CELLS

Seventy-two hours after transfection with the pAGA-PA construct, maximal levels of 4MU α-Gal activity were detected in cell extracts and in the spent culture media (Table VIII).

TABLE VIII

Transient Expression Of AGA-PA Construct In COS-1 Cells. Following Transfection A 7-Fold Increase In Endogenous α-Gal A Activity Was Observed. Also, An Increase Of α-Gal A In The Culture Media Was Observed

| COS-1 CELLS | α-Gal A Activity* | |
|---|---|---|
| | Cells (U/mg) | Media (U/ml) |
| Control | 210 | 0 |
| Transfected | 1,300 | 400 |

*Assayed using 4MU-α-Gal as substrate.

Compared to the endogenous α-Gal A activity in COS-1 cells of 210 U/mg, the transfected cells expressed 1300 U/mg. No α-Gal A activity was detected in the spent culture medium of uninfected COS-1 cells whereas 72 hours after transfection, 400 units of activity were secreted into the media.

8.2.3. AFFINITY PURIFICATION OF α-Gal A

The spent media from a single 100 mm dish of COS-cells was collected 72 hours after transection and applied to a column of IgG-Sepharose. Minimal activity of α-Gal A passed through the column during sample application (flow-through), or during the buffer wash (Table IX). However, more than 95% of the bound α-Gal A fusion protein was eluted by the addition of 0.5M acetic acid (elution buffer).

TABLE IX

IgG Sepharose Chromatography Of The α-Gal A Protein A Fusion Product From The Culture Media Of Transfected COS-1 Cells

| Purification Step | α-Gal A Activity* (U/ml) |
|---|---|
| Medium | 4,400 |
| Flow-Through | 10 |
| Buffer Wash | 0 |
| Elution** | 4,200 |

*Ten ml of culture media were applied to the column, washed and eluted as described in "Methods". α-Gal A activity was assayed using 4MU-α-Gal as substrate.
**0.5 M HAc, pH 3.4

8.2.4. RELEASE OF THE PROTEIN A DOMAIN FROM THE AGA-PA FUSION PROTEIN

The affinity purified fusion protein was treated with collagenase for 1 hour and the reaction products were rechromatographed on the IgG affinity column (Table X). The Protein A domain E was readily bound to the IgG column, whereas the human α-Gal A was eluted in the flow-through. Almost 90% of the applied activity was eluted. Based on the specific activity of the purified enzyme, it was estimated that this procedure resulted in 90% pure enzyme.

TABLE X

Treatment Of α-Gal A-Protein Fusion With Collagenase. Upon Treatment The Binding Of The IgG Column Decreased From 69% To 11%.

| STEP | % Of Recovered α-Gal A Activity* COLLAGENASE** | |
|---|---|---|
| | − | + |
| Flow-Through | 31 | 89 |
| Elution | 69 | 11 |

*Assayed using 4MU-α-Gal as substrate; a total of 4,200 units of α-Gal A activity was applied.
**Collagenase treatment for 1 hour at 25° C.

9. EXAMPLE: IN VIVO MODIFICATION OF RECOMBINANT HUMAN α-Gal A GLYCOSYLATION BY α2, 6-SIALYLTRANSFERASE

The example presented here describes a method whereby recombinant human α-Gal A enzyme is produced in a form that more closely resembles the native plasma glycoform of the enzyme. Specifically, human α-Gal A is produced in CHO cell lines that have been engineered to contain an α-2,6-sialyltransferase gene such that the α-Gal A protein made in these cell lines is sialylated. Results presented below demonstrate that the biologically active α-Gal A enzyme produced using such cell lines exhibit a broader tissue distribution, which can enhance this recombinant α-Gal A's therapeutic value.

9.1. MATERIALS AND METHODS

9.1.1. CONSTRUCTION OF THE α2,6-SIALYLTRANSFERASE EXPRESSION. VECTOR, pST26

The 1.6 kb rat CDNA (ST3) encoding the complete amino acid sequence of the α-galactoside α2,6-sialyltransferase (Gal α2,6ST; Weinstein et al., 1987, J. Biol. Chem. 262: 17735) was subcloned into the Bam HI site of the mammalian expression vector pRLDN, a gift from Smith, Kline and French Laboratories, resulting in the vector designated pST26. This construct was introduced by electroporation into the CHO cell line DG5.3-1000Mx, a high overexpressor of human α-galactosidase A. Clones were selected by growth in media containing 500 μg/ml of G418 to select for expression of the pST26 neo gene. Positive clones were individually isolated using cloning rings and then each was analyzed for expression of total secreted recombinant human α-galactosidase A. In addition, the percent of the secreted recombinant α-galactosidase A that contained α2,6-sialic acid residues was determined by *Sambucus nigra* agglutinin (SNA) chromatography on a column of SNA-Sepharose as described by Lee et al. (1989, J. Biol. Chem. 264:13848–13855).

9.1.2. SNA-LECTIN FLUORESCENCE MICROSCOPY

For fluorescence microscopy, positive DG5.3-1000Mx-ST26 clones were grown on 12-mm glass coverslips and then stained with fluorescein isothiocyanate (FITC)-tagged SNA as previously described (Lee et al., 1989, J. Biol. Chem. 264:13848–13855). Briefly, the cells were fixed with a fresh solution of 2% para-formaldehyde, 0.1% glutaraldehyde in phosphate buffered saline (PBS), pH 7.0, for 1 hr at 23° C., and subsequently blocked with 50 mM $NH_4Cl$ in PBS for 30 min at 23° C. Cells were incubated with FITC-SNA at a concentration of 25 mg/ml in PBS for 30 min at 23° C. Following washing in PBS, the coverslips were mounted in 15% vinol 205 polyvinol alcohol, 33% glycerol, 0.1% sodium azide in 100 mM Tris, pH 8.5. The cells were viewed with a Zeiss Photomat III fluorescence microscope and were photographed using Kodak Gold color film, ASA 25.

9.1.3. PURIFICATION OF RADIOLABELLED HUMAN α-GAL A WITH AND WITHOUT α2,6-SIALIC ACID RESIDUES

Parental DG5.3–1000Mx cells and modified DG5.3-ST26.1 cells were grown in 1 liter roller bottles ($\sim 5 \times 10^8$ cells) with 125 ml of DMEM, containing 10% dialyzed fetal calf serum (GIBCO, Grand Island, N.Y.) and 500 μCi[$^{35}$S]-methionine. The radioactive medium was replaced daily for three days, and the spent medium from each line was collected, pooled and concentrated using a stirred cell concentrator (Amicon, Beverly, Mass.). Approximately 2 mg ($4 \times 10^6$ U) of recombinant enzyme secreted from the DG5.3-1000Mx and DG5.3-1000Mx-ST26.1 cell lines, respectively, was individually purified to a specific activity of 100 cpm/U of enzyme. The purified, radiolabeled, secreted recombinant α-galactosidase A preparations (0.5 mg each) were treated individually with 5 units of acid phosphatase (Sigma) and the dephosphorylated forms also were used for intravenous injections.

9.1.4. IN VIVO HALF-LIFE AND TISSUE DISTRIBUTION OF RECOMBINANT α-GAL A

For the plasma half-life determinations, each radiolabelled α-Gal A form was injected into the tail vein of two CDI female mice. Each animal was bled through the sinus plexus at timed intervals over a 10–20 min period. Blood samples were centrifuged in an IEC Microhematocrit centrifuge and 50 μl of plasma was added to an aqueous scintillation fluid (AquaSol, NEN, Boston, Mass.) for counting. To assess the tissue distribution of the different enzyme forms, two mice for each enzyme were sacrificed by decapitation 4 hr after enzyme injection, selected tissues were removed, and the radioactivity in various tissues was determined and expressed per gram of tissue wet weight. Each value is the average of two independent experiments.

9.2. RESULTS

9.2.1. INTRODUCTION OF PST26 INTO DG5.3-1000Mx CHO CELLS AND DEMONSTRATION OF α2,6-SIALYLTRANSFERASE ACTIVITY IN G418-SELECTED CLONES

Following electroporation of the pST26 plasmid into CHO DG5.3-1000MX cells, transformed cells were selected which were resistant to the antibiotic G418. From the pool of resistant cells, 10 individual clones were isolated and expanded for further studies- These clones were designated DG5.3-1000Mx-ST26.1 to ST26.10. As evidence for the presence of α2,6-sialyltransferase activity in these cells, each cell line was stained with FITC-SNA and then examined by phase contrast and fluorescence microscopy. All ten of the DG5.3-1000Mx-ST26 cell lines were positively stained by the fluorescent lectin, indicating that various cell membrane glycoproteins served as acceptors for the expressed α2,6-sialyltransferase. In contrast, the FITC-lectin did not stain the parental DG5.3-1000Mx cells.

9.2.2. CHARACTERIZATION OF RECOMBINANT HUMAN SECRETED α2,6-SIALYLATED α-GAL A

Each of the ten DG5.3-1000Mx-ST26 cell lines and the parental DG5.3-1000Mx cells were grown in 100 mm dishes at the same cell density. The amount of secreted human α-Gal A activity per mg protein of total cultured cells was determined for each cell line. The DG5.3-1000Mx-ST26 lines secreted from 28 to 100% of the α-Gal A secreted by the parental cell line (16,000 U/mg protein, Table XI).

To determine the percent of the recombinant human secreted α-Gal A that contained α2,6-sialic acid residues, the secreted enzyme was chromatographed on the immobilized SNA column, and the bound enzyme was eluted with 0.4M lactose. As shown in Table XI, the individual clones had 55 to 100% of the applied enzymatic activity that was specifically bound and eluted from the lectin column. Notably, clone DG5.3-1000Mx-ST.1 produced the highest amount of recombinant α-Gal A, essentially all the enzyme form was sialylated and bound the immobilized SNA column. In contrast, recombinant α-Gal A secreted by the parental DG5.3-1000MX cells had little, if any binding to α2,6-sialic acid-specific lectin (Table XI).

TABLE XI

DG5.3-1000Mx-ST26 CHO Cell Lines
Secreting Human α2,6-Sialylated α-Galactosidase A

| Clone/ Subclone | Percent of Secreted α-Gal A Bound to SNA-Lectin | α-Gal A Secretion (% DG5.3-1000Mx*) |
| --- | --- | --- |
| DG5.3-1000MX | 5 | 100 |
| DG5.3-1000Mx-ST26 Subclones: | | |
| 1 | 100 | 100 |
| 2 | 99 | 76 |
| 3 | 93 | 72 |
| 4 | 79 | 70 |
| 5 | 74 | 64 |
| 6 | 73 | 85 |
| 7 | 72 | 85 |
| 8 | 55 | 84 |
| 9 | 51 | 81 |
| 10 | 28 | 79 |

*Activity is expressed as units per mg of cellular protein; The DG5.3-1000Mx line secreted ~16,000 U/mg.

9.2.3. PLASMA HALF-LIFE AND TISSUE DISTRIBUTION OF α2,6-SIALYLATED HUMAN α-GAL A IN MICE

To determine if the in vivo clearance of recombinant human α2,6-sialylated α-Gal A was different than that of the non-α2,6-sialylated enzyme, mice were injected with each form and their circulating half-lives were determined. As shown in FIG. 24A, the presence of α2,6-sialic acid moieties increased the half-life of the enzyme in the circulation from 14 to almost 30 min. Further, treatment of the α2,6-sialylated and non-α2,6-sialylated recombinant enzymes with acid phosphatase increased the in vivo plasma half-life of the non-α2,6-sialylated enzyme ($T_{1/2}$ from 14 to 24 min), whereas that of the phosphatase-treated α2,6-sialylated enzyme remained the same at about 28 min (FIG. 24B).

As depicted in FIG. 25, the presence or absence of α2,6-sialic acid moieties and/or phosphate residues, on the secreted recombinant human α-Gal A forms had a marked effect on their respective tissue distributions following intravenous administration to mice. A greater percentage of the total α2,6-sialylated α-Gal A injected was recovered in the lungs, kidney and heart, as compared to the non-α2,6-sialylated enzyme; in contrast, less of the α2,6-sialylated enzyme was recovered in the spleen. Interestingly, when the α2,6-sialylated enzyme was treated with acid phosphatase, the modified enzyme was redistributed to the liver and spleen, presumably to their reticuloendothelial cells (FIG. 25). Acid phosphatase treatment of the non-α2,6-sialylated enzyme resulted in the recovery of significantly more enzyme than its non-phosphatase treated form in the lungs and heart whereas, less was recovered in the kidney (FIG. 25).

EXAMPLE: OVEREXPRESSION OF HUMAN LYSOSOMAL PROTEINS RESULTS IN THEIR INTRACELLULAR AGGREGATION, CRYSTALLIZATION IN LYSOSOMES, AND SELECTIVE SECRETION

The example presented here describes a method, which is an inherent feature of the invention and was first noted while overexpressing α-Gal A, whereby certain proteins which are normally intracellularly targeted may be recombinantly expressed in a secreted form. Using several recombinant lysosomal enzymes, the results demonstrate that overexpression of such proteins in CHO cells presumably leads to aggregation which, in turn, causes the protein to be secreted, rather than being targeted to the intracellular vesicles, in this case, lysosomes, to which they would normally be sent. This surprising secretion feature facilitates easy purification of the recombinant protein produced.

10.1. MATERIALS AND METHODS

10.1.1. CONSTRUCTION OF PLASMIDS FOR LYSOSOMAL ENZYME OVERPRODUCTION

Construction of the α-Gal A expression construct, p91-AGA, has been described supra (Section 6.1.2). The analogous expression constructs for human α-N-acetylgalactosaminidase (designated p91-AGB) and acid sphingomyelinase (designated p91-ASM) and the respective transient expression of each in COS-1 cells have been described (Wang et al., 1990, J. Biol. Chem. 265: 21859–21866; Schuchman et al., 1991, J. Biol. Chem. 266: 8535–8539).

10.1.2. CELL CULTURE, ELECTROTRANSFECTION, AND GENE AMPLIFICATION

CHO cells were grown and maintained as described supra, in Section 6.1.3. Likewise, electroporation was performed as described supra, in Section 6.1.3.

Butyrate stimulation of the α-Gal A expressing CHO cells was performed as previously described (Dorner et al., 1989 J. Biol. Chem. 264:20602–20607). Briefly, cells were plated in 100 mm dishes and allowed to grow in 10 ml of DMEM supplemented with 10% dFCS for 2 days. The media was removed and replaced with 10 ml of DMEM supplemented with 10% dFCS containing 5 mM sodium butyrate. Cells were incubated for 16 hr at 37° C. in a $CO_2$ incubator and then cells and culture media were harvested and the α-Gal A activity was determined.

10.1.3. ULTRASTRUCTURAL AND IMMUNOLABELING STUDIES

DG5.3-1000Mx cells were grown to confluency in 100 mm dishes. Following trypsinization (0.25% trypsin, EDTA), they were washed twice in phosphate buffered saline (PBS) and pelleted at 1,500 g for 5 min at room temperature. Cells were then fixed for 1 hr with 3% glutaraldehyde in PBS, followed by fixation in PBS-buffered 1% $OsO_4$ for 30 min at room temperature. Samples were then dehydrated with graded steps of ethanol, infiltrated with propylene oxide and embedded in Embed 812 (Electron Microscopy Sciences, Fort Washington, Pa.). 1 µm sections were cut from representative areas. Ultrathin sections were prepared and stained with uranyl acetate and lead citrate, and then were viewed with an electron microscope (JEM 100 CX, Jeol. U.S.A., Peabody, Mass.).

For immunodetection, sections were prepared as above, and after embedding, they were mounted on Formvar-coated nickel grids (Formvar Scientific, Marietta, Ohio), incubated with goat serum in PBS for 30 min at 37° C. to block nonspecific binding, washed six times with PBS and then incubated with affinity-purified rabbit anti-α-Gal A antibodies for 1 hr. The sections were washed extensively as above and then were incubated with 10 nm gold particles conjugated to protein A (Amersham Corp., Arlington, Ill.) for 1 hr at 37° C. After washing with PBS, sections were fixed with 3% glutaraldehyde in PBS for 15 min at room temperature, washed again with PBS and then examined under the electron microscope.

10.1.4. SDS-PAGE AND AUTORADIOGRAPHY

PAGE gel electrophoresis was carried out under reducing conditions as described by Laemmli (1970 Nature (London) 277:680–685) in 1.5 mm thick slab gels containing 10% acrylamide. The gel was fixed in 10% acetic acid and 20% methanol for 30 min and then soaked in Amplify (Amersham Corp.) for 30 min with agitation. Gels were vacuum dried for 90 min (Hoffer Scientific Instruments, San Francisco, Calif.) and then autoradiographed with Kodak X Omat AR film (Eastman Kodak Co.) for 4–24 hrs.

10.1.5. IN VITRO STUDIES OF α-GAL A AGGREGATION

The possible formation of insoluble α-Gal A aggregates at varying enzyme and hydrogen ion concentrations was investigated. Using a stock solution of purified, secreted α-Gal A (16 mg/ml in 10 mM Tris buffer, pH 7.0), appropriate aliquots were placed in glass borosilicate tubes and the volumes were brought to 200 µl with distilled water so that with the addition of 100 µl of the appropriate buffer (0.5M 2-(N-morpholino)ethanesulfonic acid, at pH 5.0, 5.5, 6.0, 6.5 or 7.0), the final α-Gal A concentrations (0.1–10 mg/ml) would be achieved at specific pH values. After incubation for 10 min at room temperature, the turbidity of each solution was determined by measuring the OD at 650 nm in a spectrophotometer (Spectronic 1201, Milton Roy Co., Rochester, N.Y.) using a 1-cm path cuvette. As a control, 1 mg/ml of purified, secreted α-Gal A was mixed with increasing BSA concentrations (0.1–10 mg/ml) and the turbidity of each solution was determined. Similar experiments were performed with solutions of α-Gal A (10 mg/ml) and BSA (2 mg/ml), at decreasing pH (from pH 7.0 to 5.0). After incubation and centrifugation as above, the supernatants and pellets were subjected to SDS-PAGE.

10.1.6. ENZYME AND PROTEIN ASSAYS

The α-Gal A activities in the cell lysates and media were determined using 5 mM 4-methylumbelliferyl-α-D-galactopyranoside (4MU-α-Gal) (Genzyme Corp., Cambridge, Mass.) as previously described (Bishop and Desnick, 1981 J. Biol. Chem. 256:1307–1316). Briefly, a stock solution of 5 mM 4MU-α-Gal was prepared in 0.1M citrate/0.2M phosphate buffer, pH 4.6, in an ultrasonic bath. The reaction mixture, containing 10–50 µl of cell extract and 150 µl of the stock substrate solution, was incubated at 37° C. for 10 to 30 min. The reaction was terminated with the addition of 2.3 ml of 0.1M ethylenediamine. The fluorescence was determined using a Ratio-2 System Fluorometer (Optical Technology Devices, Elmsford, N.Y.). 1U of activity is the amount of enzyme that hydrolyzed one nmol of substrate per hour. The activities of α-mannosidase, β-galactosidase, β-hexosaminidase, β-glucuronidase, acid phosphatase and α-N-acetylgalactosaminidase were measured using the appropriate 4-methylumbelliferyl substrate. The activity of acid sphingomyelinase was determined according to Gal et al. (1975, N. Eng. J. Med. 293:632–636). Protein concentrations were quantitated by the fluorescamine method (Bohlen et al., 1973, Arch. Biochem. Biophys. 155:213–220) as modified by Bishop et al. (1978, Biochem. Biophys. Acta 524:109–120).

10.2. RESULTS

10.2.1. OVEREXPRESSION RESULTS IN CRYSTALLINE STRUCTURES CONTAINING HUMAN α-GAL A IN MEMBRANE-LIMITED VESICLES

Figure 26A:
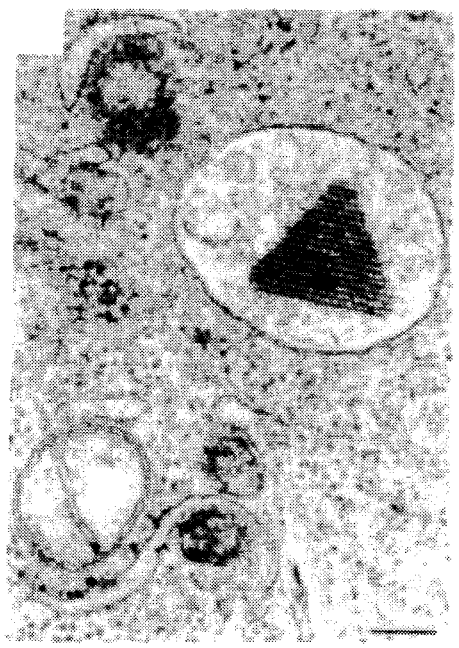
Figure 26B:
Figure 26C:
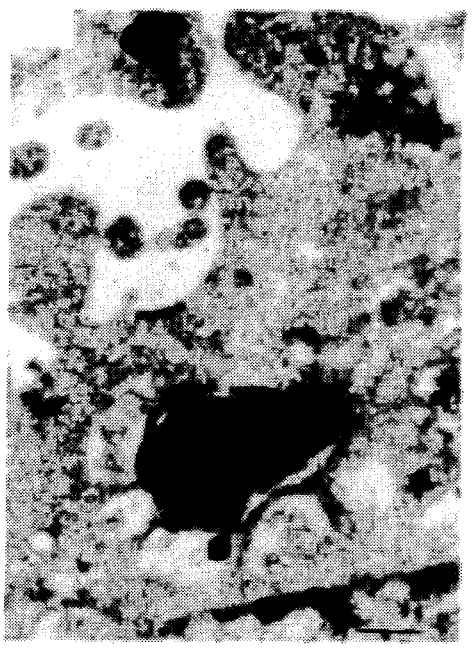
Figure 26D:
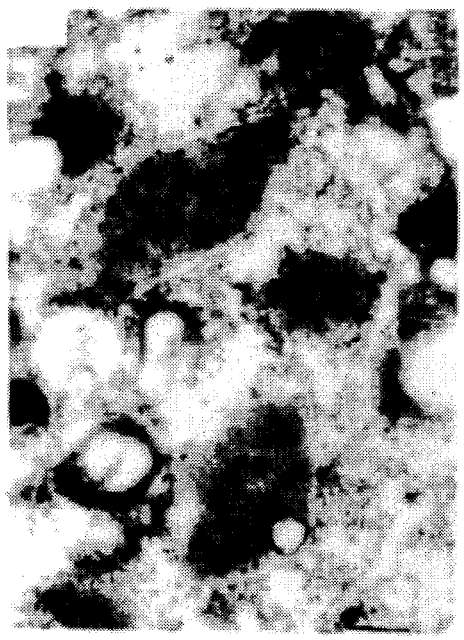
Figure 26E:
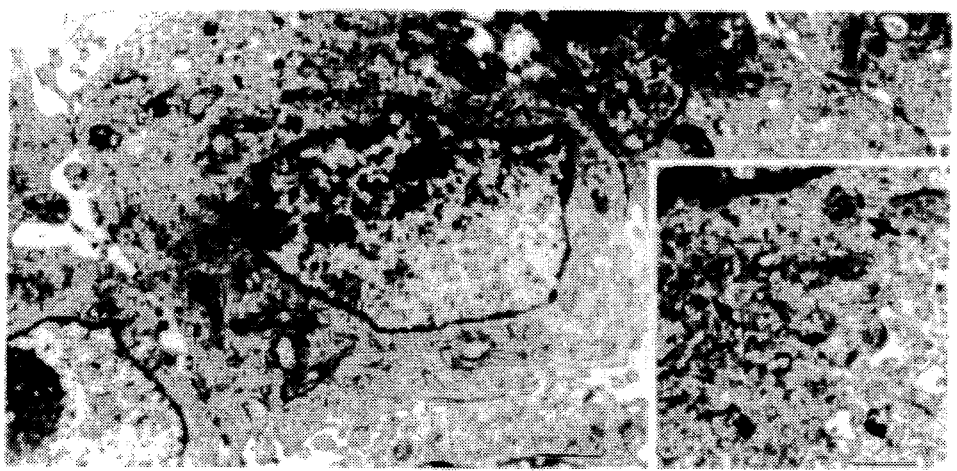

Ultrastructural examination of the stably amplified DG5.3–1000Mx cells revealed numerous 0.25 to 1.5 µm crystalline bodies which had ordered triangular lattices in membrane-limited vesicles throughout the cytoplasm (FIG. 26A and 26B). the repeat within these crystalline structures was about 20 nm. these structures were particularly abundant in lysosomes (FIG. 28A) and in vesicles which appeared to be dilated TGN (FIG. 28B) (Hand and Oliver, 1984, J. Histochem. Cytochem. 42: 403–442; Griffith and Simons, 1986, Science 234:438–443; McCracken, 1991, in Intracellular Traficking of Proteins, Steer and Hanover, eds., Cambridge University Press, New York pp. 461–485). Of note, normal Golgi structures were not observed in these cells, whereas Golgi complexes were readily identified in the parental DG44 cells (FIG. 26E, inset). When osmium-glutaraldehyde fixed sections of the DG5.3–1000Mx cells were incubated with affinity-purified rabbit anti-human α-Gal A antibodies and then with protein A-conjugated gold, these crystalline structures were specifically stained by gold particles (FIG. 26C and 26D). That the crystalline structures were immunogold labeled, even though the sections were fixed in osmium-glutaraldehyde, suggested that these structures were primarily, if not solely, composed of the human enzyme.

To determine whether the crystalline structures were present in clones expressing lower levels of α-Gal A, clones DG5.3–0Mx, –1.3Mx, –250Mx, and –1000Mx were grown to confluency and examined by electron microscopy. Although the TGN was increasingly dilated with increasing α-Gal A expression, only the DG5.3–1000Mx clone contained crystalline arrays in lysosomes. Similarly, clone DG5.3-1.3Mx was stimulated with 5mM sodium butyrate for 18 hrs to increase transcription of the integrated vector containing the α-Gal A cDNA and then examined ultrastructurally. Compared to the untreated clone, butyrate treatment resulted in the presence of dilated organelles including many membrane-bound structures containing dense material. These results indicated that crystal formation was α-Gal A concentration dependent. Furthermore, to assess whether crystal formation was specific to α-Gal A, clone AGB14.8-1000Mx, which overexpresses α-N-Acetylgalactosaminidase, was examined. No crystalline arrays were observed, but numerous dilated structures were seen similar to those in the DG5.3-1.3Mx clone, suggesting that expression of the recombinant α-N-acetylgalactosaminidase had not reached the critical level necessary for crystal formation.

10.2.2. α-GAL A AND α-N-ACETYLGALACTOSAMINIDASE AGGREGATE AT HIGH CONCENTRATION AND LOW pH

Since it was conceivable that the overexpression of α-Gal A resulted in the formation of soluble and particulate aggregates that did not bind to or were inefficiently bound by the M6PR and/or the sulfotransferase in the TGN, the possible aggregation of α-Gal A was assessed in vitro at varying enzyme and hydrogen ion concentrations. As shown in FIG. 27A, the amount of α-Gal A precipitated, compared to about 30% ($>2\times10^6$U) at pH 5.0. At pH 6.0, the estimated pH of the TGN (Griffith and Simons, 1986, Science 234: 438–443), about 12% of the enzyme formed particulate aggregates that could be pelleted by centrifugation at 15,000×g. FIG. 27B shows that the turbidity, as a measure of aggregation (Halper and Stere, 1977, Arch. Biochem. Biophys. 184: 529–534), of solutions containing 0.1 to 10 mg/ml of α-Gal A at either pH 5.0 or 7.0 increased as a function of enzyme concentration. Moreover, the turbidity of a 1 mg/ml α-Gal A solution was essentially unaffected by the presence of increasing albumin concentrations from 0.1 to 10 mg/ml at pH 5.0 (FIG. 27B; control). Finally, electrophoresis of the supernatant and pellet fractions from solutions containing α-Gal A (10 mg/ml) and bovine serum albumin (BSA) (2 mg/ml) incubated at varying hydrogen ion concentrations revealed that the increasing precipitation of α-Gal A with decreasing pH was enzyme specific, as the BSA did not precipitate over this pH range (FIG. 27C).

10.3. DISCUSSION

An "aggregation-secretion" model is proposed to account for the rerouting of human α-Gal A as a prototype for overproduced targeted proteins. As depicted in FIG. 28, the overproduced enzyme is normally synthesized and processed until it reaches the trans-Golgi network (TGN). In this structure, the overproduced enzyme is accumulated and subjected to a markedly more acidic environment, (app. pH 6.0), which leads to increased protein-protein interactions that generate soluble and particulate α-Gal A aggregates. As a result of such aggregation, the enzyme's M6P moieties become inaccessible or less accessible for binding to the MGPR. The aggregates with inaccessible MGP moieties, by default, are rerouted via the constitutive secretory pathway (Helms et al., 1990, J. Biol. Chem. 265: 20,027–20,032).

The cellular response, therefore, to the overproduction of lysosome-targeted protein is to transport those proteins having available MGP residues to the lysosome and to reroute the majority of the overproduced, and presumably aggregated, proteins through the constitutive secretion pathway. The fact that large amounts of recombinant human α-Gal A are secreted by CHO cells permits the scaled-up production and easy purification of the recombinant enzyme for crystallography and for trials of enzyme replacement therapy in patients with Fabry disease. In addition, it is clear that the amplification series of overexpressing α-Gal A CHO cells provides a unique experimental mammalian system to efficiently characterize the biosynthesis, posttranslational modifications, and mechanisms responsible for the lysosomal targeting and selective secretion of this prototype lysosomal enzyme, thereby providing further insight into the nature of protein transport and sorting in mammalian cells.

Thus, the overexpression of lysosomal and perhaps other targeted proteins in CHO cells provides a convenient method for producing large amounts of the protein for structural analyses and/or therapeutic applications, as well as providing a useful approach to study protein biosynthesis and sorting.

11. DEPOSIT OF MICROORGANISMS

The following *E. coli* strains carrying the listed plasmids have been deposited with the Agricultural Research Culture Collection (NRRL), Peoria, Ill. and have been assigned the following accession number:

| Host Cell | Strain | Plasmid | Accession No. |
|-----------|--------|---------|---------------|
| *E. coli* | k12    | p91.AGA | B 18722       |
| *E. Coli* | k12    | pAGA-PA | B 18723       |

The present invention is not to be limited in scope by the microorganisms deposited since the deposited embodiments are intended as illustration of individual aspects of the invention and any microorganisms, or constructs which are functionally equivalent are within the scope of this invention. Indeed various modifications of the invention in addition to those shown and described herein will become apparent to those skilled in the art from the foregoing description and accompanying drawings. Such modifications are intended to fall within the scope of the appended claims.

---

What is claimed is:

1. A method of producing human α-galactosidase A, comprising:
   a. culturing a mammalian cell transformed with a recombinant vector which includes a nucleotide sequence encoding a cleavage site sandwiched between an α-galactosidase A coding sequence and a protein A domain E coding sequence arranged in the same translational reading frame, controlled by a second nucleotide sequence that regulates gene expression so that a fusion protein is expressed by the transformed host cell;
   b. recovering the fusion protein from the culture;
   c. treating the fusion protein with a substance that cleaves the cleavage site so that the α-galactosidase A is separated from the protein A domain E protein; and
   d. recovering the separated α-galactosidase A.

2. The method according to claim 1 in which the fusion protein is recovered from the culture by reaction with an immunoglobulin binding partner for the protein A domain E protein.

3. The method according to claim 2 in which the immunoglobulin binding partner is immobilized.

4. The method according to claim 1 in which the recombinant vector is pAGA-PA as deposited with the Agricultural Research Culture collection having accession number B-18723.

5. A method of producing human α-galactosidase A, comprising:
   a. culturing a mammalian cell transformed with a recombinant vector which includes a nucleotide sequence encoding a cleavage site sandwiched between an α-galactosidase A coding sequence and a protein antigen coding sequence arranged in the same translational reading frame, controlled by a second nucleotide sequence that regulates gene expression so that a fusion protein is expressed by the transformed host cell;
   b. recovering the fusion protein from the culture by reaction with an immunoglobulin directed against the protein antigen;
   c. treating the fusion protein with a substance that cleaves the cleavage site so that the α-galactosidase A is separated from the protein antigen; and
   d. recovering the separated α-galactosidase A.

6. The method according to claim 5 in which the immunoglobulin is immobilized.

7. The method according to claim 1 or 5 in which the substance that cleaves the cleavage site is an enzyme and the cleavage site is a substrate specific for the enzyme.

8. The method according to claim 7 in which the enzyme is collagenase.

9. The method according to claim 1 or 5 in which a α-galactosidase A coding sequence comprises the sequence depicted in FIG. 1A from nucleotide number 1 to 1299.

10. The method according to claim 1 or 5 in which the α-galactosidase A coding sequence comprises the sequence depicted in FIG. 1A from nucleotide number 91 to 1299.

11. A recombinant vector comprising a nucleotide sequence encoding a cleavage site sandwiched between an α-galactosidase A coding sequence and a protein A domain E coding sequence arranged in the same translational reading frame, controlled by a second nucleotide sequence that regulates the expression of a fusion protein in a mammalian host cell.

12. A recombinant vector pAGA-pA as deposited with the Agricultural Research Culture Collection having accession number B 18723.

13. A recombinant vector comprising a nucleotide sequence encoding a cleavage site sandwiched between an α-galactosidase A coding sequence and a protein antigen coding sequence arranged in the same translational reading frame, controlled by a second nucleotide sequence that regulates the expression of a fusion protein in a mammalian host cell.

14. The recombinant vector of claim 11 or 13 which further includes a nucleotide sequence encoding a selectable marker.

15. The recombinant vector of claim 11 or 13 in which the cleavage site is a collagenase substrate.

* * * * *

UNITED STATES PATENT AND TRADEMARK OFFICE
CERTIFICATE OF CORRECTION

| | | |
|---|---|---|
| PATENT NO. | : 5,580,757 | |
| APPLICATION NO. | : 08/261577 | |
| DATED | : December 3, 1996 | |
| INVENTOR(S) | : Robert Desnick et al. | |

It is certified that error appears in the above-identified patent and that said Letters Patent is hereby corrected as shown below:

At col. 1, line 9:

STATEMENT REGARDING FEDERALLY SPONSORED RESEARCH OR DEVELOPMENT

-- This invention was made with government support under grant No. DK-34045 awarded by the National Institutes of Health. The government has certain rights in the invention. --

Signed and Sealed this
Twenty-eighth Day of June, 2011

David J. Kappos
*Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CCGAATTCAT GCTGTCCGGT CACCGTG    27

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGCCGGACCA GCCGGAAGTA AGTCTTTTAA TG    32

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGGCTGGTC CGGCGCAACA CGATGAAGCT    30

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGCCGAATTC CGGGATCCTT ATTTGGAGC TTGAGA    36

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:5:

Pro Ala Gly Pro
    1

(2) INFORMATION FOR SEQ ID NO:6:

(i) SEQUENCE CHARACTERISTICS:
        (A) LENGTH: 1393 base pairs
        (B) TYPE: nucleic acid
        (C) STRANDEDNESS: double
        (D) TOPOLOGY: unknown ( i i ) MOLECULE TYPE: DNA (genomic)

( i x ) FEATURE:
  ( A ) NAME/KEY: CDS
  ( B ) LOCATION: 61..1350

( x i ) SEQUENCE DESCRIPTION: SEQ ID NO:6:

```
AGGTTAATCT TAAAAGCCCA GGTTACCCGC GGAAATTTAT GCTGTCCGGT CACCGTGACA          60

ATG CAG CTG AGG AAC CCA GAA CTA CAT CTG GGC TGC GCG CTT GCG CTT          108
Met Gln Leu Arg Asn Pro Glu Leu His Leu Gly Cys Ala Leu Ala Leu
 1           5                  10                  15

CGC TTC CTG GCC CTC GTT TCC TGG GAC ATC CCT GGG GCT AGA GCA CTG          156
Arg Phe Leu Ala Leu Val Ser Trp Asp Ile Pro Gly Ala Arg Ala Leu
             20                  25                  30

GAC AAT GGA TTG GCA AGG ACG CCT ACC ATG GGC TGG CTG CAC TGG GAG          204
Asp Asn Gly Leu Ala Arg Thr Pro Thr Met Gly Trp Leu His Trp Glu
         35                  40                  45

CGC TTC ATG TGC AAC CTT GAC TGC CAG GAA GAG CCA GAT TCC TGC ATC          252
Arg Phe Met Cys Asn Leu Asp Cys Gln Glu Glu Pro Asp Ser Cys Ile
     50                  55                  60

AGT GAG AAG CTC TTC ATG GAG ATG GCA GAG CTC ATG GTC TCA GAA GGC          300
Ser Glu Lys Leu Phe Met Glu Met Ala Glu Leu Met Val Ser Glu Gly
 65                  70                  75                  80

TGG AAG GAT GCA GGT TAT GAG TAC CTC TGC ATT GAT GAC TGT TGG ATG          348
Trp Lys Asp Ala Gly Tyr Glu Tyr Leu Cys Ile Asp Asp Cys Trp Met
                 85                  90                  95

GCT CCC CAA AGA GAT TCA GAA GGC AGA CTT CAG GCA GAC CCT CAG CGC          396
Ala Pro Gln Arg Asp Ser Glu Gly Arg Leu Gln Ala Asp Pro Gln Arg
            100                 105                 110

TTT CCT CAT GGG ATT CGC CAG CTA GCT AAT TAT GTT CAC AGC AAA GGA          444
Phe Pro His Gly Ile Arg Gln Leu Ala Asn Tyr Val His Ser Lys Gly
        115                 120                 125

CTG AAG CTA GGG ATT TAT GCA GAT GTT GGA AAT AAA ACC TGC GCA GGC          492
Leu Lys Leu Gly Ile Tyr Ala Asp Val Gly Asn Lys Thr Cys Ala Gly
    130                 135                 140

TTC CCT GGG AGT TTT GGA TAC TAC GAC ATT GAT GCC CAG ACC TTT GCT          540
Phe Pro Gly Ser Phe Gly Tyr Tyr Asp Ile Asp Ala Gln Thr Phe Ala
145                 150                 155                 160

GAC TGG GGA GTA GAT CTG CTA AAA TTT GAT GGT TGT TAC TGT GAC AGT          588
Asp Trp Gly Val Asp Leu Leu Lys Phe Asp Gly Cys Tyr Cys Asp Ser
                165                 170                 175

TTG GAA AAT TTG GCA GAT GGT TAT AAG CAC ATG TCC TTG GCC CTG AAT          636
Leu Glu Asn Leu Ala Asp Gly Tyr Lys His Met Ser Leu Ala Leu Asn
            180                 185                 190

AGG ACT GGC AGA AGC ATT GTG TAC TCC TGT GAG TGG CCT CTT TAT ATG          684
Arg Thr Gly Arg Ser Ile Val Tyr Ser Cys Glu Trp Pro Leu Tyr Met
        195                 200                 205

TGG CCC TTT CAA AAG CCC AAT TAT ACA GAA ATC CGA CAG TAC TGC AAT          732
Trp Pro Phe Gln Lys Pro Asn Tyr Thr Glu Ile Arg Gln Tyr Cys Asn
210                 215                 220

CAC TGG CGA AAT TTT GCT GAC ATT GAT GAT TCC TGG AAA AGT ATA AAG          780
His Trp Arg Asn Phe Ala Asp Ile Asp Asp Ser Trp Lys Ser Ile Lys
225                 230                 235                 240

AGT ATC TTG GAC TGG ACA TCT TTT AAC CAG GAG AGA ATT GTT GAT GTT          828
Ser Ile Leu Asp Trp Thr Ser Phe Asn Gln Glu Arg Ile Val Asp Val
            245                 250                 255

GCT GGA CCA GGG GGT TGG AAT GAC CCA GAT ATG TTA GTG ATT GGC AAC          876
Ala Gly Pro Gly Gly Trp Asn Asp Pro Asp Met Leu Val Ile Gly Asn
        260                 265                 270

TTT GGC CTC AGC TGG AAT CAG CAA GTA ACT CAG ATG GCC CTC TGG GCT          924
Phe Gly Leu Ser Trp Asn Gln Gln Val Thr Gln Met Ala Leu Trp Ala
```

```
                    275                         280                           285
ATC ATG GCT GCT CCT TTA TTC ATG TCT AAT GAC CTC CGA CAC ATC AGC              972
Ile Met Ala Ala Pro Leu Phe Met Ser Asn Asp Leu Arg His Ile Ser
    290                 295                 300

CCT CAA GCC AAA GCT CTC CTT CAG GAT AAG GAC GTA ATT GCC ATC AAT             1020
Pro Gln Ala Lys Ala Leu Leu Gln Asp Lys Asp Val Ile Ala Ile Asn
305                 310                 315                 320

CAG GAC CCC TTG GGC AAG CAA GGG TAC CAG CTT AGA CAG GGA GAC AAC             1068
Gln Asp Pro Leu Gly Lys Gln Gly Tyr Gln Leu Arg Gln Gly Asp Asn
                325                 330                 335

TTT GAA GTG TGG GAA CGA CCT CTC TCA GGC TTA GCC TGG GCT GTA GCT             1116
Phe Glu Val Trp Glu Arg Pro Leu Ser Gly Leu Ala Trp Ala Val Ala
        340                 345                 350

ATG ATA AAC CGG CAG GAG ATT GGT GGA CCT CGC TCT TAT ACC ATC GCA             1164
Met Ile Asn Arg Gln Glu Ile Gly Gly Pro Arg Ser Tyr Thr Ile Ala
            355                 360                 365

GTT GCT TCC CTG GGT AAA GGA GTG GCC TGT AAT CCT GCC TGC TTC ATC             1212
Val Ala Ser Leu Gly Lys Gly Val Ala Cys Asn Pro Ala Cys Phe Ile
370                 375                 380

ACA CAG CTC CTC CCT GTG AAA AGG AAG CTA GGG TTC TAT GAA TGG ACT             1260
Thr Gln Leu Leu Pro Val Lys Arg Lys Leu Gly Phe Tyr Glu Trp Thr
385                 390                 395                 400

TCA AGG TTA AGA AGT CAC ATA AAT CCC ACA GGC ACT GTT TTG CTT CAG             1308
Ser Arg Leu Arg Ser His Ile Asn Pro Thr Gly Thr Val Leu Leu Gln
                405                 410                 415

CTA GAA AAT ACA ATG CAG ATG TCA TTA AAA GAC TTA CTT TAAAAAAAA               1357
Leu Glu Asn Thr Met Gln Met Ser Leu Lys Asp Leu Leu
                420                 425                 430

AAAAAAAAAA AAAAAAAAAA AAAAAAAAAA AAAAA                                      1393
```

( 2 ) INFORMATION FOR SEQ ID NO:7:

( i ) SEQUENCE CHARACTERISTICS:
        ( A ) LENGTH: 429 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Asp | Trp | Gly | Val | Asp | Leu | Leu | Lys | Phe | Asp | Gly | Cys | Tyr | Cys | Asp | Ser |
|     |     |     |     | 165 |     |     |     |     | 170 |     |     |     |     | 175 |     |
| Leu | Glu | Asn | Leu | Ala | Asp | Gly | Tyr | Lys | His | Met | Ser | Leu | Ala | Leu | Asn |
|     |     |     | 180 |     |     |     |     | 185 |     |     |     |     | 190 |     |     |
| Arg | Thr | Gly | Arg | Ser | Ile | Val | Tyr | Ser | Cys | Glu | Trp | Pro | Leu | Tyr | Met |
|     |     | 195 |     |     |     |     | 200 |     |     |     |     | 205 |     |     |     |
| Trp | Pro | Phe | Gln | Lys | Pro | Asn | Tyr | Thr | Glu | Ile | Arg | Gln | Tyr | Cys | Asn |
|     | 210 |     |     |     |     | 215 |     |     |     |     | 220 |     |     |     |     |
| His | Trp | Arg | Asn | Phe | Ala | Asp | Ile | Asp | Asp | Ser | Trp | Lys | Ser | Ile | Lys |
| 225 |     |     |     |     | 230 |     |     |     |     | 235 |     |     |     |     | 240 |
| Ser | Ile | Leu | Asp | Trp | Thr | Ser | Phe | Asn | Gln | Glu | Arg | Ile | Val | Asp | Val |
|     |     |     |     | 245 |     |     |     |     | 250 |     |     |     |     | 255 |     |
| Ala | Gly | Pro | Gly | Gly | Trp | Asn | Asp | Pro | Asp | Met | Leu | Val | Ile | Gly | Asn |
|     |     |     | 260 |     |     |     |     | 265 |     |     |     |     | 270 |     |     |
| Phe | Gly | Leu | Ser | Trp | Asn | Gln | Gln | Val | Thr | Gln | Met | Ala | Leu | Trp | Ala |
|     |     | 275 |     |     |     |     | 280 |     |     |     |     | 285 |     |     |     |
| Ile | Met | Ala | Ala | Pro | Leu | Phe | Met | Ser | Asn | Asp | Leu | Arg | His | Ile | Ser |
|     | 290 |     |     |     |     | 295 |     |     |     |     | 300 |     |     |     |     |
| Pro | Gln | Ala | Lys | Ala | Leu | Leu | Gln | Asp | Lys | Asp | Val | Ile | Ala | Ile | Asn |
| 305 |     |     |     |     | 310 |     |     |     |     | 315 |     |     |     |     | 320 |
| Gln | Asp | Pro | Leu | Gly | Lys | Gln | Gly | Tyr | Gln | Leu | Arg | Gln | Gly | Asp | Asn |
|     |     |     |     | 325 |     |     |     |     | 330 |     |     |     |     | 335 |     |
| Phe | Glu | Val | Trp | Glu | Arg | Pro | Leu | Ser | Gly | Leu | Ala | Trp | Ala | Val | Ala |
|     |     |     | 340 |     |     |     |     | 345 |     |     |     |     | 350 |     |     |
| Met | Ile | Asn | Arg | Gln | Glu | Ile | Gly | Gly | Pro | Arg | Ser | Tyr | Thr | Ile | Ala |
|     |     | 355 |     |     |     |     | 360 |     |     |     |     | 365 |     |     |     |
| Val | Ala | Ser | Leu | Gly | Lys | Gly | Val | Ala | Cys | Asn | Pro | Ala | Cys | Phe | Ile |
|     | 370 |     |     |     |     | 375 |     |     |     |     | 380 |     |     |     |     |
| Thr | Gln | Leu | Leu | Pro | Val | Lys | Arg | Lys | Leu | Gly | Phe | Tyr | Glu | Trp | Thr |
| 385 |     |     |     |     | 390 |     |     |     |     | 395 |     |     |     |     | 400 |
| Ser | Arg | Leu | Arg | Ser | His | Ile | Asn | Pro | Thr | Gly | Thr | Val | Leu | Leu | Gln |
|     |     |     |     | 405 |     |     |     |     | 410 |     |     |     |     | 415 |     |
| Leu | Glu | Asn | Thr | Met | Gln | Met | Ser | Leu | Lys | Asp | Leu | Leu |     |     |     |
|     |     |     | 420 |     |     |     |     | 425 |     |     |     |     |     |     |     |

( 2 ) INFORMATION FOR SEQ ID NO:8:

( i ) SEQUENCE CHARACTERISTICS:
        ( A ) LENGTH: 411 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

| Met | Leu | Leu | Lys | Thr | Val | Leu | Leu | Leu | Gly | His | Val | Ala | Gln | Val | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Met | Leu | Asp | Asn | Gly | Leu | Leu | Gln | Thr | Pro | Pro | Met | Gly | Trp | Leu | Ala |
|     |     |     | 20  |     |     |     |     | 25  |     |     |     |     | 30  |     |     |
| Trp | Glu | Arg | Phe | Arg | Cys | Asn | Ile | Asn | Cys | Asp | Glu | Asp | Pro | Lys | Asn |
|     |     | 35  |     |     |     |     | 40  |     |     |     |     | 45  |     |     |     |
| Cys | Ile | Ser | Glu | Gln | Leu | Phe | Met | Glu | Met | Ala | Asp | Arg | Met | Ala | Gln |
|     | 50  |     |     |     |     | 55  |     |     |     |     | 60  |     |     |     |     |
| Asp | Gly | Trp | Arg | Asp | Met | Gly | Tyr | Thr | Tyr | Leu | Asn | Ile | Asp | Asp | Cys |
| 65  |     |     |     |     | 70  |     |     |     |     | 75  |     |     |     |     | 80  |

| | | | | | | | | | | | | | | |
|---|---|---|---|---|---|---|---|---|---|---|---|---|---|---|
| Trp | Ile | Gly | Gly | Arg<br>85 | Asp | Ala | Ser | Gly | Arg<br>90 | Leu | Met | Pro | Asp<br>95 | Lys |
| Arg | Phe | Pro | His | Gly<br>100 | Ile | Pro | Phe<br>105 | Leu | Ala | Asp | Tyr | Val<br>110 | His | Ser | Leu |
| Gly | Leu | Lys<br>115 | Leu | Gly | Ile | Tyr | Ala<br>120 | Asp | Met | Gly | Asn | Phe<br>125 | Thr | Cys | Met |
| Gly | Tyr<br>130 | Pro | Gly | Thr | Thr | Leu<br>135 | Asp | Lys | Val | Val | Gln<br>140 | Asp | Ala | Gln | Thr |
| Phe<br>145 | Ala | Glu | Trp | Lys | Val<br>150 | Asp | Met | Leu | Lys | Leu<br>155 | Asp | Gly | Cys | Phe | Ser<br>160 |
| Thr | Pro | Glu | Glu | Arg<br>165 | Ala | Gln | Gly | Tyr | Pro<br>170 | Lys | Met | Ala | Ala | Ala<br>175 | Leu |
| Asn | Ala | Thr | Gly<br>180 | Arg | Pro | Ile | Ala | Phe<br>185 | Ser | Cys | Ser | Trp | Pro<br>190 | Ala | Tyr |
| Glu | Gly | Gly<br>195 | Leu | Pro | Pro | Arg | Val<br>200 | Asn | Tyr | Ser | Leu | Leu<br>205 | Ala | Asp | Ile |
| Cys | Asn<br>210 | Leu | Trp | Arg | Asn | Tyr<br>215 | Asp | Asp | Ile | Gln | Asp<br>220 | Ser | Trp | Trp | Ser |
| Val<br>225 | Leu | Ser | Ile | Leu | Asn<br>230 | Trp | Phe | Val | Glu | His<br>235 | Gln | Asp | Ile | Leu | Gln<br>240 |
| Pro | Val | Ala | Gly | Pro<br>245 | Gly | His | Trp | Asn | Asp<br>250 | Pro | Asp | Met | Leu | Leu<br>255 | Ile |
| Gly | Asn | Phe | Gly<br>260 | Leu | Ser | Leu | Glu | Gln<br>265 | Arg | Ser | Arg | Ala | Gln<br>270 | Met | Ala |
| Leu | Trp | Thr<br>275 | Val | Leu | Ala | Ala | Pro<br>280 | Leu | Leu | Met | Ser | Thr<br>285 | Asp | Leu | Arg |
| Thr | Ile<br>290 | Ser | Ala | Gln | Asn | Met<br>295 | Asp | Ile | Leu | Gln | Asn<br>300 | Pro | Leu | Met | Ile |
| Lys<br>305 | Ile | Asn | Gln | Asp | Pro<br>310 | Leu | Gly | Ile | Gln | Gly<br>315 | Arg | Ile | His | Lys | Glu<br>320 |
| Lys | Ser | Leu | Ile | Glu<br>325 | Val | Tyr | Met | Arg | Pro<br>330 | Leu | Ser | Asn | Lys | Ala<br>335 | Ser |
| Ala | Leu | Val | Phe<br>340 | Phe | Ser | Cys | Arg | Thr<br>345 | Asp | Met | Pro | Tyr | Arg<br>350 | Tyr | His |
| Ser | Ser | Leu<br>355 | Gly | Gln | Leu | Asn | Phe<br>360 | Thr | Gly | Ser | Val | Ile<br>365 | Tyr | Glu | Ala |
| Gln | Asp<br>370 | Val | Tyr | Ser | Gly | Asp<br>375 | Ile | Ile | Ser | Gly | Leu<br>380 | Arg | Asp | Glu | Thr |
| Asn<br>385 | Phe | Thr | Val | Ile | Ile<br>390 | Asn | Pro | Ser | Gly | Val<br>395 | Val | Met | Trp | Tyr | Leu<br>400 |
| Tyr | Pro | Ile | Lys | Asn<br>405 | Leu | Glu | Met | Ser | Gln<br>410 | Gln | | | | | |

( 2 ) INFORMATION FOR SEQ ID NO:9:

( i ) SEQUENCE CHARACTERISTICS:
        ( A ) LENGTH: 429 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met<br>1 | Gln | Leu | Arg | Asn<br>5 | Pro | Glu | Leu | His | Leu<br>10 | Gly | Cys | Ala | Leu | Ala<br>15 | Leu |
| Arg | Phe | Leu | Ala<br>20 | Leu | Val | Ser | Trp | Asp<br>25 | Ile | Pro | Gly | Ala | Arg<br>30 | Ala | Leu |

```
Asp  Asn  Gly  Leu  Ala  Arg  Thr  Pro  Thr  Met  Gly  Trp  Leu  His  Trp  Glu
          35                      40                     45

Arg  Phe  Met  Cys  Asn  Leu  Asp  Cys  Gln  Glu  Glu  Pro  Asp  Ser  Cys  Ile
     50                       55                      60

Ser  Glu  Lys  Leu  Phe  Met  Glu  Met  Ala  Glu  Leu  Met  Val  Ser  Glu  Gly
65                       70                      75                           80

Trp  Lys  Asp  Ala  Gly  Tyr  Glu  Tyr  Leu  Cys  Ile  Asp  Asp  Cys  Trp  Met
               85                      90                     95

Ala  Pro  Gln  Arg  Asp  Ser  Glu  Gly  Arg  Leu  Gln  Ala  Asp  Pro  Gln  Arg
               100                    105                    110

Phe  Pro  His  Gly  Ile  Arg  Gln  Leu  Ala  Asn  Tyr  Val  His  Ser  Lys  Gly
          115                    120                    125

Leu  Lys  Leu  Gly  Ile  Tyr  Ala  Asp  Val  Gly  Asn  Lys  Thr  Cys  Ala  Gly
     130                    135                    140

Phe  Pro  Gly  Ser  Phe  Gly  Tyr  Tyr  Asp  Ile  Asp  Ala  Gln  Thr  Phe  Ala
145                      150                    155                          160

Asp  Trp  Gly  Val  Asp  Leu  Leu  Lys  Phe  Asp  Gly  Cys  Tyr  Cys  Asp  Ser
               165                    170                    175

Leu  Glu  Asn  Leu  Ala  Asp  Gly  Tyr  Lys  His  Met  Ser  Leu  Ala  Leu  Asn
               180                    185                    190

Arg  Thr  Gly  Arg  Ser  Ile  Val  Tyr  Ser  Cys  Glu  Trp  Pro  Leu  Tyr  Met
          195                    200                    205

Trp  Pro  Phe  Gln  Lys  Pro  Asn  Tyr  Thr  Glu  Ile  Arg  Gln  Tyr  Cys  Asn
210                      215                    220

His  Trp  Arg  Asn  Phe  Ala  Asp  Ile  Asp  Asp  Ser  Trp  Lys  Ser  Ile  Lys
225                      230                    235                          240

Ser  Ile  Leu  Asp  Trp  Thr  Ser  Phe  Asn  Gln  Glu  Arg  Ile  Val  Asp  Val
               245                    250                    255

Ala  Gly  Pro  Gly  Gly  Trp  Asn  Asp  Pro  Asp  Met  Leu  Val  Ile  Gly  Asn
          260                    265                    270

Phe  Gly  Leu  Ser  Trp  Asn  Gln  Gln  Val  Thr  Gln  Met  Ala  Leu  Trp  Ala
     275                    280                    285

Ile  Met  Ala  Ala  Pro  Leu  Phe  Met  Ser  Asn  Asp  Leu  Arg  His  Ile  Ser
290                      295                    300

Pro  Gln  Ala  Lys  Ala  Leu  Leu  Gln  Asp  Lys  Asp  Val  Ile  Ala  Ile  Asn
305                      310                    315                          320

Gln  Asp  Pro  Leu  Gly  Lys  Gln  Gly  Tyr  Gln  Leu  Arg  Gln  Gly  Asp  Asn
               325                    330                    335

Phe  Glu  Val  Trp  Glu  Arg  Pro  Leu  Ser  Gly  Leu  Ala  Trp  Ala  Val  Ala
               340                    345                    350

Met  Ile  Asn  Arg  Gln  Glu  Ile  Gly  Gly  Pro  Arg  Ser  Tyr  Thr  Ile  Ala
          355                    360                    365

Val  Ala  Ser  Leu  Gly  Lys  Gly  Val  Ala  Cys  Asn  Pro  Ala  Cys  Phe  Ile
     370                    375                    380

Thr  Gln  Leu  Leu  Pro  Val  Lys  Arg  Lys  Leu  Gly  Phe  Tyr  Glu  Trp  Thr
385                      390                    395                          400

Ser  Arg  Leu  Arg  Ser  His  Ile  Asn  Pro  Thr  Gly  Thr  Val  Leu  Leu  Gln
               405                    410                    415

Leu  Glu  Asn  Thr  Met  Gln  Met  Ser  Leu  Lys  Asp  Leu  Leu
               420                    425
```

( 2 ) INFORMATION FOR SEQ ID NO:10:

( i ) SEQUENCE CHARACTERISTICS:

( A ) LENGTH: 404 amino acids
( B ) TYPE: amino acid
( D ) TOPOLOGY: unknown ( i i ) MOLECULE TYPE: protein ( x i ) SEQUENCE DESCRIPTION: SEQ ID NO:10:

```
Met Phe Ala Phe Tyr Phe Leu Thr Ala Cys Ile Ser Leu Lys Gly Val
 1               5                  10                  15
Phe Gly Ser Tyr Asn Gly Leu Gly Leu Thr Pro Gln Met Gly Trp Asp
                20                  25                  30
Asn Trp Asn Thr Phe Ala Cys Asp Val Ser Glu Gln Leu Leu Asp
             35                  40                  45
Thr Ala Asp Arg Ile Ser Asp Leu Gly Leu Lys Asp Met Gly Tyr Lys
        50                  55                  60
Tyr Ile Ile Leu Asp Asp Cys Trp Ser Ser Arg Asp Ser Asp Gly
 65                  70                  75                  80
Phe Leu Val Ala Asp Glu Gln Lys Phe Pro Asn Gly Met Gly His Val
                85                  90                  95
Ala Asp His Leu His Asn Asn Ser Phe Leu Phe Gly Met Tyr Ser Ser
            100                 105                 110
Ala Gly Glu Tyr Thr Cys Ala Gly Tyr Pro Gly Ser Leu Gly Arg Glu
        115                 120                 125
Glu Glu Asp Ala Gln Phe Phe Ala Asn Asn Arg Val Asp Tyr Leu Lys
130                 135                 140
Tyr Asp Asn Cys Tyr Asn Lys Gly Gln Phe Thr Pro Glu Ser Tyr
145                 150                 155                 160
Arg Lys Met Ser Asp Ala Leu Asn Lys Thr Gly Arg Pro Ile Phe Tyr
                165                 170                 175
Ser Cys Asn Trp Gly Leu Tyr Gly Ser Gly Ile Ala Asn Ser Trp Arg
            180                 185                 190
Met Ser Gly Asp Val Thr Ala Glu Phe Thr Arg Pro Asp Ser Cys Pro
        195                 200                 205
Asp Gly Tyr Tyr Ala Gly Phe Ser Ile Met Asn Ile Leu Asn Lys Ala
210                 215                 220
Ala Pro Met Gly Gln Asn Ala Gly Val Gly Gly Trp Asn Asp Leu Asp
225                 230                 235                 240
Asn Leu Glu Val Gly Val Gly Asn Leu Thr Asp Asp Glu Glu Lys Ala
                245                 250                 255
His Phe Ser Met Trp Ala Met Val Lys Ser Pro Leu Ile Ile Gly Ala
            260                 265                 270
Asn Val Asn Asn Leu Lys Ala Ser Ser Tyr Ser Ile Tyr Ser Gln Ala
        275                 280                 285
Ser Val Ile Ala Ile Asn Gln Asp Ser Asn Gly Ile Pro Ala Arg Val
290                 295                 300
Ser Asp Thr Asp Glu Tyr Gly Glu Ile Trp Ser Gly Pro Leu Asp Asn
305                 310                 315                 320
Gly Asp Gln Val Val Ala Leu Leu Asn Gly Gly Ser Val Ser Arg Pro
                325                 330                 335
Met Asn Thr Thr Leu Glu Ile Asp Ser Leu Gly Lys Lys Leu Thr Ser
            340                 345                 350
Thr Asp Asp Leu Trp Ala Asn Arg Val Thr Ala Ser Ile Gly Arg Lys
        355                 360                 365
Thr Gly Leu Tyr Glu Tyr Lys Asp Gly Leu Lys Asn Arg Leu Gly Gln
370                 375                 380
```

```
Lys Gly Ser Leu Ile Leu Asn Val Pro Ala His Ile Ala Phe Arg Leu
385                 390                 395                 400

Arg Pro Ser Ser
```

( 2 ) INFORMATION FOR SEQ ID NO:11:

( i ) SEQUENCE CHARACTERISTICS:
        ( A ) LENGTH: 297 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..279

( x i ) SEQUENCE DESCRIPTION: SEQ ID NO:11:

```
GAA TGG ACT TCA AGG TTA AGA AGT CAC ATA AAT CCC ACA GGA ACT GTT    48
Glu Trp Thr Ser Arg Leu Arg Ser His Ile Asn Pro Thr Gly Thr Val
1               5                   10                  15

TTG CTT CAG CTA GAA AAT ACA ATG CAG ATG TCA TTA AAA GAC TTA CTT    96
Leu Leu Gln Leu Glu Asn Thr Met Gln Met Ser Leu Lys Asp Leu Leu
            20                  25                  30

CCG GCT GGT CCG GCG CAA CAC GAT GAA GCT CAA CAA AAT GCT TTT TAT   144
Pro Ala Gly Pro Ala Gln His Asp Glu Ala Gln Gln Asn Ala Phe Tyr
        35                  40                  45

CAA GTC TTA AAT ATG CCT AAC TTA AAT GCT GAT CAA CGC AAT GGT TTT   192
Gln Val Leu Asn Met Pro Asn Leu Asn Ala Asp Gln Arg Asn Gly Phe
    50                  55                  60

ATC CAA AGC CTT AAA GAT GAT CCA AGC CAA AGT GCT AAC GTT TTA GGT   240
Ile Gln Ser Leu Lys Asp Asp Pro Ser Gln Ser Ala Asn Val Leu Gly
65                  70                  75                  80

GAA GCT CAA AAA CTT AAT GAC TCT CAA GCT CCA AAA TAAGGATCCC        286
Glu Ala Gln Lys Leu Asn Asp Ser Gln Ala Pro Lys
                85                  90

GGAATTCGGC C                                                      297
```

( 2 ) INFORMATION FOR SEQ ID NO:12:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Glu Trp Thr Ser Arg Leu Arg Ser His Ile Asn Pro Thr Gly Thr Val
1               5                   10                  15

Leu Leu Gln Leu Glu Asn Thr Met Gln Met Ser Leu Lys Asp Leu Leu
            20                  25                  30

Pro Ala Gly Pro Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys
                85                  90
```